United States Patent
Franz et al.

(12)

(10) Patent No.: US 6,229,000 B1
(45) Date of Patent: May 8, 2001

(54) TISSUE-SPECIFIC HUMAN NEURONAL CALCIUM CHANNEL SUBTYPES AND THEIR USE

(75) Inventors: Jürgen Franz, Haan; Bernhard Weingärtner, Wuelfrath, both of (DE); Axel Unterbeck; Peter Rae, both of West Haven, CT (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 08/456,200

(22) Filed: May 31, 1995

Related U.S. Application Data

(63) Continuation of application No. 08/094,712, filed on Jul. 19, 1993, now abandoned, which is a continuation-in-part of application No. 07/858,278, filed on Mar. 26, 1992, now abandoned, and a continuation-in-part of application No. 08/064,778, filed on May 19, 1993, now abandoned.

(30) Foreign Application Priority Data

Apr. 4, 1991 (DE) .................................................. 41 10 785

(51) Int. Cl.$^7$ .................................................. C07H 21/04
(52) U.S. Cl. ...................... 536/23.1; 536/23.5; 536/24.1; 536/24.3; 536/24.31
(58) Field of Search .................................. 536/23.1, 23.5, 536/24.1, 24.3, 24.31

(56) References Cited

U.S. PATENT DOCUMENTS

| | | |
|---|---|---|
| 5,386,025 | 1/1995 | Jay et al. . |
| 5,429,921 | 7/1995 | Harpold et al. . |

FOREIGN PATENT DOCUMENTS

| | | |
|---|---|---|
| 8907608 | 8/1989 | (WO) . |
| 8909834 | 10/1989 | (WO) . |

OTHER PUBLICATIONS

Journal Biological Chemistry, vol. 265, No. 33, Nov. 25, 1990, Baltimore, U.S., pp. 20430–20436. E. Perez–Reyes et al.: "Molecular Diversity of L–type Calcium Channels. Evidence for Alternative Splicing of the Transcripts of Three Non–Allelic Genes".

FEBS Letters, vol. 274, No. 1–2, Nov. 1, 1990, Amsterdam, NL, pp. 207–213; P. Huang, et al.: "Polymerase Chain Reaction Cloning of L–Type Calcium Channel Sequenes from the Heart and the Brain".

FEBS Letters, vol. 250, No. 2, Jul. 1989, Amsterdam NL, pp. 386–388; W.J. Koch et al.: "Characterization of cDNA Clones Encoding Two Putative Isoforms of the Alpha1–Subunit of the Dihydropyridine–Sensitive Voltage–Dependent Calcium Channel Isolated from Rat Brain and Rat Aorta".

Society for Neuroscience Abstracts, vol. 17, No. 1–2, 1991, US, p. 772; D.H. Feldman et al.,: Cloning and Expression of a Novel Human Neuronal Calcium Channel.

FEBS Letters, vol. 291, No. 2, Oct. 1991, Amsterdam, NL, pp. 253–258; M. Pragnell et al.: "Cloning and Tissue–Specific Expression of the Brain Calcium Channel Beta–Subunit".

Nature, vol. 350, Apr. 4, 1991, London, Great Britain, pp. 398–402; Y. Mori et al.: "Primary Structure and Functional Expression From Complementary DNA of a Brain Calcium Channel".

Tsien et al., 1988, Trends in Neurol. Sci. 11: pp 431–438.
Tanabe et al., 1987, Nature 328: pp. 313–318.
Grabner et al., 1991, Proc. Natl. Aca. Sci., (USA), 88:pp. 717–731.
Gluzman, 1981, Cell 23: p. 175.
Chen, et al., 1987, Mol. Cel, Biol., 7: pp. 2745–2752.
Sambrook et al., 1989, in: Molecular Cloning, A laboratory manual, ed. Chris Nolan, Cold Spring Harbor Laboratory Press, New. York, N.Y.
Messing et al., 1985, J. Pharmacology and Exp. Therapeutics 235: pp. 407–411.
Rosario et al., 1989, Neurosci. 29, pp. 735–747.
Carbone et al., 1990, Pflugers Arch., 416: pp. 170–179.
Zernig et al., 1986, Eur. J. Pharmacol. 128, pp. 221–229.
Yool and Schwarz, 1991, Nature 349, pp. 700–704.
Sanger et al., 1977, Proc. Natl. Acad. Sci. USA, 74: pp. 5463–5467.
Biel et al 1990 FEBS Lett 269:409
Biel, et al., 1990 Febs Lett 269: 409.*
Muma et al., 1991. Direct Submission to EMBL. 6 listings see Parent /;6 & attachment.*
Mikama et al., 1989 Nature *340* : 230.*

\* cited by examiner

Primary Examiner—Anthony C. Caputa
Assistant Examiner—Stephen Gucker
(74) Attorney, Agent, or Firm—Sprung Kramer Schaefer & Briscoe

(57) ABSTRACT

Disclosed are overlapping cDNA sequences encoding for a human voltage-dependent neuronal calcium channel. The complete cDNA which encodes a voltage-operated calcium channel (VOCC) sub-type is assembled from overlapping lambda phages by means of suitable restriction cleavage sites and cloned into a eukaryotic expression vector.

7 Claims, 3 Drawing Sheets

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 683 nucleotides (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:1:

```
CG GTC CTC TCT GCT ATG ATG GCG CTC TTC ACA GTC TCC              38
   Val Leu Ser Ala Met Met Ala Leu Phe Thr Val Ser
   1               5                   10

ACG TTT GAG GGC TGG CCT GCG TTG CTG TAT AAA GCC ATC             77
Thr Phe Glu Gly Trp Pro Ala Leu Leu Tyr Lys Ala Ile
            15                  20                  25

GAC TCG AAT GGA GAG AAC ATC GGC CCA ATC TAC AAC CAC             116
Asp Ser Asn Gly Glu Asn Ile Gly Pro Ile Tyr Asn His
                30                  35

CGC GTG GAG ATC TCC ATC TTC TTC ATC ATC TAC ATC ATC             155
Arg Val Glu Ile Ser Ile Phe Phe Ile Ile Tyr Ile Ile
    40                  45                  50

ATT GTA GCT TTC TTC ATG ATG AAC ATC TTT GTG GGC TTT             194
Ile Val Ala Phe Phe Met Met Asn Ile Phe Val Gly Phe
                55                  60

GTC ATC GTT ACA TTT CAG GAA CAA GGA GAA AAA GAG TAT             233
Val Ile Val Thr Phe Gln Glu Gln Gly Glu Lys Glu Tyr
65                  70                  75

AAG AAC TGT GAG CTG GAC AAA AAT CAG CGT CAG TGT GTT             272
Lys Asn Cys Glu Leu Asp Lys Asn Gln Arg Gln Cys Val
            80                  85                  90

GAA TAC GCC TTG AAA GCA CGT CCC TTG CGG AGA TAC ATC             311
Glu Tyr Ala Leu Lys Ala Arg Pro Leu Arg Arg Tyr Ile
                95                  100

CCC AAA AAC CCC TAC CAG TAC AAG TTC TGG TAC GTG GTG             350
Pro Lys Asn Pro Tyr Gln Tyr Lys Phe Trp Tyr Val Val
105                 110                 115

AAC TCT TCG CCT TTC GAA TAC ATG ATG TTT GTC CTC ATC             389
Asn Ser Ser Pro Phe Glu Tyr Met Met Phe Val Leu Ile
            120                 125

ATG CTC AAC ACA CTC TGC TTG GCC ATG CAG CAC TAC GAG             428
Met Leu Asn Thr Leu Cys Leu Ala Met Gln His Tyr Glu
130                 135                 140

CAG TCC AAG ATG TTC AAT GAT GCC ATG GAC ATT CTG AAC             467
Glu Ser Lys Met Phe Asn Asp Ala Met Asp Ile Leu Asn
            145                 150                 155

ATG GTC TTC ACC GGG GTG TTC ACC GTC GAG ATG GTT TTG             506
Met Val Phe Thr Gly Val Phe Thr Val Glu Met Val Leu
                160                 165

AAA GTC ATC GCA TTT AAG CCT AAG GGG TAT TTT AGT GAC             545
Lys Val Ile Ala Phe Lys Pro Lys Gly Tyr Phe Ser Asp
170                 175                 180

GCC TGG AAC ACG TTT GAC TCC CTC ATC GTA ATC GGC AGC             584
Ala Trp Asn Thr Phe Asp Ser Leu Ile Val Ile Gly Ser
            185                 190

ATT ATA GAC GTG GCC CTC AGC GAA GCA GAC CCA ACT GAA             623
Ile Ile Asp Val Ala Leu Ser Glu Ala Asp Pro Thr Glu
195                 200                 205

AGT GAA AAT GTC CCT GTC CCA ACT GCT ACA CCT GGG AAC             662
Ser Glu Asn Val Pro Val Pro Thr Ala Thr Pro Gly Asn
            210                 215                 220

TCT GAA GAG AGC AAT AGA ATC                                     683
Ser Glu Glu Ser Asn Arg Ile
                225
```

(2) INFORMATION FOR SEQ ID NO: 2:

(i) SEQUENCE CHARACTERISTICS:
        (A) LENGTH: 4919 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:2:

```
G GAG AAC CGA AGG GCT TTC ATG AAG CTG CGG CGC CAC                37
  Glu Asn Arg Arg Ala Phe Met Lys Leu Arg Arg His
   1               5                  10

GAG CAG ATT GAG CGT GAC GTG AAT GGC TAC CGT GCC TGG              76
Glu Gln Ile Glu Arg Asp Val Asn Gly Tyr Arg Ala Trp
            15                  20                  25

ATA GAC AAA GCA GAG GAA GTC ATG CTC GCT GAA GAA AAT             115
Ile Asp Lys Ala Glu Glu Val Met Leu Ala Glu Glu Asn
                    30                  35

AAA AAT GCT GGA ACA TCC GCC TTA GAA GTG CTT CGA AGG             154
Lys Asn Ala Gly Thr Ser Ala Leu Glu Val Leu Arg Arg
        40                  45                  50

GCA ACC ATG AAG AGG AGC CGG ACA GAG GCC ATG ACT CGA             193
Ala Thr Met Lys Arg Ser Arg Thr Glu Ala Met Thr Arg
                55                  60

GAC TCC AGT GAT GAG CAC TGT GTT GAT ATC TCC TCT GTG             232
Asp Ser Ser Asp Glu His Cys Val Asp Ile Ser Ser Val
 65                  70                  75

GGC ACA CCT CTG GCC CGA GCC AGT ATC AAA AGT GCA AAG             271
Gly Thr Pro Leu Ala Arg Ala Ser Ile Lys Ser Ala Lys
            80                  85                  90

GTA GAC GGG GTC TCT TAT TTC CGG CAC AAG GAA AGG CTT             310
Val Asp Gly Val Ser Tyr Phe Arg His Lys Glu Arg Leu
                    95                 100

CTG CGC ATC TCC ATT CGC CAC ATG GTT AAA TCC CAG GTG             349
Leu Arg Ile Ser Ile Arg His Met Val Lys Ser Gln Val
        105                 110                 115

TTT TAC TGG ATT GTG CTG AGC CTT GTG GCA CTC AAC ACT             388
Phe Tyr Trp Ile Val Leu Ser Leu Val Ala Leu Asn Thr
                120                 125

GCC TGT GTG GCC ATT GTC CAT CAC AAC CAG CCC CAG TGG             427
Ala Cys Val Ala Ile Val His His Asn Gln Pro Gln Trp
130                 135                 140

CTC ACC CAC CTC CTC TAC TAT GCA GAA TTT CTG TTT CTG             466
Leu Thr His Leu Leu Tyr Tyr Ala Glu Phe Leu Phe Leu
        145                 150                 155

GGA CTC TTC CTC TTG GAG ATG TCC CTG AAG ATG TAT GGC             505
Gly Leu Phe Leu Leu Glu Met Ser Leu Lys Met Tyr Gly
                160                 165

ATG GGG CCT GCC CTT TAT TTT CAC TCT TCA TTC AAC TGC             544
Met Gly Pro Ala Leu Tyr Phe His Ser Ser Phe Asn Cys
        170                 175                 180

TTT GAT TTT GGG GTC ACA GTG GGC AGT ATC TTT GAA GTG             583
Phe Asp Phe Gly Val Thr Val Gly Ser Ile Phe Glu Val
                185                 190

GTC TGG GCA ATC TTC AGA CCT GGT ACG TCT TTT GGA ATC             622
Val Trp Ala Ile Phe Arg Pro Gly Thr Ser Phe Gly Ile
195                 200                 205

AGT GTC TTG CGA GCC CTC CGG CTT CTA AGA ATA TTT AAA             661
```

-continued

```
Ser Val Leu Arg Ala Leu Arg Leu Leu Arg Ile Phe Lys
    210                 215                 220

ATA ACC AAG TAT TGG GCT TCC CTA CGG AAT TTG GTG GTC            700
Ile Thr Lys Tyr Trp Ala Ser Leu Arg Asn Leu Val Val
            225                 230

TCC TTG ATG AGC TCA ATG AAG TCT ATC ATC AGT TTG CTT            739
Ser Leu Met Ser Ser Met Lys Ser Ile Ile Ser Leu Leu
    235                 240                 245

TTC CTC CTC TTC CTC TTC ATC GTT GTC TTT GCT CTC CTA            778
Phe Leu Leu Phe Leu Phe Ile Val Val Phe Ala Leu Leu
            250                 255

GGA ATG CAG TTA TTT GGA GGC AGG TTT AAC TTT AAT GAT            817
Gly Met Gln Leu Phe Gly Gly Arg Phe Asn Phe Asn Asp
260                 265                 270

GGG ACT CCT TCG GCA AAT TTT GAT ACC TTC CCT GCA GCC            856
Gly Thr Pro Ser Ala Asn Phe Asp Thr Phe Pro Ala Ala
        275                 280                 285

ATC ATG ACT GTG TTC CAG ATC CTG ACG GGT GAG GAC TGG            895
Ile Met Thr Val Phe Gln Ile Leu Thr Gly Glu Asp Trp
                290                 295

AAT GAG GTG ATG TAC AAT GGG ATC CGC TCC CAG GGT GGG            934
Asn Glu Val Met Tyr Asn Gly Ile Arg Ser Gln Gly Gly
        300                 305                 310

GTC AGC TCA GGC ATG TGG TCT GCC ATC TAC TTC ATT GTG            973
Val Ser Ser Gly Met Trp Ser Ala Ile Tyr Phe Ile Val
                315                 320

CTC ACC TTG TTT GGC AAC TAC ACG CTA CTG AAT GTG TTC            1012
Leu Thr Leu Phe Gly Asn Tyr Thr Leu Leu Asn Val Phe
325                 330                 335

TTG GCT ATC GCT GTG GAT AAT CTC GCC AAC GCC CAG GAA            1051
Leu Ala Ile Ala Val Asp Asn Leu Ala Asn Ala Gln Glu
        340                 345                 350

CTG ACC AAG GAT GAA CAG GAG GAA GAA GAG GCC TTC AAC            1090
Leu Thr Lys Asp Glu Gln Glu Glu Glu Glu Ala Phe Asn
                355                 360

CAG AAA CAT GCA CTG CAG AAG GCC AAG GAG GTC AGC CCG            1129
Gln Lys His Ala Leu Gln Lys Ala Lys Glu Val Ser Pro
        365                 370                 375

ATG TCT GCA CCC AAC ATG CCT TCG ATC GAA AGA GAC AGA            1168
Met Ser Ala Pro Asn Met Pro Ser Ile Glu Gly Arg Asp Arg
                380                 385

AGG AGA AGA CAC CAC ATG TCG ATG TGG GAG CCA CGC AGC            1207
Arg Arg Arg His His Met Ser Met Trp Glu Pro Arg Ser
390                 395                 400

AGC CAC CTG AGG GAG CGG NNN NNN NGG CAC CAC ATG TCC            1246
Ser His Leu Arg Glu Arg Arg Arg Arg His His Met Ser
        405                 410                 415

GTG TGG GAG CAG CGT ACC AGC CAG CTG AGG AAG CAC ATG            1285
Val Trp Glu Gln Arg Thr Ser Gln Leu Arg Lys His Met
                420                 425

CAG ATG TCC AGC CAG GAG GCC CTC AAC AGA GAG GAG GCG            1324
Gln Met Ser Ser Gln Glu Ala Leu Asn Arg Glu Glu Ala
        430                 435                 440

CCG ACC ATG AAC CCG CTC AAC CCC CTC AAC CCG CTC AGC            1363
Pro Thr Met Asn Pro Leu Asn Pro Leu Asn Pro Leu Ser
                445                 450

TCC CTC AAC CCG CTC AAT GCC CAC CCC AGC CTT TAT CGG            1402
Ser Leu Asn Pro Leu Asn Ala His Pro Ser Leu Tyr Arg
455                 460                 465
```

-continued

| | | |
|---|---|---|
| CGA CCC AGG GCC ATT GAG GGC TGG CCT GGG CTG GCC CTG<br>Arg Pro Arg Ala Ile Glu Gly Trp Pro Gly Leu Ala Leu<br>470 475 480 | | 1441 |
| GAG AAG TTC GAG GAG GAG CGC ATC AGC CGT GGG GGG TCC<br>Glu Lys Phe Glu Glu Glu Arg Ile Ser Arg Gly Gly Ser<br>485 490 | | 1480 |
| CTC AAG GGG GAT GGA GGG GAC CGA TCC AGT GCC CTG GAC<br>Leu Lys Gly Asp Gly Gly Asp Arg Ser Ser Ala Leu Asp<br>495 500 505 | | 1519 |
| AAC CAG AGG ACC CCT TTG TCC CTG GGC CAG CGG GAG CCA<br>Asn Gln Arg Thr Pro Leu Ser Leu Gly Gln Arg Glu Pro<br>510 515 | | 1558 |
| CCA TGG CTG GCC AGG CCC TGT CAT GGA AAC TGT GAC CCG<br>Pro Trp Leu Ala Arg Pro Cys His Gly Asn Cys Asp Pro<br>520 525 530 | | 1597 |
| ACT CAG CAG GAG GCA GGG GGA GGA GAG GCT GTG GTG ACC<br>Thr Gln Gln Glu Ala Gly Gly Gly Glu Ala Val Val Thr<br>535 540 545 | | 1636 |
| TTT GAG GAC CGG GCC AGG CAC AGG CAG AGC CAA CGG CGC<br>Phe Glu Asp Arg Ala Arg His Arg Gln Ser Gln Arg Arg<br>550 555 | | 1675 |
| AGC GCG CAT CGC CGC GTC AGG ACA GAA GGC AAG GAG TCC<br>Ser Ala His Arg Arg Val Arg Thr Glu Gly Lys Glu Ser<br>560 565 570 | | 1714 |
| TCT TCA GCC TCC CGG AGC AGG TCT GCC AGC CAG GAA CGC<br>Ser Ser Ala Ser Arg Ser Arg Ser Ala Ser Gln Glu Arg<br>575 580 | | 1753 |
| AGT CTG GAT GAA GCC ATG CCC ACT GAA GGG GAG AAG GAC<br>Ser Leu Asp Glu Ala Met Pro Thr Glu Gly Glu Lys Asp<br>585 590 595 | | 1792 |
| CAT GAG CTC AGG GGC AAC CAT GGT GCC AAG GAG CCA ACG<br>His Glu Leu Arg Gly Asn His Gly Ala Lys Glu Pro Thr<br>600 605 610 | | 1831 |
| ATC CAA GAA GAG AGA GCC CAG GAT TTA AGG AGG ACC AAC<br>Ile Gln Glu Glu Arg Ala Gln Asp Leu Arg Arg Thr Asn<br>615 620 | | 1870 |
| AGT CTG ATG GTG TCC AGA GGC TCC GGG CTG GCA GGA GGC<br>Ser Leu Met Val Ser Arg Gly Ser Gly Leu Ala Gly Gly<br>625 630 635 | | 1909 |
| CTT GAT GAG GCT GAC ACC CCC CTA GTC CTG CCC CAT CCT<br>Leu Asp Glu Ala Asp Thr Pro Leu Val Leu Pro His Pro<br>640 645 | | 1948 |
| GAG CTG GAA GTG GGG AAC GAC GTG GTG TCG ACG GAG CAG<br>Glu Leu Glu Val Gly Asn Asp Val Val Ser Thr Glu Gln<br>650 655 660 | | 1987 |
| GAG CCA GAA GGC AGC AGT GAG CAG GCC CTG CTG GGG AAT<br>Glu Pro Glu Gly Ser Ser Glu Gln Ala Leu Leu Gly Asn<br>665 670 675 | | 2026 |
| GTG CAG CTA GAC ATG GGC CGG GTC ATC AGC CAG AGC GAG<br>Val Gln Leu Asp Met Gly Arg Val Ile Ser Gln Ser Glu<br>680 685 | | 2065 |
| CCT GAC CTC TCC TGC ATC ACG GCC AAC ACG GAC AAG GCC<br>Pro Asp Leu Ser Cys Ile Thr Ala Asn Thr Asp Lys Ala<br>690 695 700 | | 2104 |
| ACC ACC GAG AGC ACC AGC GTC ACC GTC GCC ATC CCC GAC<br>Thr Thr Glu Ser Thr Ser Val Thr Val Ala Ile Pro Asp<br>705 710 | | 2143 |
| GTG GAC CCC TTG GTG GAC TCA ACC GTG GTG CAC ATT AGC<br>Val Asp Pro Leu Val Asp Ser Thr Val Val His Ile Ser<br>715 720 725 | | 2182 |

```
AAC AAG NCG GAT GGG GAA GCC AGT CCC TTG AAG GAG GCA            2221
Asn Lys Thr Asp Gly Glu Ala Ser Pro Leu Lys Glu Ala
            730                 735                 740

GAG ATC AGA GAG GAT GAG GAG GTG GAG AAG AAG AAG                2260
Glu Ile Arg Glu Asp Glu Glu Val Glu Lys Lys Lys
                745                 750

CAG AAG AAG GAG AAG CGT GAG ACA GGC AAA GNC ATG GTG            2299
Gln Lys Lys Glu Lys Arg Glu Thr Gly Lys Ala Met Val
    755                 760                 765

CCC CAC AGC TCA ATG TTC ATC TTC AGC ACC ACC AAC CCG            2338
Pro His Ser Ser Met Phe Ile Phe Ser Thr Thr Asn Pro
            770                 775

ATC CGG AGG GCC TGC CAC TAC ATC GTG AAC CTG CGC TAC            2377
Ile Arg Arg Ala Cys His Tyr Ile Val Asn Leu Arg Tyr
780                 785                 790

TTT GAG ATG TGC ATC CTC CTG GTG ATT GCA GCC AGC AGC            2416
Phe Glu Met Cys Ile Leu Leu Val Ile Ala Ala Ser Ser
        795                 800                 805

ATC GCC CTG GCN GCA GAG GAC CCC GNC NTG ACC AAC TCG            2455
Ile Ala Leu Ala Ala Glu Asp Pro Val Leu Thr Asn Ser
                810                 815

GAG CGC AAC AAA GTN CTG AGG TAT TTT GAC TAT GTG TTC            2494
Glu Arg Asn Lys Val Leu Arg Tyr Phe Asp Tyr Val Phe
    820                 825                 830

ACG NGC GAG TTC ACC TTT GAG ATG GTT ATA NAG ATG ATA            2533
Thr Gly Glu Phe Thr Phe Glu Met Val Ile Lys Met Ile
            835                 840

GAC CAA GGC TTG ATC CTG CAG GAT GGG TNC TAC TTC CGA            2572
Asp Gln Gly Leu Ile Leu Gln Asp Gly Ser Tyr Phe Arg
845                 850                 855

GAC TTG TGG AAC ATC CTG GAC TTT GTG GTG GTC GTT GGC            2611
Asp Leu Trp Asn Ile Leu Asp Phe Val Val Val Val Gly
        860                 865                 870

GCA TTG GTG GCC TTT GCT CTG GCG AAC GCT TTG GGA ACC            2650
Ala Leu Val Ala Phe Ala Leu Ala Asn Ala Leu Gly Thr
                875                 880

AAC AAA GGA CGG GAC ATC AAG ACC ATC AAG TCT CTG CGG            2689
Asn Lys Gly Arg Asp Ile Lys Thr Ile Lys Ser Leu Arg
    885                 890                 895

GTG CTC CGA GTT CTA AGG CCA CTG AAA ACC ATC AAG CGC            2728
Val Leu Arg Val Leu Arg Pro Leu Lys Thr Ile Lys Arg
            900                 905

TTG CCC AAG CTC AAG GCC GTC TTC GAC TGC GTA GTG ACC            2767
Leu Pro Lys Leu Lys Ala Val Phe Asp Cys Val Val Thr
910                 915                 920

TCC TTG AAG AAT GTC TTC AAC ATA CTC ATT GTG TAC AAG            2806
Ser Leu Lys Asn Val Phe Asn Ile Leu Ile Val Tyr Lys
        925                 930                 935

CTC TTC ATG TTC ATC TTT GCT GTC ATC GCA GTT CAG CTC            2845
Leu Phe Met Phe Ile Phe Ala Val Ile Ala Val Gln Leu
                940                 945

TTC AAG GGA AAG TTC TTT TAT TGC ACG GAC AGT TCC AAG            2884
Phe Lys Gly Lys Phe Phe Tyr Cys Thr Asp Ser Ser Lys
    950                 955                 960

GAC ACA GAG AAG GAG TGC ATA GGC AAC TAT GTA GAT CAT            2923
Asp Thr Glu Lys Glu Cys Ile Gly Asn Tyr Val Asp His
            965                 970

GAG AAA AAC AAG ATG GAG GTG AAG GGC CGG GAA TGG AAG            2962
Glu Lys Asn Lys Met Glu Val Lys Gly Arg Glu Trp Lys
```

-continued

| | | |
|---|---|---|
| 975 | 980 | 985 |

| | |
|---|---|
| CGC CAT GAA TTC CAC TAC GAC AAC ATT ATC TGG GCC CTG<br>Arg His Glu Phe His Tyr Asp Asn Ile Ile Trp Ala Leu<br>    990             995                 1000 | 3001 |
| CTG ACC CTC TTC ACC GTC TCC ACA GGG GAA GGA TGG CCT<br>Leu Thr Leu Phe Thr Val Ser Thr Gly Glu Gly Trp Pro<br>        1005            1010 | 3040 |
| CAA GTT CTG CAG CAC TCT GTA GAT GTG ACA GAG GAA GAC<br>Gln Val Leu Gln His Ser Val Asp Val Thr Glu Glu Asp<br>    1015            1020            1025 | 3079 |
| CGA GGC CCA AGC CGC AGC AAC CGC ATG GAG ATG TCT ATC<br>Arg Gly Pro Ser Arg Ser Asn Arg Met Glu Met Ser Ile<br>        1030            1035 | 3118 |
| TTT TAT GTA GTC TAC TTT GTG GTC TTC CCC TTC TTC TTT<br>Phe Tyr Val Val Tyr Phe Val Val Phe Pro Phe Phe Phe<br>1040            1045            1050 | 3157 |
| GTC AAT ATC TTT GTG GCT CTC ATC ATC ATC ACC TTC CAG<br>Val Asn Ile Phe Val Ala Leu Ile Ile Ile Thr Phe Gln<br>        1055            1060            1065 | 3196 |
| GAG CAA GGG GAT AAG ATG ATG GAG GAG TGC AGC CTG GAG<br>Glu Gln Gly Asp Lys Met Met Glu Glu Cys Ser Leu Glu<br>            1070            1075 | 3235 |
| AAG AAT GAG AGG GCG TGC ATC GAC TTC GCC ATC AGC GCC<br>Lys Asn Glu Arg Ala Cys Ile Asp Phe Ala Ile Ser Ala<br>1080            1085            1090 | 3274 |
| AAA CCT CTC ACC CGC TAC ATG TTG CAG AAC AGA CAC ACC<br>Lys Pro Leu Thr Arg Tyr Met Leu Gln Asn Arg His Thr<br>        1095            1100 | 3313 |
| TTC CAG TAC CGC GTG TGG CAC TTT GTG GTG TCT CCG TCC<br>Phe Gln Tyr Arg Val Trp His Phe Val Val Ser Pro Ser<br>1105            1110            1115 | 3352 |
| TTT GAG TAC ACC ATT ATG GCC ATG ATC GCC TTG AAT ACT<br>Phe Glu Tyr Thr Ile Met Ala Met Ile Ala Leu Asn Thr<br>        1120            1125            1130 | 3391 |
| GTT GTG CTG ATG ATG AAG TAT TAT TCT GCT CCC TGT ACC<br>Val Val Leu Met Met Lys Tyr Tyr Ser Ala Pro Cys Thr<br>            1135            1140 | 3430 |
| TAT GAG CTG GCC CTG AAG TAC CTG AAT ATC GCC TTC ACC<br>Tyr Glu Leu Ala Leu Lys Tyr Leu Asn Ile Ala Phe Thr<br>    1145            1150            1155 | 3469 |
| ATG GTG TTT TCC CTG GAA TGT GTC CTG AAG GTC ATC GCT<br>Met Val Phe Ser Leu Glu Cys Val Leu Lys Val Ile Ala<br>        1160            1165 | 3508 |
| TTT GGC TTT TTG AAC TAT TTC CGA GAC ACC TGG AAT ATC<br>Phe Gly Phe Leu Asn Tyr Phe Arg Asp Thr Trp Asn Ile<br>1170            1175            1180 | 3547 |
| TTT GAC TTC ATC ACC GTG ATT GGC AGT ATC ACA GAA ATT<br>Phe Asp Phe Ile Thr Val Ile Gly Ser Ile Thr Glu Ile<br>        1185            1190            1195 | 3586 |
| ATC CTG ACA GAC AGC AAG CTG GTG AAC ACC AGT GGC TTC<br>Ile Leu Thr Asp Ser Lys Leu Val Asn Thr Ser Gly Phe<br>            1200            1205 | 3625 |
| AAT ATG AGC TTT CTG AAG CTC TTC CGA GCT GCC CGC CTC<br>Asn Met Ser Phe Leu Lys Leu Phe Arg Ala Ala Arg Leu<br>    1210            1215            1220 | 3664 |
| ATA AAG CTC CTG CGT CAG GGC TAT ACC ATA CGC ATT TTG<br>Ile Lys Leu Leu Arg Gln Gly Tyr Thr Ile Arg Ile Leu<br>        1225            1230 | 3703 |
| CTG TGG ACC TTT GTG CAG TCC TTT AAG GCC CTC CCT TAT | 3742 |

```
                                                     -continued

Leu Trp Thr Phe Val Gln Ser Phe Lys Ala Leu Pro Tyr
1235                1240                1245

GTC TGC CTT TTA ATT GCC ATG CTT TTC TTC ATT TAT GCC            3781
Val Cys Leu Leu Ile Ala Met Leu Phe Phe Ile Tyr Ala
    1250                1255                1260

ATC ATT GGG ATG CAG GTA TTT GGA AAC ATA AAA TTA GAC            3820
Ile Ile Gly Met Gln Val Phe Gly Asn Ile Lys Leu Asp
                1265                1270

GAG GAG AGT CAC ATC AAC CGG CAC AAC AAC TTC CGG AGT            3859
Glu Glu Ser His Ile Asn Arg His Asn Asn Phe Arg Ser
    1275                1280                1285

TTC TTT GGG TCC CTA ATG CTA CTC TTC AGG AGT GCC ACA            3898
Phe Phe Gly Ser Leu Met Leu Leu Phe Arg Ser Ala Thr
                1290                1295

GGT GAG GCC TGG CAG GAG ATT ATG CTG TCA TGC CTT GGG            3937
Gly Glu Ala Trp Gln Glu Ile Met Leu Ser Cys Leu Gly
1300                1305                1310

GAG AAG GGC TGT GAG CCT GAC ACC ACC GCA CCA TCA GGG            3976
Glu Lys Gly Cys Glu Pro Asp Thr Thr Ala Pro Ser Gly
                1315                1320                1325

CAG AAC GAG AAC GAA CGC TGC GGC ACC GAT CTG GCC TAC            4015
Gln Asn Glu Asn Glu Arg Cys Gly Thr Asp Leu Ala Tyr
                    1330                1335

GTG TAC TTT GTC TCC TTC ATC TTC TTC TGC TCC TTC TTG            4054
Val Tyr Phe Val Ser Phe Ile Phe Phe Cys Ser Phe Leu
    1340                1345                1350

ATG CTC AAC CTG TTT GTG GCC GTC ATC ATG GAC AAC TTT            4093
Met Leu Asn Leu Phe Val Ala Val Ile Met Asp Asn Phe
                1355                1360

GAG TAC CTG ACT CGG GAC TCC TCC ATC CTG GGG CCT CAC            4132
Glu Tyr Leu Thr Arg Asp Ser Ser Ile Leu Gly Pro His
1365                1370                1375

CAC TTG GAC GAG TTT GTC CGC GTC TGG GCA GAA TAT GAC            4171
His Leu Asp Glu Phe Val Arg Val Trp Ala Glu Tyr Asp
    1380                1385                1390

CGA GCA GCA TGG TGC GTA GGC CCC TCG GCC CCG CCA GCG            4210
Arg Ala Ala Trp Cys Val Gly Pro Ser Ala Pro Pro Ala
                1395                1400

AGC GGG GCC CAG AGC AAA GGT CTC TGG AGT TCC CAG GGA            4249
Ser Gly Ala Gln Ser Lys Gly Leu Trp Ser Ser Gln Gly
    1405                1410                1415

AGA GGC TGG AAT TGG AGC CAC CCA AAT GCC TGC CTG TTA            4288
Arg Gly Trp Asn Trp Ser His Pro Asn Ala Cys Leu Leu
                1420                1425

CAG AAG GAA AGG AGA TTC CTC TTG ATT GTG GCC CAT AGA            4327
Gln Lys Glu Arg Arg Phe Leu Leu Ile Val Ala His Arg
1430                1435                1440

AGA GGC TCT GGT ATC AAG CCA GTC ACC AAG GAC TTC TGT            4366
Arg Gly Ser Gly Ile Lys Pro Val Thr Lys Asp Phe Cys
    1445                1450                1455

ATC CTC CTT TCC CCT CTC TTT CCT TCT GTG ACA GGG TTT            4405
Ile Leu Leu Ser Pro Leu Phe Pro Ser Val Thr Gly Phe
                1460                1465

TCC CTT TGT GGG CTG GTC TCA TCA TCC AGT CCT CAC CTC            4444
Ser Leu Cys Gly Leu Val Ser Ser Ser Ser Pro His Leu
    1470                1475                1480

AGA TTA TTT GGG CTC AGT CCC AAG AGA ACT TTC CAA                4480
Arg Leu Phe Gly Leu Ser Pro Lys Arg Thr Phe Gln
                1485                1490
```

```
TAATCTTTTT CTGCCAATGG TTAGTGGACT CCTTTGAGTT                   4520

ATCAGGGGGT TTGACAAGGG TTTTTGGCCA GCTGGACATC                   4560

TGGCCACCAT GATCAGTGAC TGTGTTTTCT CTTTCTCGTT                   4600

CCTCTCAACA GATACAGTTG GATATAACTC TGAAATTATT                   4640

TTTTAAAAAC CAAACAAGTT GTTCTTCCAA CTGTTCCCTT                   4680

AAATATTTGT GGATTTTTAT TACATGGAAC TAAATTAAAT                   4720

GGTAGGAATT GGTGAAGATA ACTTCTTTAC TGTCTCTTTT                   4760

GCTGTTTAGT AGTTCTGAAG TGATAGCGTG CCTTCTAGGC                   4800

TCTAGAGCAG GGATTGGCAA ACTACATCCC ATGGGCAAAA                   4840

TTCAGCCCAT TGTCTGTTTT TGCAAATAAA GTTTGGTCNG                   4880

TCTTGCGCCG GTCCAAGAAT TCACCTCTA GCGGCGCAA                     4919
```

(2) INFORMATION FOR SEQ ID NO: 3:

(i) SEQUENCE CHARACTERISTICS:
        (A) LENGTH: 811 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:3:

```
G GTC AAC TCC ACC TAC TTC GAG TAC CTG ATG TTC GTC              37
  Val Asn Ser Thr Tyr Phe Glu Tyr Leu Met Phe Val
   1               5                  10

CTC ATC CTG CTC AAC ACC ATC TGC CTG GCC ATG CAG CAC            76
Leu Ile Leu Leu Asn Thr Ile Cys Leu Ala Met Gln His
         15                  20                  25

TAC GGC CAG AGC TGC CTG TTC AAA ATC GCC ATG AAC ATC           115
Tyr Gly Gln Ser Cys Leu Phe Lys Ile Ala Met Asn Ile
                 30                  35

CTC AAC ATG CTC TTC ACT GGC CTC TTC ACC GTG GAG ATG           154
Leu Asn Met Leu Phe Thr Gly Leu Phe Thr Val Glu Met
     40                  45                  50

ATC CTG AAG GTC ATT GCC TTC AAA CCC AAG CAC TAT TTC           193
Ile Leu Lys Val Ile Ala Phe Lys Pro Lys His Tyr Phe
             55                  60

TGT GAT GCA TGG AAT ACA TTT GAC NCC TTG ATT GTT GTG           232
Cys Asp Ala Trp Asn Thr Phe Asp Xaa Leu Ile Val Val
 65                  70                  75

GGT AGC ATT GTT GAT ATA GCA ATC ACC GAG GTA AAC CCA           271
Gly Ser Ile Val Asp Ile Ala Ile Thr Glu Val Asn Pro
             80                  85                  90

GCT GAA CAT ACC CAA TGC TCT CCC TCT ATG AAC GCA GAG           310
Ala Glu His Thr Gln Cys Ser Pro Ser Met Asn Ala Glu
                 95                 100

GAA AAC TCC CGC ATC TCC ATC ACC TTC TTC CGC CTG TTC           349
Glu Asn Ser Arg Ile Ser Ile Thr Phe Phe Arg Leu Phe
    105                 110                 115

CGG GTC ATG CGT CTG GTG AAG CTG CTG AGC CGT GGG GAG           388
Arg Val Met Arg Leu Val Lys Leu Leu Ser Arg Gly Glu
            120                 125

GGC ATC CGG ATG CTG CTG TGG ACC TTC ATC AAG TCC TTC           427
Gly Ile Arg Thr Leu Leu Trp Thr Phe Ile Lys Ser Phe
130                 135                 140
```

```
CAG GCC CTG CCC TAT GTG GCC CTC CTG ATC GTG ATG CTG           466
Gln Ala Leu Pro Tyr Val Ala Leu Leu Ile Val Met Leu
        145                 150                 155

TTC TTC ATC TAC GCG GTG ATC GGG ATG CAG GTG TTT GGG           505
Phe Phe Ile Tyr Ala Val Ile Gly Met Gln Val Phe Gly
                160                 165

AAA ATT GCC CTG AAT GAT ACC ACA GAG ATC AAC CGG AAC           544
Lys Ile Ala Leu Asn Asp Thr Thr Glu Ile Asn Arg Asn
170                 175                 180

AAC AAC TTT CAG ACC TTC CCC CAG GCC GTG CTG CTC CTC           583
Asn Asn Phe Gln Thr Phe Pro Gln Ala Val Leu Leu Leu
            185                 190

TTC AGG TGT GCC ACC GGG GAG GCC TGG CAG GAC ATC ATG           622
Phe Arg Cys Ala Thr Gly Glu Ala Trp Gln Asp Ile Met
195                 200                 205

CTG GCC TGC ATG CCA GGC AAG AAG TGT GCC CCA GAG TCC           661
Leu Ala Cys Met Pro Gly Lys Lys Cys Ala Pro Glu Ser
        210                 215                 220

GAG CCC AGC AAC AGC ACG GAG GGT GAA ACA CCC TGT GGT           700
Glu Pro Ser Asn Ser Thr Glu Gly Glu Thr Pro Cys Gly
                225                 230

AGC AGC TTT GCT GTC TTC TAC TTC ATC AGC TTC TAC ATG           739
Ser Ser Phe Ala Val Phe Tyr Phe Ile Ser Phe Tyr Met
235                 240                 245

CTC TGT GCC TTC CTG ATC ATC AAC CTC TTT GTA GCT GTC           778
Leu Cys Ala Phe Leu Ile Ile Asn Leu Phe Val Ala Val
            250                 255

ATC ATG GAC AAC TTT GAC TAC CTG ACA AGG GAC                   811
Ile Met Asp Asn Phe Asp Tyr Leu Thr Arg Asp
260                 265                 270

(2) INFORMATION FOR SEQ ID NO: 4:

(i) SEQUENCE CHARACTERISTICS:
        (A) LENGTH: 1354 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:4:

GTG GTG TTC CCC TTC TTC TTT GTC AAT ATC TTT GTG GCC           39
Val Val Phe Pro Phe Phe Phe Val Asn Ile Phe Val Ala
1                   5                   10

TTG ATC ATC ATC ACC TTC CAG GAG CAA GGG GAC AAG ATG           78
Leu Ile Ile Ile Thr Phe Gln Glu Gln Gly Asp Lys Met
        15                  20                  25

ATG GAG GAA TAC AGC CTG GAG AAA AAT GAG AGG GCC TGC           117
Met Glu Glu Tyr Ser Leu Glu Lys Asn Glu Arg Ala Cys
                30                  35

ATT GAT TTC GCC ATC AGC GCC AAG CCG CTG ACC CGA CAC           156
Ile Asp Phe Ala Ile Ser Ala Lys Pro Leu Thr Arg His
40                  45                  50

ATG CCG CAG AAC AAG CAG AGC TTC CAG TAC CGC ATG TGG           195
Met Pro Gln Asn Lys Gln Ser Phe Gln Tyr Arg Met Trp
            55                  60                  65

CAG TTC GTG GTG TCT CCG CCT TTC GAG TAC ACG ATC ATG           234
Gln Phe Val Val Ser Pro Pro Phe Glu Tyr Thr Ile Met
                70                  75

GCC ATG ATC GCC CTC AAC ACC ATC GTG CTT ATG ATG AAG           273
Ala Met Ile Ala Leu Asn Thr Ile Val Leu Met Met Lys
```

-continued

```
              80                      85                      90
TTC TAT GGG GCT TCT GTT GCT TAT GAA AAT GCC CTG CGG                        312
Phe Tyr Gly Ala Ser Val Ala Tyr Glu Asn Ala Leu Arg
            95                      100

GTG TTC AAC ATC GTC TTC ACC TCC CTC TTC TCT CTG GAA                        351
Val Phe Asn Ile Val Phe Thr Ser Leu Phe Ser Leu Glu
105                     110                     115

TGT GTG CTG AAA GTC ATG GCT TTT GGG ATT CTG AAT TAT                        390
Cys Val Leu Lys Val Met Ala Phe Gly Ile Leu Asn Tyr
            120                     125                     130

TTC CGC GAT GCC TGG AAC ATC TTC GAC TTT GTG ACT GTT                        429
Phe Arg Asp Ala Trp Asn Ile Phe Asp Phe Val Thr Val
                135                     140

CTG GGC AGC ATC ACC GAT ATC CTC GTG ACT GAG TTT GGG                        468
Leu Gly Ser Ile Thr Asp Ile Leu Val Thr Glu Phe Gly
            145                     150                     155

AAT AAC TTC ATC AAC CTG AGC TTT CTC CGC CTC TTC CGA                        507
Asn Asn Phe Ile Asn Leu Ser Phe Leu Arg Leu Phe Arg
                160                     165

GCT GCC CGG CTC ATC AAA CTT CTC CGT CAG GGT TAC ACC                        546
Ala Ala Arg Leu Ile Lys Leu Leu Arg Gln Gly Tyr Thr
170                     175                     180

ATC CGC ATT CTT CTC TGG ACC TTT GTG CAG TCC TTC AAG                        585
Ile Arg Ile Leu Leu Trp Thr Phe Val Gln Ser Phe Lys
            185                     190                     195

GCC CTG CCT TAT GTC TGT CTG CTG ATC GCC ATG CTC TTC                        624
Ala Leu Pro Tyr Val Cys Leu Leu Ile Ala Met Leu Phe
                200                     205

TTC ATC TAT GCC ATC ATT GGG ATA CAG GTG TTT GGT AAC                        663
Phe Ile Tyr Ala Ile Ile Gly Ile Gln Val Phe Gly Asn
210                     215                     220

ATT GGC ATC GAC GTG GAG GAC GAG GAC AGT GAT GAA GAT                        702
Ile Gly Ile Asp Val Glu Asp Glu Asp Ser Asp Glu Asp
            225                     230

GAG TTC CAA ATC ACT GAG CAC AAT AAC TTC CGG ACC TTC                        741
Glu Phe Gln Ile Thr Glu His Asn Asn Phe Arg Thr Phe
235                     240                     245

TTC CAG GCC CTC ATG CTT CTC TTC CGG AGT GCC ACC GGG                        780
Phe Gln Ala Leu Met Leu Leu Phe Arg Ser Ala Thr Gly
            250                     255                     260

GAA GCT TGG CAC AAC ATC ATG CTT TCC TGC CTC AGC GGG                        819
Glu Ala Trp His Asn Ile Met Leu Ser Cys Leu Ser Gly
                265                     270

AAA CCG TGT GAT AAG AAC TCT GGC ATC CTG ACT CGA GAG                        858
Lys Pro Cys Asp Lys Asn Ser Gly Ile Leu Thr Arg Glu
275                     280                     285

TGT GGC AAT GAA TTT GCT TAT TTT TAC TTT GTT TCC TTC                        897
Cys Gly Asn Glu Phe Ala Tyr Phe Tyr Phe Val Ser Phe
            290                     295

ATC TTC CTC TGC TCG TTT CTG ATG CTG AAT CTC TTT GTC                        936
Ile Phe Leu Cys Ser Phe Leu Met Leu Asn Leu Phe Val
300                     305                     310

GCC GTC ATC ATG GAC AAC TTT GAG TAC CTC ACC CGA GAC                        975
Ala Val Ile Met Asp Asn Phe Glu Tyr Leu Thr Arg Asp
            315                     320                     325

TCC TCC ATC CTG GGC CCC CAC CAC CTG GAT GAG TAC GTG                       1014
Ser Ser Ile Leu Gly Pro His His Leu Asp Glu Tyr Val
                330                     335

CGT GTC TGG GCC GAG TAT GAC CCC GCA GCT TGG GGC CGC                       1053
```

```
                Arg Val Trp Ala Glu Tyr Asp Pro Ala Ala Trp Gly Arg
                    340                 345                 350

ATG CCT TAC CTG GAC ATG TAT CAG ATG CTG AGA CAC ATG                       1092
Met Pro Tyr Leu Asp Met Tyr Gln Met Leu Arg His Met
            355                 360

TCT CCG CCC CTG GGT CTG GGG AAG AAG TGT CCG GCC AGA                       1131
Ser Pro Pro Leu Gly Leu Gly Lys Lys Cys Pro Ala Arg
365                 370                 375

GTG GCT TAC AAG CTT CTT CTG CGG ATG GAC CTG CCC GTC                       1170
Val Ala Tyr Lys Leu Leu Leu Arg Met Asp Leu Pro Val
            380                 385                 390

GCA GAT GAC AAC ACC GTC CAC TTC AAT TCC ACC CTC ATG                       1209
Ala Asp Asp Asn Thr Val His Phe Asn Ser Thr Leu Met
                395                 400

GCT CTG ATC CGC ACA GCC CTG GAC ATC AAG ATT GCC AAG                       1248
Ala Leu Ile Arg Thr Ala Leu Asp Ile Lys Ile Ala Lys
405                 410                 415

GGA GGA GCC GAC AAA CAG CAG ATG GAC GCT GAG CTG CGG                       1287
Xaa Gly Ala Asp Lys Gln Gln Met Asp Ala Glu Leu Arg
            420                 425

AAG GAG ATG ATG GCG ATT TGG CCC AAT CTG TCC CAG AAG                       1326
Lys Glu Met Met Ala Ile Trp Pro Asn Leu Ser Gln Lys
430                 435                 440

ACG CTA GAC CTG CTG GTC ACA CCT CAC A                                     1354
Thr Leu Asp Leu Leu Val Thr Pro His
            445                 450

(2) INFORMATION FOR SEQ ID NO: 5:

(i) SEQUENCE CHARACTERISTICS:
           (A) LENGTH: 5438 nucleotides
           (B) TYPE: Nucleotide
           (C) STRANDEDNESS: Single
           (D) TOPOLOGY: Linear (ii) MOLECULE TYPE: cDNA (xi) SEQUENCE DESCRIPTION: SEQ ID NO:5:

G GAC TGC AGG GGT CAG TAT TTG GAT TAT GAG AAG GAG                           37
  Asp Cys Arg Gly Gln Tyr Leu Asp Tyr Glu Lys Glu
  1               5                   10

GAA GTG GAA GCT CAG CCC AGG CAG TGG AAG AAA TAC GAC                         76
Glu Val Glu Ala Gln Pro Arg Gln Trp Lys Lys Tyr Asp
            15                  20                  25

TTT CAC TAC GAC AAT GTG CTC TGG GCT CTG CTG ACG CTG                        115
Phe His Tyr Asp Asn Val Leu Trp Ala Leu Leu Thr Leu
                30                  35

TTC ACA GTG TCC ACG GGA GAA GGC TGG CCC ATG GTG CTG                        154
Phe Thr Val Ser Thr Gly Glu Gly Trp Pro Met Val Leu
    40                  45                  50

AAA CAC TCC GTG GAT GCC ACC TAT GAG GAG CAG GGT CCA                        193
Lys His Ser Val Asp Ala Thr Tyr Glu Glu Gln Gly Pro
            55                  60

AGC CCT GGG TAC CGC ATG GAG CTG TCC ATC TTC TAC GTG                        232
Ser Pro Gly Tyr Arg Met Glu Leu Ser Ile Phe Tyr Val
65                  70                  75

GTC TAC TTT GTG GTC TTT CCC TTC TTC TTC GTC AAC ATC                        271
Val Tyr Phe Val Val Phe Pro Phe Phe Phe Val Asn Ile
            80                  85                  90

TTT GTG GCT TTG ATC ATC ATC ACC TTC CAG GAG CAG GGG                        310
Phe Val Ala Leu Ile Ile Ile Thr Phe Gln Glu Gln Gly
                95                  100
```

-continued

| | |
|---|---|
| GAC AAG GTG ATG TCT GAA TGC AGC CTG GAG AAG AAC GAG<br>Aps Lys Val Met Ser Glu Cys Ser Leu Glu Lys Asn Glu<br>105                    110                    115 | 349 |
| AGG GCT TGC ATT GAC TTC GCC ATC AGC GCC AAA CCC CTG<br>Arg Ala Cys Ile Asp Phe Ala Ile Ser Ala Lys Pro Leu<br>              120                    125 | 388 |
| ACA CGG TAC ATG CCC CAA AAC CGG CAG TCG TTC CAG TAT<br>Thr Arg Tyr Met Pro Gln Asn Arg Gln Ser Phe Gln Tyr<br>130                    135                    140 | 427 |
| AAG ACG TGG ACA TTT GTG GTC NNC CCG CCC TTT GAA TAC<br>Lys Thr Trp Thr Phe Val Val Ser Pro Pro Phe Glu Tyr<br>              145                    150                    155 | 466 |
| TTC ATC ATG GCC ATG ATA GCC CTC AAC ACT GTG GTG CTG<br>Phe Ile Met Ala Met Ile Ala Leu Asn Thr Val Val Leu<br>                    160                    165 | 505 |
| ATG ATG AAG TTC TAC GAT GCA CCC TAT GAG TAC GAG CTG<br>Met Met Lys Phe Tyr Asp Ala Pro Tyr Glu Tyr Glu Leu<br>170                    175                    180 | 544 |
| ATG CTG AAA TGC CTG AAC ATC GTG TTC ACA TCC ATG TTC<br>Met Leu Lys Cys Leu Asn Ile Val Phe Thr Ser Met Phe<br>              185                    190 | 583 |
| TCC ATG GAA TGC GTG CTG AAG ATC ATC GCC TTT GGG GTG<br>Ser Met Glu Cys Val Leu Lys Ile Ile Ala Phe Gly Val<br>195                    200                    205 | 622 |
| CTG AAC TAT TTC AGA GAT GCC TGG AAT GTC TTT GAC TTT<br>Leu Asn Tyr Phe Arg Asp Ala Trp Asn Val Phe Asp Phe<br>              210                    215                    220 | 661 |
| GTC ACT GTG TTG GGA AGT ATT ACT GAT ATT TTA GTA ACA<br>Val Thr Val Leu Gly Ser Ile Thr Asp Ile Leu Val Thr<br>                    225                    230 | 700 |
| GAG ATT GCG AAC AAT TTC ATC AAC CTC AGC TTC CTC CGC<br>Glu Ile Ala Asn Asn Phe Ile Asn Leu Ser Phe Leu Arg<br>235                    240                    245 | 739 |
| CTC TTT CGA GCT GCG CGG CTG ATC AAG CTG CTC CGC CAG<br>Leu Phe Arg Ala Ala Arg Leu Ile Lys Leu Leu Arg Gln<br>              250                    255 | 778 |
| GGC TAC ACC ATC CGC ATC CTG CTG TGG ACC TTT GTC CAG<br>Gly Tyr Thr Ile Arg Ile Leu Leu Trp Thr Phe Val Gln<br>260                    265                    270 | 817 |
| TCC TTC AAG GCC CTG CCC TAC GTG TGT CTG CTC ATT GCC<br>Ser Phe Lys Ala Leu Pro Tyr Val Cys Leu Leu Ile Ala<br>              275                    280                    285 | 856 |
| ATG CTG TTC TTC ATC TAC GCC ATC ATC GGC ATG CAG GTG<br>Met Leu Phe Phe Ile Tyr Ala Ile Ile Gly Met Gln Val<br>                    290                    295 | 895 |
| TTT GGG AAT ATT GCC CTG GAT GAT GAC ACC AGC ATC AAC<br>Phe Gly Asn Ile Ala Leu Asp Asp Asp Thr Ser Ile Asn<br>300                    305                    310 | 934 |
| CGC CAC AAC AAC TTC CGG ACG TTT TTG CAA GCC CTG ATG<br>Arg His Asn Asn Phe Arg Thr Phe Leu Gln Ala Leu Met<br>              315                    320 | 973 |
| CTG CTG TTC AGG AGC GCC ACG GGG GAG GCC TGG CAC GAG<br>Leu Leu Phe Arg Ser Ala Thr Gly Glu Ala Trp His Glu<br>325                    330                    335 | 1012 |
| TCA TGC TGT CCT GCC TGAGCAACCA GGCCTGTGAT GAGCAGGCCA<br>Ser Cys Cys Pro Ala<br>              340 | 1057 |
| ATGCCACCGA GTGTGGAAGT GACTTTGCCT ACTTCTACTT | 1097 |

-continued

| | |
|---|---|
| CGTCTCCTTC ATCTTCCTGT GCTCCTTTCT GATGTTGAAC | 1137 |
| CTCTTTGTGG CTGTGATCAT GGACAATTTT GAGTACCTCA | 1177 |
| CGCGGGACTC TTCCATCCTA GGTCCTCACC ACTTGGATGA | 1217 |
| GTTCATCCGG GTCTGGGCTG AATACGACCC GGCTGCGTGT | 1257 |
| GGGCGCATCA GTTACAATGA CATGTTTGAG ATGCTGAAAC | 1297 |
| ACATGTCCCC GCCTCTGGGG CTGGGAAGA AATGCCCTGC | 1337 |
| TCGAGTTGCT TACAAGCGCC TGGTTCGCAT GAACATGCCC | 1377 |
| ATCTCCAACG AGGACATGAC TGTTCACTTC ACGTCCACGC | 1417 |
| TGATGGCCCT CATCCGGACG GCACTGGAGA TCAAGCTGGC | 1457 |
| CCCAGCTGGG ACAAAGCAGC ATCAGTGTGA CGCGGAGTTG | 1497 |
| AGGAAGGAGA TTTCCGTTGT GTGGGCCAAT CTGCCCCAGA | 1537 |
| AGACTTTGGA CTTGCTGGTA CCACCCCATA AGCCTGATGA | 1577 |
| GATGACAGTG GGGAAGGTTT ATGCAGCTCT GATGATATTC | 1617 |
| GACTTCTACA AGCAGAACAA AACCACCAGA GACCAGATGC | 1657 |
| AGCAGGCTCC TGGAGGCCTC TCCCAGATGG GTCCTGTGTC | 1697 |
| CCTGTTCCAC CCTCTGAAGG CCACCCTGGA GCAGACACAG | 1737 |
| CCGGCTGTGC TCCGAGGAGC CCGGGTTTTC CTTCGACAGA | 1777 |
| AGAGTTCCAC CTCCCTCAGC AATGGCGGGG CCATACAAAA | 1817 |
| CCAAGAGAGT GGCATCAAAG AGTCTGTCTC CTGGGGCACT | 1857 |
| CAAAGGACCC AGGANNCACC CCATGAGGCC AGGCCACCCC | 1897 |
| TGGAGCGTGG CCACTCCACA GAGATCCCTG TGGGGCGGTC | 1937 |
| AGGAGCACTG GCTGTGGACG TTCAGATGCA GAGCATAACC | 1977 |
| CGGAGGGNNC CTGATGGGGA GCCCCAGCCT GGGCTGGAGA | 2017 |
| GCCAGGGTCG AGCGGCCTCC ATGCCCCGCC TTGCGGCCGA | 2057 |
| GACTCAGCCC GTCACAGATG CCAGCCCCAT GAAGCGCTCC | 2097 |
| ATCTCCACGC TGGCCCAGCG GCCCCGTGGG ACTCATCTTT | 2137 |
| GCAGCACCAC CCCGGACCGC CCACCCCCTA GCCAGGCGTC | 2177 |
| GTCGCACCAC CACCACCACC GCTGCCACCG CCGCAGGGAC | 2217 |
| AGGAAGCAGA GGTCCCTGGA GAAGGGGCCC AGCCTGTCTG | 2257 |
| CCGATATGGA TGGCGCACCA AGCAGTGCTG TGGGGCCGGG | 2297 |
| GCTGCCCCCG GGAGAGGGGC CTACAGGCTG CCGGCGGGAA | 2337 |
| CGAGAGCGCC GGCAGGAGCG GAGCCGGTCC CAGGAGCGGA | 2377 |
| GGCAGCCCTC ATCCTCCTCC TCGGAGAAGC AGCGCTTCTA | 2417 |
| CTCCTGCGAC CGCTTTGGGG GCCGTGAGCC CCCGAAGCCC | 2457 |
| AAGCCCTCCC TCAGCAGCCA CCCAACGTCG CCAACAGCTG | 2497 |
| GCCAGGAGCC GGGACCCCAC CCACAGGGCA GTGGTTCCGT | 2537 |
| GAATGGGAGC CCCTTGCTGT CAACATCTGG TGCTAGCACC | 2577 |
| CCCGGCCGCG GTGGGCGGAG GCAGCTCCCC CAGACGCCCC | 2617 |
| TGACTCCCCG CCCCAGCATC ACCTACAAGA CGGCCAACTC | 2657 |
| CTCACCCATC CACTTCGCCG GGGCTCAGAC CAGCCTCCCT | 2697 |

```
GCCTTCTCCC CAGGCCGGCT CAGCCGTGGG CTTTCCGAAC            2737

ACAACGCCCT GCTGCAGAGA GACCCCCTCA GCCAGCCCCT            2777

GGCCCCTGGC TCTCGAATTG CTCTGACCC TTACCTGGGG             2817

CAGCGTCTGG ACAGTGAGGC CTCTGTCCAC GCCCTGCCTG            2857

AGGACACGCT CACTTTCGAG GAGGCTGTGG CCACCAACTC            2897

GGGCCGCTCC TCCAGGACTT CCTACGTGTC CTCCCTGACC            2937

TCCCAGTCTC ACCCTCTCCG CCGCGTGCCC AACGGTTACC            2977

ACTGCACCCT GGGACTCAGC TCGGGTGGCC GAGCACGGCA            3017

CAGCTACCAC CACCCTGACC AAGACCACTG GTGCTAGCTG            3057

CACCGTGACC GCTCAGACGC CTGCATGCAG CAGGCGTGTG            3097

TTCCAGTGGA TGAGTTTTAT CATCCACACG GGGCAGTCGG            3137

CCNTCGGGGG AGGCCTTGCC CACCTTGGTG AGGCTCCTGT            3177

GGCCCCTCCC TCCCCCTCCT CCCCTCTTTT ACTCTAGACG            3217

ACGAATAAAG CCCTGTTAGA GGATGCGGCT CTCTCTGTCC            3257

CCTTCCTGTC CTGCCTTCCT GGGNCTCGTA CCACACACCA            3297

GACCCTAAAC CGCAGGCTGC TGTGTGTGGC TGAGAAGGAC            3337

CCAGGAGTCC AAATCCCGTG TCCTGGGACT CAGCATCCAG            3377

CATGGGTGCT TGGAGCCGTT GTGAGGAGCT CTGCGTCCTG            3417

TGGGGAGCAC CCTTCACGTG GCCGTGCGGC ACAGAGAAGC            3457

AGGGCCCACC TGAAAGTGCG CCGAGACCTC GGGACGGAGG            3497

GGATGGGGAG GGGGACACAG TCGTGGCTTG TGCAGCCCGC            3537

CAGTGTCAGC GAATGCTCAC TCAGGCAAGC TCTGTCCTCC            3577

CTGGACACCG TCAGCCCCAC AGGAACCGAG CTGGGAAGTG            3617

TTCTTGCTGT GGTTGTGATT TTTAATTGCA ACACCTCTCA            3657

TTCTTGTCAC TTCTATATAC GTGATGTAGA AAAAATGGAA            3697

AACCAGAAAA ATGGGAAGG AAATGTTCAC ATAACTTTAA             3737

AAAATCAAAC CTGTGAAAGA AAGATGTCAG CTTTTTGCCA            3777

CGTGTCTTTG TGGCTTATGC GAGGANACTC CCTGTGCAGC            3817

CCTGTCCGGT CCAGGTGGAC GTAGATGGCC CCTGGCTCTG            3857

CTGCTCTTGA CCAAGTGCCT GACCGCCAGG CCCTCACACC            3897

CAGGCTCCTG GGCACTGTGG TGTGAGGCGA GGCCTCGGGA            3937

TCCATCACCG CAGGATGTTG TGAAAAGTAC TCGCGATGGC            3977

AGCCAGGTAG CAAGCCCTTG CCAGTGGAGA GCACTGGATG            4017

TCATGGTGGC AAACAAGGCA GCCATTTGCT GTCCTCCTCC            4057

CACGAGTGGA AGGGGTTTCC AAGGAAGCCA CAGGGCAGCT            4097

GACCACGTGC TTGTGTGAGG CATTTTCAGT CTGTTCTGCA            4137

TATGATTCTC AGGGCACACT CTGTGGTATG TGAAATAGGT            4177

TTCCTTCCAC ATACAGCAGA AGAGAGGCAA AGGCTGGTAG            4217

GAAGGAGGAA GACATTGGCT GGGGGCTTGG ATGTGGGGCC            4257
```

```
GTCAGGGCAG GAGGGAGGAN GCCCCAGCTG GAATGAAACT              4297

CAGAGCAAGT GACCGAGGGA GGACACGGCT CCTGCCACTG              4337

AGGCCGGGCA CCTGATGCCC AGCACTGTCC TGGCGCCAGA              4377

CACAGGGAGC AGGCAGTCAA GTGAGGTCTG ACCCCCATGG              4417

CCACNCTCAG GAGAGAAAGA CCATGCTCAG GACACTGTCC              4457

AAGGTGCACA AGATGCTGGG AGGTNCNTTG TTTGGTGAAG              4497

AAAGGGAGCA TTTAGAGCAG TTGATGGTGG TGTGTCCTCC              4537

GTGTTCTGAA ATTCCAGATG ATCTGTGTTG GATTTTTGNC              4577

TTCTACCCCA TNATTCTCCT CAAAGAAANN GTGTGTGATG              4617

TGTGTGTGTG TGTGTGTGTG TGTGTCTGTG TCACAGGAGA              4657

TGCAGTGCCT GTACAGGTGT GTTCAGTGTG TGNATGTCAT              4697

TAACCCATAG GGCTATGCAA CAAAAGACAC ATTTAATAGA              4737

AGTAAAACAC ACAAGACCGC TGCCTGGTCT CGGGGTTCAG              4777

CATGATTGTG ACCAAACCTT TTTATAGAAT TTCCTTACCT              4817

GAAGGCACAA CACTCTGAAA CTTTAAAGAT AACAGAGTAT              4857

TTTATTCCAA TAGNATAAAC CAGGAATCTC GNACTGTGCA              4897

TGTGATCACT GTGCTCCTGT TGCAAAGNAG AAGGATGTGT              4937

ATTTTGACAC TGACGTTTTG TCTCTTGTTC CCCAGCCCCC              4977

AGCCCATGTT ATCTTGGGTG TCGAATGTGT CCATTCCATG              5017

CAGAACCACA GCCATTTCCC CAGGCAGTGT TGGGTCGAGA              5057

ATCCACTTTT CTAAACCCAC ACAGCCTAGC TGGCTTGTCT              5097

AGACTCTTCT AGGCATTGGA ATTGATGAAA ACTACAGGGA              5137

GCGGGNAAAG GAGACATTAT GTCTTGTTTC CTGACTTTGG              5177

GTTTTGTTTC TCACTGTGTC TTCTCCGGCT ATCATATATG              5217

TCCCCTGAAT CTCATAGTGA GCTGCCAAAT TTGAAGTGCA              5257

TCACCCAGTT GTCTGCATCT GGAACCAGTC AAGCAGTGGC              5297

TGTAGTTTGA ACAAGTTATG TGTGCATGTA ACATATATAC              5337

ATATATACAT ATATACAAGT ATGTGCATGA TAATGTATAT              5377

CTTCGTACTT TTTGATACAA TGTATTCATT TGTTAATTTT              5417

TAATTATATT TGATATAAAT C                                  5438

(2) INFORMATION FOR SEQ ID NO: 6:

(i) SEQUENCE CHARACTERISTICS:
        (A) LENGTH: 1722 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:6:

G AAC GCA GAG GAA AAC TCC CGC ATC TCC ATC ACC TTC         37
  Asn Ala Glu Glu Asn Ser Arg Ile Ser Ile Thr Phe
  1               5                   10

TTC CGC CTG TTC CGG GTC ATG CGT CTG GTG AAG CTG CTG       76
Phe Arg Leu Phe Arg Val Met Arg Leu Val Lys Leu Leu
```

```
                        15                      20                          25
AGC CGT NNN GAG GGC ATC CGG ACG CTG CTG TGG ACC TTC                              115
Ser Arg Xaa Glu Gly Ile Arg Thr Leu Leu Trp Thr Phe
                                30              35

ATC AAG TCC TTC CAG GCC CTG CCC TAT NTG GCC CTC CTG                              154
Ile Lys Ser Phe Gln Ala Leu Pro Tyr Val Ala Leu Leu
        40                  45                  50

ATC GTG ATG CTG TTC TTC ATC TAC NCG GTG ATC GGG ATG                              193
Ile Val Met Leu Phe Phe Ile Tyr Ala Val Ile Gly Met
                55                  60

CAG GTG TTT GGG AAA ATT GCC CTG AAT GAT ACC ACA GAG                              232
Gln Val Phe Gly Lys Ile Ala Leu Asn Asp Thr Thr Glu
65              70                  75

ATC AAC CGG AAC AAC AAC TTT CAG ACC TNN NCC CAG GCC                              271
Ile Asn Arg Asn Asn Asn Phe Gln Thr Phe Pro Gln Ala
            80                  85                  90

GTG CTG CTC CTC TTC AGG TGT GCC ACC GGG GAG GCC TGG                              310
Val Leu Leu Leu Phe Arg Cys Ala Thr Gly Glu Ala Trp
                    95                  100

CAG GAC ATC ATG CTG GCC TGC ATG CCA GGC AAG AAG TGT                              349
Gln Asp Ile Met Leu Ala Cys Met Pro Gly Lys Lys Cys
        105                 110                 115

NNC CCA GAG TCC GAG CCC AGC AAC AGC ACG GAG GGT GAA                              388
Ala Pro Glu Ser Glu Pro Ser Asn Ser Thr Glu Gly Glu
                120                 125

ACA CCC TGT GGT AGC AGC TTT GCT GTC TTC TAC TTC ATC                              427
Thr Pro Cys Gly Ser Ser Phe Ala Val Phe Tyr Phe Ile
130             135                 140

AGC TTC TAC ATG CTC TGT GCC TTC CTG ATC ATC AAC CTC                              466
Ser Phe Tyr Met Leu Cys Ala Phe Leu Ile Ile Asn Leu
            145                 150                 155

TTT GTA GCT GTC ATC ATG GAC AAC TTT GAC TAC CTG ACA                              505
Phe Val Ala Val Ile Met Asp Asn Phe Asp Tyr Leu Thr
                160                 165

AGG GAC TGG TCC ATC CTT GGT CCC CAC CAC CTG GAT GAG                              544
Arg Asp Trp Ser Ile Leu Gly Pro His His Leu Asp Glu
        170                 175                 180

TTT AAA AGA ATC TGG GCA GAG TAT GAC CCT GAA GCC AAG                              583
Phe Lys Arg Ile Trp Ala Glu Tyr Asp Pro Glu Ala Lys
                185                 190

GGT CGT ATC AAA CAC CTG GAT GTG GTG ACC CTC CTC CNG                              622
Gly Arg Ile Lys His Leu Asp Val Val Thr Leu Leu Arg
195             200                 205

CGA ATT CAG CCG CCA CTA GGT TTT GGG AAG CTG TGC CCT                              661
Arg Ile Gln Pro Pro Leu Gly Phe Gly Lys Leu Cys Pro
            210                 215                 220

CAC CGC GTG GCT TGC AAA CGC CTG GTC TCC ATG AAC ATG                              700
His Arg Val Ala Cys Lys Arg Leu Val Ser Met Asn Met
                225                 230

CCT CTG AAC AGC GAC GGG ACA GTC ATG TTC AAT GCC ACC                              739
Pro Leu Asn Ser Asp Gly Thr Val Met Phe Asn Ala Thr
        235                 240                 245

CTG TTT GCC CTG GTC AGG ACG GCC CTG AGG ATC AAA ACA                              778
Leu Phe Ala Leu Val Arg Thr Ala Leu Arg Ile Lys Thr
                250                 255

GAA GGG AAC CTA GAA CAA GCC AAT GAG GAG CTG CGG GCG                              817
Glu Gly Asn Leu Glu Gln Ala Asn Glu Glu Leu Arg Ala
260                 265                 270

ATC ATC AAG AAG ATC TGG AAG CGG ACC AGC ANN AAG CTG                              856
```

-continued

```
                Ile Ile Lys Lys Ile Trp Lys Arg Thr Ser Met Lys Leu
                    275                 280                 285

CTG GAC CAG GTG GTG CCC CCT GCA GGT GAT GAT GAG GTC                                895
Leu Asp Gln Val Val Pro Pro Ala Gly Asp Asp Glu Val
            290                 295

ACC GTT GGC AAG TTC TAC GCC ACG TTC CTG ATC CAG GAG                                934
Thr Val Gly Lys Phe Tyr Ala Thr Phe Leu Ile Gln Glu
    300                 305                 310

TAC TTC CGG AAG TTC AAG AAG CGC AAA GAG CAG GGC CTT                                973
Tyr Phe Arg Lys Phe Lys Lys Arg Lys Glu Gln Gly Leu
                315                 320

GTG GNN AAG CCC TCC CAG AGG AAC GCG CTG TCT CTG CAG                               1012
Val Gly Lys Pro Ser Gln Arg Asn Ala Leu Ser Leu Gln
325                 330                 335

GCT GGN TTG CGC ACA CTG CAT GAC ATC GGG CCT GAG ATC                               1051
Ala Gly Leu Arg Thr Leu His Asp Ile Gly Pro Glu Ile
        340                 345                 350

CGA CGG GCC ATC TCT GGA GAT CTC ACC GCT GAG GAG GAG                               1090
Arg Arg Ala Ile Ser Gly Asp Leu Thr Ala Glu Glu Glu
                355                 360

CTG GAC AAG GCC ATG AAG GAG GCT GTG TCC GCT GCT TCT                               1129
Leu Asp Lys Ala Met Lys Glu Ala Val Ser Ala Ala Ser
            365                 370                 375

GAA GAT GAC ATC TTC AGG AGG GCC GGT NNN NTG TTC GGC                               1168
Glu Asp Asp Ile Phe Arg Arg Ala Gly Gly Leu Phe Gly
    380                 385

AAC CAC GTC AGc TAC TAC CAA AGC gAC GGC CGG ANN GCC                               1207
Asn His Val Ser Tyr Tyr Gln Ser Asp Gly Arg Xaa Ala
390                 395                 400

TTC CCC CAG ACC TTC ACC ACT CAG NGC CCG CTG CAC ATC                               1246
Phe Pro Gln Thr Phe Thr Thr Gln Xaa Pro Leu His Ile
        405                 410                 415

AAC AAG GCG GGC AGC AGC CAG GGC GAC ACT GAG TCG CNA                               1285
Asn Lys Ala Gly Ser Ser Gln Gly Asp Thr Glu Ser Xaa
                420                 425

TCC CAC GAG AAG CTG GTG GAC TCC ACC TTC ACC CCG AGC                               1324
Ser His Glu Lys Leu Val Asp Ser Thr Phe Thr Pro Ser
            430                 435                 440

AGC TAC TCG TCC ACC GGC TCC AAC GCC AAC ATC AAC AAC                               1363
Ser Tyr Ser Ser Thr Gly Ser Asn Ala Asn Ile Asn Asn
    445                 450

GCC AAC AAC ACC GCC CTG GGT CGC CTC CCT CNC NCC GCC                               1402
Ala Asn Asn Thr Ala Leu Gly Arg Leu Pro Xaa Xaa Ala
455                 460                 465

GGC TAC CCC AGC ACA GTC AGC ACT GTG GAG NCA CGG GCC                               1441
Gly Tyr Pro Ser Thr Val Ser Thr Val Glu Pro Arg Ala
        470                 475                 480

CCC CTT GTC CCC TGC CAT CCG GGT GCA GGA GGT GGN GTG                               1480
Pro Leu Val Pro Cys His Pro Gly Ala Gly Gly Gly Val
                485                 490

GAA GCT NAG CTC CAA CAG GTG CCA CTC CCG GGA GAG CCA                               1519
Glu Ala Gln Leu Gln Gln Val Pro Leu Pro Gly Glu Pro
            495                 500                 505

GGC AGC CAT GGC GGG TCA GGA GGA GAC GTC TCA GGA                                   1555
Gly Ser His Gly Gly Ser Gly Gly Asp Val Ser Gly
    510                 525

TGAGACCTAT GAAGTGAAGA TGAACCATGA CACGGAGGCC                                       1595

TGCAGTGAGC CCAGCCTGCT CTCCACAGAG ATGCTCTCCT                                       1635
```

```
ACCAGGATGA CGAAAATCGG CAACTGACGC TCCCAGAGGA              1675

GGACAAGAGG GACATCCGGC AATCTCCGAA GAGGGGTTTC              1715

CTCCGCT                                                  1722
```

(2) INFORMATION FOR SEQ ID NO: 7:

(i) SEQUENCE CHARACTERISTICS:
        (A) LENGTH: 2050 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:7:

```
GAG AAC AGC AAG TTT GAC TTT GAC AAT GTT CTG GCA GCC       39
Glu Asn Ser Lys Phe Asp Phe Asp Asn Val Leu Ala Ala
 1               5                  10

ATG ATG GCC CTC TTC ACC GTC TCC ACC TTC GAA GGG TGG       78
Met Met Ala Leu Phe Thr Val Ser Thr Phe Glu Gly Trp
     15                  20                  25

CCA GAG CTG CTG TAC CGC TCC ATC GAC TCC CAC ACG GAA      117
Pro Glu Leu Leu Tyr Arg Ser Ile Asp Ser His Thr Glu
                 30                  35

GAC AAG GNN CCC ATC TAC AAC TAC CGT GTG GAG ATC TCC      156
Asp Lys Gly Pro Ile Tyr Asn Tyr Arg Val Glu Ile Ser
 40                  45                  50

ATC TTC TTC ATC ATC TAC ATC ATC ATC GCC TTC TTC          195
Ile Phe Phe Ile Ile Tyr Ile Ile Ile Ala Phe Phe
             55                  60                  65

ATG ATG AAC ATC TTC GTG GGC TTC GTC ATC GTC ACC TTT      234
Met Met Asn Ile Phe Val Gly Phe Val Ile Val Thr Phe
                 70                  75

CAG GAG CAG GGG GAG CAG GAG TAC AAG AAC TGT GAG CTG      273
Gln Glu Gln Gly Glu Gln Glu Tyr Lys Asn Cys Glu Leu
 80                  85                  90

GAC AAG AAC CAG CGA CAG TGC GTG GAA TAC GCC CTC AAG      312
Asp Lys Asn Gln Arg Gln Cys Val Glu Tyr Ala Leu Lys
             95                  100

GCC CGG CCC CTG CGG AGG TAC ATN CCC AAG AAC CAG CAC      351
Ala Arg Pro Leu Arg Arg Tyr Ile Pro Lys Asn Gln His
105                  110                  115

CAG TAC AAA GTG TGG TAC GTG GTC AAC TCC ACC TAC TTC      390
Gln Tyr Lys Val Trp Tyr Val Val Asn Ser Thr Tyr Phe
             120                  125                  130

GAG TAC CTG ATG TTC GTC CTC ATC CTG CTC AAC ACC ATC      429
Glu Tyr Leu Met Phe Val Leu Ile Leu Leu Asn Thr Ile
                 135                  140

TGC CTG GCC ATG CAG CAC TAC GGC CAG AGC TGC CTG TTC      468
Cys Leu Ala Met Gln His Tyr Gly Gln Ser Cys Leu Phe
145                  150                  155

AAA ATC GCC ATG AAC ATC CTC AAC ATG CTC TTC ACT GGC      507
Lys Ile Ala Met Asn Ile Leu Asn Met Leu Phe Thr Gly
             160                  165

CTC TNC ACC GTG GAG ATG ATC CTG AAG CTC ATT GCC TTC      546
Leu Phe Thr Val Glu Met Ile Leu Lys Leu Ile Ala Phe
170                  175                  180

AAA CCC AAG CAC TAT TTC TGT GAT GCA TGG AAT ACA TTT      585
Lys Pro Lys His Tyr Phe Cys Asp Ala Trp Asn Thr Phe
             185                  190                  195
```

```
GAC GCC TTG ATT GTT GTG GGT AGC ATT GTT GAT ATA GCA        624
Asp Ala Leu Ile Val Val Gly Ser Ile Val Asp Ile Ala
            200                 205

ATC ACC GAG GTA AAC CCA GCT GAA CAT ACC CAA TGC TCT        663
Ile Thr Glu Val Asn Pro Ala Glu His Thr Gln Cys Ser
    210                 215                 220

CCC TCT ATG AAN NNA GAG GAA AAC TCC CGC ATC TCC ATC        702
Pro Ser Met Asn Ala Glu Glu Asn Ser Arg Ile Ser Ile
                225                 230

ACC TTC TTC CGC CTG TTC CGG GTC ATG CGT CTG GTG AAG        741
Thr Phe Phe Arg Leu Phe Arg Val Met Arg Leu Val Lys
235                 240                 245

CTG CTG AGC CGT GGG GAG GGC ATC CGG ACG CTG CTG TGG        780
Leu Leu Ser Arg Gly Glu Gly Ile Arg Thr Leu Leu Trp
        250                 255                 260

ACC TTC ATC AAG TCC TTC CAG GCC CTG CCC TAT GTG GCC        819
Thr Phe Ile Lys Ser Phe Gln Ala Leu Pro Tyr Val Ala
                265                 270

CTC CTG ATC GTG ATG CTG TTC TTC ATC TAC GCG GNG ATC        858
Leu Leu Ile Val Met Leu Phe Phe Ile Tyr Ala Val Ile
    275                 280                 285

GGG ATG CAG GTG TTT GGG AAA ATT GCN CTG AAT GNN ACC        897
Gly Met Gln Val Phe Gly Lys Ile Ala Leu Asn Asp Thr
            290                 295

ACA GAG AtN AAC CGG AAC AAC AAC TTT CAG ACC TNN NCC        936
Thr Glu Ile Asn Arg Asn Asn Asn Phe Gln Thr Phe Pro
300                 305                 310

CAG GCC GTG CTG CTC CTC TTC AGG TGT GCC ACC GGG GAG        975
Gln Ala Val Leu Leu Leu Phe Arg Cys Ala Thr Gly Glu
        315                 320                 325

GCC TGG CAG GAC ATC ATG CTG GCC TGC ATG CCA GGC AAG       1014
Ala Trp Gln Asp Ile Met Leu Ala Cys Met Pro Gly Lys
                330                 335

AAG TGT NNC CCA GAG TCC GAG CCC AGC AAC AGC ACG GAG       1053
Lys Cys Ala Pro Glu Ser Glu Pro Ser Asn Ser Thr Glu
    340                 345                 350

GGT GAA ACA CCC TGT GGT AGC AGC TTT GCT GTC TTC TAC       1092
Gly Glu Thr Pro Cys Gly Ser Ser Phe Ala Val Phe Tyr
            355                 360

TTC ATC AGC TTC TAC ATG CTC TGT GCC TTC CTG ATC ATC       1131
Phe Ile Ser Phe Tyr Met Leu Cys Ala Phe Leu Ile Ile
365                 370                 375

AAC CTC TTT GTA GCT GTC ATC ATG GAC AAC TTT GAC TAC       1170
Asn Leu Phe Val Ala Val Ile Met Asp Asn Phe Asp Tyr
        380                 385                 390

CTG ACA AGG GAC TGG TCC ATC CTT GGT CCC CAC CAC CTG       1209
Leu Thr Arg Asp Trp Ser Ile Leu Gly Pro His His Leu
                395                 400

GAT GAG TTT AAA AGA ATC TGG GCA GAG TAT GAC CCT GAA       1248
Asp Glu Phe Lys Arg Ile Trp Ala Glu Tyr Asp Pro Glu
    405                 410                 415

GCC AAG GGT CGT ATC AAA CAC CTG GAT GTG GTG ACC CTC       1287
Ala Lys Gly Arg Ile Lys His Leu Asp Val Val Thr Leu
            420                 425

CTC CGG CGG ATT CAG CCG CCA CTA GGT TTT NGG AAG CTG       1326
Leu Arg Arg Ile Gln Pro Pro Leu Gly Phe Gly Lys Leu
430                 435                 440

TGC CCT CAC CGC GTG GCT TGC AAA CGC CTG GTC TCC ATG       1365
Cys Pro His Arg Val Ala Cys Lys Arg Leu Val Ser Met
        445                 450                 455
```

```
AAC ATG CCT CTG AAC AGC GAC GGG ACA GTC ATG TTC AAT                        1404
Asn Met Pro Leu Asn Ser Asp Gly Thr Val Met Phe Asn
            460                 465

GCC ACC CTG TTT GCC CTG GTC AGG ACG GCC CTG AGG ATC                        1443
Ala Thr Leu Phe Ala Leu Val Arg Thr Ala Leu Arg Ile
    470                 475                 480

AAA ACA GAA GAG GGA CCC ANC CCA TCA GAG GCC CAC CAA                        1482
Lys Thr Glu Glu Gly Pro Xaa Pro Ser Glu Ala His Gln
                485                 490

GGG NCT GAG GAT CCT TTC CGC CCA GCA GGG AAC CTA GAA                        1521
Gly Ala Glu Asp Pro Phe Arg Pro Ala Gly Asn Leu Glu
495                 500                 505

CAA GCC AAT GAG GAG CTG CGG GCG ATC ATC AAG AAG ATC                        1560
Gln Ala Asn Glu Glu Leu Arg Ala Ile Ile Lys Lys Ile
        510                 515                 520

TGG AAG CGN ACC AGC ATG AAG CTG CTG GAC CAG GTG GTG                        1599
Trp Lys Arg Thr Ser Met Lys Leu Leu Asp Gln Val Val
                525                 530

CCC CCT GCA GGT GAT GAT GAG GTC ACC GTT GGC AAG TTC                        1638
Pro Pro Ala Gly Asp Asp Glu Val Thr Val Gly Lys Phe
    535                 540                 545

TAC GCC ACG TTC CTG ATC CAG GAG TAC TTC CGG AAG TTC                        1677
Tyr Ala Thr Phe Leu Ile Gln Glu Tyr Phe Arg Lys Phe
                550                 555

AAG AAG CGC AAA GAG CAG GGC CTT GTG GNC AAG CCC TCC                        1716
Lys Lys Arg Lys Glu Gln Gly Leu Val Gly Lys Pro Ser
560                 565                 570

CAG AGG AAC GCG CTG TCT CTG CAG GCT GGC TTG CGC ACA                        1755
Gln Arg Asn Ala Leu Ser Leu Gln Ala Gly Leu Arg Thr
        575                 580                 585

CTG CAT GAC ATC GGG CCT GAG ATC CGA CGG GNN ATC TCT                        1794
Leu His Asp Ile Gly Pro Glu Ile Arg Arg Ala Ile Ser
                590                 595

GGA GAT CTC ACC GNT GAG GAG GAG CTG GAC AAG GCC ATG                        1833
Gly Asp Leu Thr Ala Glu Glu Glu Leu Asp Lys Ala Met
    600                 605                 610

AAG GAG GCT GTG TCC GCT GCT TCT GAA GAT GAC ATC TTC                        1872
Lys Glu Ala Val Ser Ala Ala Ser Glu Asp Asp Ile Phe
                615                 620

AGG AGN NNC GGT GGC CTG TTC GGC AAC CAC GTC AGC TAC                        1911
Arg Arg Ala Gly Gly Leu Phe Gly Asn His Val Ser Tyr
625                 630                 635

TAC CAA AGC GAC GGC CGG AGC GCC TTC CNN NAG ACC TTC                        1950
Tyr Gln Ser Asp Gly Arg Ser Ala Phe Xaa Xaa Thr Phe
        640                 645                 650

ACC ACT CAG CGC CCG CTG CAC ATC AAC AAG GCG GGC AGC                        1989
Thr Thr Gln Arg Pro Leu His Ile Asn Lys Ala Gly Ser
                655                 660

AGC CAG GGC GAC ACT GAG TCG CCA TCC CAC GAG AAG CTG                        2028
Ser Gln Gly Asp Thr Glu Ser Pro Ser His Glu Lys Leu
    665                 670                 675

GTG GAC TCC ACC TTC ACC CCG A                                              2050
Val Asp Ser Thr Phe Thr Pro
            680

(2) INFORMATION FOR SEQ ID NO: 8:

(i) SEQUENCE CHARACTERISTICS:
        (A) LENGTH: 997 nucleotides
        (B) TYPE: Nucleotide
```

```
        (C) STRANDEDNESS:  Single
        (D) TOPOLOGY:  Linear (ii) MOLECULE TYPE:  cDNA (xi) SEQUENCE DESCRIPTION: SEQ ID NO:8:

G AAC ATC GTG TTC ACA TCC ATG TTC TCC ATG GAA TGC                37
  Asn Ile Val Phe Thr Ser Met Phe Ser Met Glu Cys
   1               5                  10

GTG CTN AAG ATC ATC GCC TTT GGG GTG NNN NNC TAT TTC               76
Val Leu Lys Ile Ile Ala Phe Gly Val Leu Asn Tyr Phe
         15                  20                  25

AGA NAT GCC TGN ANT GTC NTT AAC NNN GTC ACN GTG TTG              115
Arg Asp Ala Xaa Xaa Val Phe Asn Xaa Val Thr Val Leu
                30                  35

GGA AGT ATT ANT GAT ATT TTA GTA ACA GAG ATT GCG AAN              154
Gly Ser Ile Xaa Asp Ile Leu Val Thr Glu Ile Ala Xaa
         40                  45                  50

AAT TTC ATC AAC CTC AGN TTN CTC NGC NTC TTT CGA NNT              193
Asn Phe Ile Asn Leu Xaa Xaa Leu Arg Xaa Phe Arg Arg
                 55                  60

GNG NGG CTG ATC AAG NTc GTC CGN CAG GGC TAC ACC ATC              232
Xxx Xxx Leu Ile Lys Xxx Val Arg Gln Gly Tyr Thr Ile
 65              70                  75

CGC ATC CTG CTG TGG ACC TTT GTC CAG TCC TTC AAG GCC              271
Arg Ile Leu Leu Trp Thr Phe Val Gln Ser Phe Lys Ala
             80                  85                  90

CTG CCC TAC GTG TGT CTG CTC ATT GCC ATG CTG TTC TTC              310
Leu Pro Tyr Val Cys Leu Leu Ile Ala Met Leu Phe Phe
                 95                  100

ATC TAC GCC ATC ATC GGC ATG CAG GTG TTT GGG AAT ATT              349
Ile Tyr Ala Ile Ile Gly Met Gln Val Phe Gly Asn Ile
        105                  110                 115

GCC CTG GAT GAT GAC ACC ANC ATC AAC CNC CAC AAC AAC              388
Ala Leu Asp Asp Asp Thr Ser Ile Asn Arg His Asn Asn
                120                 125

TTC CGG ACG TTT TTG CAA GCC CTG ATG CTG CTG TTC AGG              427
Phe Arg Thr Phe Leu Gln Ala Leu Met Leu Leu Phe Arg
130                 135                 140

AGC GCC ACN GGG GAG GCC TGG CAC GAG ATC ATG CTG TCC              466
Ser Ala Thr Gly Glu Ala Trp His Glu Ile Met Leu Ser
         145                 150                 155

TGC CTG AGC AAC CAG GCC TGT GAT GAG CAG GCC AAT GCC              505
Cys Leu Ser Asn Gln Ala Cys Asp Glu Gln Ala Asn Ala
                 160                 165

ACC GAG TGT GGA AGT GAC TTT GCC TAC TTC TAC TTC GTC              544
Thr Glu Cys Gly Ser Asp Phe Ala Tyr Phe Tyr Phe Val
170                 175                 180

TCC TTC ATC TTC CTG TGC TCC TTT CTG ATG TTG AAC CTC              583
Ser Phe Ile Phe Leu Cys Ser Phe Leu Met Leu Asn Leu
             185                 190

TTT GTG GCT GTG ATC ATG GAC AAT TTT GAG TAC CTC ACG              622
Phe Val Ala Val Ile Met Asp Asn Phe Glu Tyr Leu Thr
195                 200                 205

CGG GAC TCT TCC ATC CTA GGT CCT CAC CAC TTG GAT GAG              661
Arg Asp Ser Ser Ile Leu Gly Pro His His Leu Asp Glu
         210                 215                 220

TTC ATC CGG GTC TGG GCT GAA TAC GAC CCG GCT GCG TGT              700
Phe Ile Arg Val Trp Ala Glu Tyr Asp Pro Ala Ala Cys
                 225                 230
```

```
GGG CGC ATC AGT TAC AAT GAC ATG TTT GAG ATG CTG AAA          739
Gly Arg Ile Ser Tyr Asn Asp Met Phe Glu Met Leu Lys
    235                 240                 245

CAC ATG TCC CCG CCT CTG GGG CTG GGG AAG AAA TGC CCT          778
His Met Ser Pro Pro Leu Gly Leu Gly Lys Lys Cys Pro
                250                 255

GCT CGA GTT GCT TAC AAG CGC CTG GTT CGC ATG AAC ATG          817
Ala Arg Val Ala Tyr Lys Arg Leu Val Arg Met Asn Met
260                 265                 270

CCC ATC TCC AAC GAG GAC ATG ACT GTT CAC TTC ACG TCC          856
Pro Ile Ser Asn Glu Asp Met Thr Val His Phe Thr Ser
        275                 280                 285

ACG CTG ATG GCC CTC ATC CGG ACG GCA CTG GAG ATC AAG          895
Thr Leu Met Ala Leu Ile Arg Thr Ala Leu Glu Ile Lys
                290                 295

CTG GCC CCA GCT GGN ACA AAG CAG CAT CAG TGT GAC GCG          934
Leu Ala Pro Ala Gly Thr Lys Gln His Gln Cys Asp Ala
300                 305                 310

GAG TTG AGG AAG GAG ATT TCC GTT GTG TGG GCC AAT CTG          973
Glu Leu Arg Lys Glu Ile Ser Val Val Trp Ala Asn Leu
        315                 320

CCC CAG AAG ACT TTG GAC TTG CTG                              997
Pro Gln Lys Thr Leu Asp Leu Leu
325                 330

(2) INFORMATION FOR SEQ ID NO: 9:

(i) SEQUENCE CHARACTERISTICS:
        (A) LENGTH: 1471 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:9:

CC TCT ATG AAC GCA GAG GAA AAC TCC CGC ATC TCC ATC           38
   Ser Met Asn Ala Glu Glu Asn Ser Arg Ile Ser Ile
   1               5                   10

ACC TTC TTC CGC CTG TTC CGG GTC ATG CGT CTG GTG AAG          77
Thr Phe Phe Arg Leu Phe Arg Val Met Arg Leu Val Lys
        15                  20                  25

CTG CTG AGC CGT GGG GAG GGC ATC CGG ACG CTG CTG TGG          116
Leu Leu Ser Arg Gly Glu Gly Ile Arg Thr Leu Leu Trp
                30                  35

ACC TTC ATC AAG TCC TTC CAG GCC CTG CCC TAT GTG GCC          155
Thr Phe Ile Lys Ser Phe Gln Ala Leu Pro Tyr Val Ala
40                  45                  50

CTC CTG ATC GTG ATG CTG TTC TTC ATC TAC GCG GNG ATC          194
Leu Leu Ile Val Met Leu Phe Phe Ile Tyr Ala Val Ile
        55                  60

GGG ATG CAG GTG TTT GGG AAA ATT NCC CTG AAT GAT ACC          233
Gly Met Gln Val Phe Gly Lys Ile Xaa Leu Asn Asp Thr
65                  70                  75

ACA GAG ATC AAC CGG AAC AAC AAC TTT CAG ACC TNN NCC          272
Thr Glu Ile Asn Arg Asn Asn Asn Phe Gln Thr Phe Pro
        80                  85                  90

CAG GCC GTG CTG CTC CTC TTC AGG TGT GCC ACC GGG GAG          311
Gln Ala Val Leu Leu Leu Phe Arg Cys Ala Thr Gly Glu
                95                  100

GCC TGG CAG GAC ATC ATG CTG GCC TGC ATG CCA GGC AAG          350
Ala Trp Gln Asp Ile Met Leu Ala Cys Met Pro Gly Lys
```

-continued

```
              105                 110                 115
AAG TGT NNC CCA GAG TCC GAG CCC AGC AAC AGC ACG GAG                    389
Lys Cys Ala Pro Glu Ser Glu Pro Ser Asn Ser Thr Glu
            120                 125

GGT GAA ACA CCC TGT GGT AGC AGC TTT GCT GTC TTC TAC                    428
Gly Glu Thr Pro Cys Gly Ser Ser Phe Ala Val Phe Tyr
130                 135                 140

TTC ATC AGC TTC TAC ATG CTC TGT GCC TTC CTG ATC ATC                    467
Phe Ile Ser Phe Tyr Met Leu Cys Ala Phe Leu Ile Ile
            145                 150                 155

AAC CTC TTT GTA GCT GTC ATC ATG GAC AAC TTT GAC TAC                    506
Asn Leu Phe Val Ala Val Ile Met Asp Asn Phe Asp Tyr
                160                 165

CTG ACA AGG GAC TGG TCC ATC CTT GGT CCC CAC CAC CTG                    545
Leu Thr Arg Asp Trp Ser Ile Leu Gly Pro His His Leu
    170                 175                 180

GAT GAG TTT AAA AGA ATC TGG GCA GAG TAT GAC CCT GAA                    584
Asp Glu Phe Lys Arg Ile Trp Ala Glu Tyr Asp Pro Glu
                185                 190

GCC AAG GGT CGT ATC AAA CAC CTG GAT GTG GTG ACC CTC                    623
Ala Lys Gly Arg Ile Lys His Leu Asp Val Val Thr Leu
195                 200                 205

CTC CGG CGG ATT CAG CCG CCA CTA GGT TTT NGG AAG CTG                    662
Leu Arg Arg Ile Gln Pro Pro Leu Gly Phe Gly Lys Leu
            210                 215                 220

TGC CCT CAC CGC GTG GCT TGC AAA CGC CTG GTC TCC ATG                    701
Cys Pro His Arg Val Ala Cys Lys Arg Leu Val Ser Met
                225                 230

AAC ATG CCT CTG AAC AGC GAC GGG ACA GTC ATG TTC AAT                    740
Asn Met Pro Leu Asn Ser Asp Gly Thr Val Met Phe Asn
    235                 240                 245

GCC ACC CTG TTT GCC CTG GTC AGG ACG GCC CTG AGG ATC                    779
Ala Thr Leu Phe Ala Leu Val Arg Thr Ala Leu Arg Ile
                250                 255

AAA ACA GAA GGG AAC CTA GAA CAA GCC AAT GAG GAG CTG                    818
Lys Thr Glu Gly Asn Leu Glu Gln Ala Asn Glu Glu Leu
260                 265                 270

CGG GCG ATC ATC AAG AAG ATC TGG AAG CGG ACC AGC ANN                    857
Arg Ala Ile Ile Lys Lys Ile Trp Lys Arg Thr Ser Met
            275                 280                 285

AAG CTG CTG GAC CAG GTG GTG CCC CCT GCA GGT GAT GAT                    896
Lys Leu Leu Asp Gln Val Val Pro Pro Ala Gly Asp Asp
                290                 295

GAG GTC ACC GTT GGC AAG TTC TAC GCC ACG TTC CTG ATC                    935
Glu Val Thr Val Gly Lys Phe Tyr Ala Thr Phe Leu Ile
    300                 305                 310

CAG GAG TAC TTC CGG AAG TTC AAG AAG CGC AAA GAG CAG                    974
Gln Glu Tyr Phe Arg Lys Phe Lys Lys Arg Lys Glu Gln
                315                 320

GGC CTT GTG GNN AAG CCC TCC CAG AGG AAC GCG CTG TCT                   1013
Gly Leu Val Gly Lys Pro Ser Gln Arg Asn Ala Leu Ser
325                 330                 335

CTG CAG GCT GGN TTG CGC ACA CTG CAT GAC ATC GGG CCT                   1052
Leu Gln Ala Gly Leu Arg Thr Leu His Asp Ile Gly Pro
            340                 345                 350

GAG ATC CGA CGG GCC ATC TCT GGA GAT CTC ACC GCT GAG                   1091
Glu Ile Arg Arg Ala Ile Ser Gly Asp Leu Thr Ala Glu
                355                 360

GAG GAG CTG GAC AAG GCC ATG AAG GAG GCT GTG TCC GCT                   1130
```

```
Glu Glu Leu Asp Lys Ala Met Lys Glu Ala Val Ser Ala
    365                 370                 375

GCT TCT GAA GAT GAC ATC TTC AGG AGG GCC GGT GGC CTG         1169
Ala Ser Glu Asp Asp Ile Phe Arg Arg Ala Gly Gly Leu
        380                 385

TTC GGC AAC CAC GTC AGC TAC TAC CAA AGC GAC GGC CGG         1208
Phe Gly Asn His Val Ser Tyr Tyr Gln Ser Asp Gly Arg
390                 395                 400

ANN GCC TTC CCC CAG ACC TTC ACC ACT CAG CNC CCG CTG         1247
Xaa Ala Phe Pro Gln Thr Phe Thr Thr Gln Xaa Pro Leu
        405                 410                 415

CAC ATC AAC AAG GCN GGC AGC AGC CAG GGC GAC ACT GAG         1286
His Ile Asn Lys Ala Gly Ser Ser Gln Gly Asp Thr Glu
                420                 425

TCG CCA TCC CAC GAG AAG CTG GTG GAC TCC ACC TTC ACC         1325
Ser Pro Ser His Glu Lys Leu Val Asp Ser Thr Phe Thr
    430                 435                 440

CCG AGC AGC TAC TCG TCC ACC GGC TCC AAC GCC AAC ATC         1364
Pro Ser Ser Tyr Ser Ser Thr Gly Ser Asn Ala Asn Ile
                445                 450

AAC AAC GCC AAC AAC ACC GCC CTG GGT CGC CTC CCT CNN         1403
Asn Asn Ala Asn Asn Thr Ala Leu Gly Arg Leu Pro Xaa
455                 460                 465

CCC GCC GGC TAC CCC AGC ACA GTC AGC ACT GTG GAN NCA         1442
Pro Ala Gly Tyr Pro Ser Thr Val Ser Thr Val Glu Pro
        470                 475                 480

CGG GCC CCC CTT GTC CCC TGC CAT CCG GG                      1471
Arg Ala Pro Leu Val Pro Cys His Pro
                485

(2) INFORMATION FOR SEQ ID NO: 10:

(i) SEQUENCE CHARACTERISTICS:
        (A) LENGTH:  2655 nucleotides
        (B) TYPE:  Nucleotide
        (C) STRANDEDNESS:  Single
        (D) TOPOLOGY:  Linear (ii) MOLECULE TYPE:  cDNA (xi) SEQUENCE DESCRIPTION: SEQ ID NO:10:

CTTTTTCCTT CTTGAGGAAT GGAGCTTCGC AGAGGTTGCA                  40

TTTAGATTCA ACAGTTCACA GCGGCGGGCT GCTGCTGCTG                  80

CCTCTCCGAA GAGCTCGCGG AGCTCCCCAG AGGCNGTGGT                 120

CCCCNTGCTT GTCTGGATGC GGCTCTGAGT CTCCGTGTGT                 160

CTTTCTGCTT GTTGCTGTGT GCGGGTGTTC GNCCGCGATC                 200

ACCTTTGTGT GTCTTCTNTC TGTTTAAACC TCAGG ATG                  238
                                       Met
                                        1

GCT CGC TTC GGG GAG GCG GNG GNC GCC AGG CCA GGG             274
Ala Arg Phe Gly Glu Ala Val Val Ala Arg Pro Gly
            5                   10

TCC GGC GAT GGA GAC TCG GAC CAG AGC AGG AAC CGG             310
Ser Gly Asp Gly Asp Ser Asp Gln Ser Arg Asn Arg
    15                  20                  25

CAA GGA ACC CCC GTG CCG GCC TCG GGG CAG GCG GCN             346
Gln Gly Thr Pro Val Pro Ala Ser Gly Gln Ala Ala
                30                  35

GCC TAC AAG CAG ACG AAA GCA CAG AGG GNG NNG ACT             382
```

-continued

```
                Ala Tyr Lys Gln Thr Lys Ala Gln Arg Ala Arg Thr
                         40                  45

ATG GNT TTG TAC AAC CCC ATT CCC GTC CGG CAG AAC                418
Met Ala Leu Tyr Asn Pro Ile Pro Val Arg Gln Asn
50                   55                  60

TGT TTC ACC GTC AAC AGA TCC CTG TTC ATC TTC GGA                454
Cys Phe Thr Val Asn Arg Ser Leu Phe Ile Phe Gly
             65                  70

GAA GAT AAN ATT GTC AGG AAA TAT GCC AAG AAG CTC                490
Glu Asp Asn Ile Val Arg Lys Tyr Ala Lys Lys Leu
        75                  80                  85

ATC GAT TGG CCG CCA TTT GAG TAC ATG                            517
Ile Asp Trp Pro Pro Phe Glu Tyr Met
                90

ATC CTG GCC ACC ATC ATT GCC AAC TGC ATC GTC CTG GCC            556
Ile Leu Ala Thr Ile Ile Ala Asn Cys Ile Val Leu Ala
95                  100                 105

CTG GAG CAG CAT CTT CCT GAG GAT GAC AAG ACC CCC ATG            595
Leu Glu Gln His Leu Pro Glu Asp Asp Lys Thr Pro Met
            110                 115                 120

TCC NGA AGA CTG GAG AAG ACA GAA CCT TAT TTC ATT GGG            634
Ser Arg Arg Leu Glu Lys Thr Glu Pro Tyr Phe Ile Gly
                125                 130

ATC TTT TGC TTT GAA GCT GGG ATC AAA ATT GTG GCC CTG            673
Ile Phe Cys Phe Glu Ala Gly Ile Lys Ile Val Ala Leu
135                 140                 145

GGG TTC ATC TTC CAT AAG GGC TCT TAC CTC CGC AAT GGC            712
Gly Phe Ile Phe His Lys Gly Ser Tyr Leu Arg Asn Gly
            150                 155

TGG AAT GTC ATG GAC TTC ATC GTG GTN CTC ANT NGC ATC            751
Trp Asn Val Met Asp Phe Ile Val Val Leu Ser Gly Ile
160                 165                 170

CTG GCC ACT GCA GGA ACC CAC TTC AAT ACT CAC GTG GAC            790
Leu Ala Thr Ala Gly Thr His Phe Asn Thr His Val Asp
            175                 180                 185

CTG AGG ACC CTC CGG GCT GTG CGT GTC CTG CGG CCT TTG            829
Leu Arg Thr Leu Arg Ala Val Arg Val Leu Arg Pro Leu
                190                 195

AAG CTC GTG TCA GGG ATA CNT AGC CTG CAG ATT GTG TTG            868
Lys Leu Val Ser Gly Ile Pro Ser Leu Gln Ile Val Leu
200                 205                 210

AAG TCc ATC ATG AAG GCC ATG GTA CCT CTT CTG CAG ATT            907
Lys Ser Ile Met Lys Ala Met Val Pro Leu Leu Gln Ile
            215                 220

GGC CTT CTg CTC TTC TTT NCC ATC CTG ATG TTT GCT ATC            946
Gly Leu Leu Leu Phe Phe Ala Ile Leu Met Phe Ala Ile
225                 230                 235

ATT GGT TTG GAG TTC TAC AGT GGC AAG TTA CAT CGA GCA            985
Ile Gly Leu Glu Phe Tyr Ser Gly Lys Leu His Arg Ala
            240                 245                 250

TGC TTC ATG AAC AAT TCA GGT ATT CTA GAA GGA TTT GAC            1024
Cys Phe Met Asn Asn Ser Gly Ile Leu Glu Gly Phe Asp
                255                 260

CCC CCT CAC CCA TGT GGT GTG CAG GGC TGC CCA GCT GGT            1063
Pro Pro His Pro Cys Gly Val Gln Gly Cys Pro Ala Gly
265                 270                 275

TAT GAA TGC AAG GAC TGG ATC GGC CCC AAT GAT GGG ATC            1102
Tyr Glu Cys Lys Asp Trp Ile Gly Pro Asn Asp Gly Ile
            280                 285
```

```
ACC CAG TTT GAT AAC ATC CTT TTT GCT GTG CTG ACT GTC        1141
Thr Gln Phe Asp Asn Ile Leu Phe Ala Val Leu Thr Val
290                 295                 300

TTC CAG TGC ATC ACC ATG GAA GGG TGG ACC ACT GTG CTG        1180
Phe Gln Cys Ile Thr Met Glu Gly Trp Thr Thr Val Leu
        305                 310                 315

TAC AAT ACC AAT GAT GCC TTA GGA GCC ACC TGG AAT TGG        1219
Tyr Asn Thr Asn Asp Ala Leu Gly Ala Thr Trp Asn Trp
                320                 325

CTG TAC TTC ATC CCC CTC ATC ATC ATT GGA TCC TTC TTT        1258
Leu Tyr Phe Ile Pro Leu Ile Ile Ile Gly Ser Phe Phe
    330                 335                 340

GTT CTC AAC CTA GTC CTG GGA GTG CTT TCC GGG GAA TTT        1297
Val Leu Asn Leu Val Leu Gly Val Leu Ser Gly Glu Phe
            345                 350

GCC AAA GAG AGA GAG AGA GTG GAG AAC CGA AGG GCT TTC        1336
Ala Lys Glu Arg Glu Arg Val Glu Asn Arg Arg Ala Phe
355                 360                 365

ATN AAG CTG CGG CGC CAG CAG CAG ATT GAG CGT GAG CTG        1375
Met Lys Leu Arg Arg Gln Gln Gln Ile Glu Arg Glu Leu
        370                 375                 380

AAT GGC TAC CGT GCC TGG ATA GAC AAA GCA GAG GAA GTC        1414
Asn Gly Tyr Arg Ala Trp Ile Asp Lys Ala Glu Glu Val
                385                 390

ATG CTC GCT GAA GAA AAT AAA AAT GCT GGA ACA TCC GCC        1453
Met Leu Ala Glu Glu Asn Lys Asn Ala Gly Thr Ser Ala
395                 400                 405

TTA GAA GTG CTT CGA AGG GCA ACC ATC AAG AGG AGC CGG        1492
Leu Glu Val Leu Arg Arg Ala Thr Ile Lys Arg Ser Arg
            410                 415

ACA GAG GCC ATG ACT CGA GAC TCC AGT GAT GAG CAC TGT        1531
Thr Glu Ala Met Thr Arg Asp Ser Ser Asp Glu His Cys
420                 425                 430

GTT GAT ATC TCC TCT GTG GGC ACA CCT CTG GCC CGA GCC        1570
Val Asp Ile Ser Ser Val Gly Thr Pro Leu Ala Arg Ala
        435                 440                 445

AGT ATC AAA AGT GCA AAG GTA GAC GGG GTC TCT TAT TTC        1609
Ser Ile Lys Ser Ala Lys Val Asp Gly Val Ser Tyr Phe
                450                 455

CGG CAC AAG GAA AGG CTT CTG CGC ATC TCC ATT CGC CAC        1648
Arg His Lys Glu Arg Leu Leu Arg Ile Ser Ile Arg His
460                 465                 470

ATG GTT AAA TCC CAG GTG TTT TAC TGG ATT GTG CTG AGC        1687
Met Val Lys Ser Gln Val Phe Tyr Trp Ile Val Leu Ser
        475                 480

CTT GTG GCA CTC AAC ACT GCC TGT GTG GCC ATT GTC CAT        1726
Leu Val Ala Leu Asn Thr Ala Cys Val Ala Ile Val His
485                 490                 495

CAC AAC CAG CCC CAG TGG CTC ACC CAC CTC CTC TAC TAT        1765
His Asn Gln Pro Gln Trp Leu Thr His Leu Leu Tyr Tyr
            500                 505                 510

GCA GAA TTT CTG TTT CTG GGA CTC TTC CTC TTG GAG ATG        1804
Ala Glu Phe Leu Phe Leu Gly Leu Phe Leu Leu Glu Met
                515                 520

TCC CTG AAG ATG TAT GGC ATG GGG CCT CGC CTT TAT TTT        1843
Ser Leu Lys Met Tyr Gly Met Gly Pro Arg Leu Tyr Phe
525                 530                 535

CAC TCT TCA TTC AAC TGC TTT GAT TTT GGG GTC ACA GTG        1882
His Ser Ser Phe Asn Cys Phe Asp Phe Gly Val Thr Val
            540                 545
```

-continued

```
GGC AGT ATC TTT GAA GTG GTC TGG GCA ATC TTC AGA CCT          1921
Gly Ser Ile Phe Glu Val Val Trp Ala Ile Phe Arg Pro
550             555                 560

GGT ACG TCT TTT GGA ATC AGT GTC TTG CGA GCC CTC CGG          1960
Gly Thr Ser Phe Gly Ile Ser Val Leu Arg Ala Leu Arg
        565                 570                 575

CTT CTA AGA ATA TTT AAA ATA ACC AAG TAT TGG GCT TCC          1999
Leu Leu Arg Ile Phe Lys Ile Thr Lys Tyr Trp Ala Ser
                580                 585

CTA CGG AAT TTG GTG GTC TCC TTG ATG AGC TCA ATG AAG          2038
Leu Arg Asn Leu Val Val Ser Leu Met Ser Ser Met Lys
590                 595                 600

TCT ATC ATC AGT TTG CTT TTC CTC CTC TTC CTC TTC ATC          2077
Ser Ile Ile Ser Leu Leu Phe Leu Leu Phe Leu Phe Ile
        605                 610

GTT GTC TTT GCT CTC CTA GGA ATG CAG TTA TTT GGA GGC          2116
Val Val Phe Ala Leu Leu Gly Met Gln Leu Phe Gly Gly
615                 620                 625

AGG TTT AAC TTT AAT GAT GGG ACT CCT TCG GCA AAT TTT          2155
Arg Phe Asn Phe Asn Asp Gly Thr Pro Ser Ala Asn Phe
        630                 635                 640

GAT ACC TTC CCT GCA GCC ATC ATG ACT GTG TTC CAG ATC          2194
Asp Thr Phe Pro Ala Ala Ile Met Thr Val Phe Gln Ile
                645                 650

CTG ACG GGT GAG GAC TGG AAT GAG GTG ATG TAC AAT GGG          2233
Leu Thr Gly Glu Asp Trp Asn Glu Val Met Tyr Asn Gly
        655                 660                 665

ATC CGC TCC CAG GGT GGG GTC AGC TCA GGC ATG TGG TCT          2272
Ile Arg Ser Gln Gly Gly Val Ser Ser Gly Met Trp Ser
                670                 675

GCC ATC TAC TTC ATT GTG CTC ACC TTG TTT GGC AAC TAC          2311
Ala Ile Tyr Phe Ile Val Leu Thr Leu Phe Gly Asn Tyr
680                 685                 690

ACG CTA CTG AAT GTG TTC TTG GCT ATC GCT GTG GAT AAT          2350
Thr Leu Leu Asn Val Phe Leu Ala Ile Ala Val Asp Asn
        695                 700                 705

CTC GCC AAC GCC CAG GAA CTG ACC AAG GAT GAA CAG GAG          2389
Leu ala Asn Ala Gln Glu Leu Thr Lys Asp Glu Gln Glu
                710                 715

GAA GAA GAG GCC TTC AAC CAG AAA CAT GCA CTG CAG AAG          2428
Glu Glu Glu Ala Phe Asn Gln Lys His Ala Leu Gln Lys
720                 725                 730

GCC AAG GAG GTC AGC CCG ATG TCT GCA CCC AAC ATG CCT          2467
Ala Lys Glu Val Ser Pro Met Ser Ala Pro Asn Met Pro
        735                 740

TCG ATC GAA AGA GAC AGA AGG AGA AGA CAC CAC ATG TCG          2506
Ser Ile Glu Arg Asp Arg Arg Arg Arg His His Met Ser
745                 750                 755

ATG TGG GAG CCA CGC AGC AGC CAC CTG AGG GAG CGG AGG          2545
Met Trp Glu Pro Arg Ser Ser His Leu Arg Glu Arg Arg
        760                 765                 770

CGC CGG CAC CAC ATG TCC GTG TGG GAG CAG CGT ACC AGC          2584
Arg Arg His His Met Ser Val Trp Glu Gln Arg Thr Ser
                775                 780

CAG CTG AGG AAG CAC ATG CAG ATG TCC AGC CAG GAG GCC          2623
Gln Leu Arg Lys His Met Gln Met Ser Ser Gln Glu Ala
        785                 790                 795

CTC AAC AGA GAG GAG GCG CCG ACC ATG AGC CC                   2655
Leu Asn Arg Glu Glu Ala Pro Thr Met Ser
```

-continued

```
                  800                 805
```

(2) INFORMATION FOR SEQ ID NO: 11:

(i) SEQUENCE CHARACTERISTICS:
        (A) LENGTH: 6232 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:11:

```
TCCGCCTCTC GGGTTCAGGC AATTCTCCTG CCTCAGCCTC                              40

CCGAGTAGCT GGGACTATAG GTGCTCACCA CCATGCCTGG                              80

CTGATTTTTG TATTTTTAGT AGAGACAGGG TCTCCTCATG                             120

TTGGCCAGGT TGGTCTGAAA TTCCTGACCT CAGGTGCTCC                             160

ACCCACCTTG GCNTCCCAAA GTCCTGGGAT TACAGGCGTG                             200

AGTCACTGCA CTGGCTTTTT TTTTTTTTTT AAGACAGAGT                             240

TTTGCTTATG CG GAG GAG AAG TCC CCT TTG GAC GTG                          276
              Glu Glu Lys Ser Pro Leu Asp Val
              1               5

CTG AAG AGA GCG GCC ACC AAG AAG AGC AGA AAT GAC CTG                    315
Leu Lys Arg Ala Ala Thr Lys Lys Ser Arg Asn Asp Leu
    10              15                  20

ATC CAC GCA GAG GAG GGA GAG GAC CGG TTT GCA GAT CTC                    354
Ile His Ala Glu Glu Gly Glu Asp Arg Phe Ala Asp Leu
            25                  30

TGT GCT GTT GGA TCC CCC TTC GCC NGC GCC AGC CTC AAG                    393
Cys Ala Val Gly Ser Pro Phe Ala Arg Ala Ser Leu Lys
35              40                  45

AGC GGG AAG ACA GAG AGC TCG TCA TAC TTC CGG AGG AAG                    432
Ser Gly Lys Thr Glu Ser Ser Ser Tyr Phe Arg Arg Lys
        50              55                  60

GAG AAG ATG TTC CGG TTT TTT ATC CGG CGC ATG GTG AAG                    471
Glu Lys Met Phe Arg Phe Phe Ile Arg Arg Met Val Lys
                65                  70

GCT CAG AGC TTC TAC TGG GTG GTG CTG TGC GTG GTG GCC                    510
Ala Gln Ser Phe Tyr Trp Val Val Leu Cys Val Val Ala
    75              80                  85

CTG AAC ACA CTG TGT GTG GCC ATG GTG CAT TAC AAC CAG                    549
Leu Asn Thr Leu Cys Val Ala Met Val His Tyr Asn Gln
            90                  95

CCG CGG CGG CTT ACC ACG ACC CTG TAT TTT GCA GAG TTT                    588
Pro Arg Arg Leu Thr Thr Thr Leu Tyr Phe Ala Glu Phe
100             105                 110

GTT TTC CTG GGT CTC TTC CTC ACA GAG ATG TCC CTG AAG                    627
Val Phe Leu Gly Leu Phe Leu Thr Glu Met Ser Leu Lys
        115                 120                 125

ATG TAT GGC CTG GGG CCC AGA AGC TAC TTC CGG TCC TCC                    666
Met Tyr Gly Leu Gly Pro Arg Ser Tyr Phe Arg Ser Ser
                130                 135

TTC AAC TGC TTC GAC TTT GGG GTC ATC GTG GGG AGC GTC                    705
Phe Asn Cys Phe Asp Phe Gly Val Ile Val Gly Ser Val
    140                 145                 150

TTT GAA GTG GTC TGG GCG GCC ATC AAG CCG GGA AGC TCC                    744
Phe Glu Val Val Trp Ala Ala Ile Lys Pro Gly Ser Ser
            155                 160
```

| | |
|---|---|
| TTT GGG ATC AGT GTG CTN CNG GCC CTC CGC CTG CTG AGG<br>Phe Gly Ile Ser Val Leu Arg Ala Leu Arg Leu Leu Arg<br>165                 170                     175 | 783 |
| ATC TTC AAA GTC ACG AAG TAC TGG AGC TCC CTG CGG AAC<br>Ile Phe Lys Val Thr Lys Tyr Trp Ser Ser Leu Arg Asn<br>        180                     185                     190 | 822 |
| CTG GTG GTG TCC CTG CTG AAC TCC ATG AAG TCC ATC ATC<br>Leu Val Val Ser Leu Leu Asn Ser Met Lys Ser Ile Ile<br>               195                     200 | 861 |
| AGC CTG CTC TTC TTG CTC TTC CTG TTC ATT GTG GTC TTC<br>Ser Leu Leu Phe Leu Leu Phe Leu Phe Ile Val Val Phe<br>205                 210                     215 | 900 |
| GCC CTG CTG GGG ATG CAG CTG TTT GGG GGA CAG TTC AAC<br>Ala Leu Leu Gly Met Gln Leu Phe Gly Gly Gln Phe Asn<br>        220                     225 | 939 |
| TTC CAG GAT GAG ACT CCC ACA ACC AAC TTC GAC ACC TTC<br>Phe Gln Asp Glu Thr Pro Thr Thr Asn Phe Asp Thr Phe<br>230                 235                     240 | 978 |
| CCT GCC GCC ATC CTC ACT GTC TTC CAG ATC CTG ACG GGA<br>Pro Ala Ala Ile Leu Thr Val Phe Gln Ile Leu Thr Gly<br>        245                     250                     255 | 1017 |
| GAG GAC TGG AAT GCA GTG ATG TAT CAC GGG ATC GAA TCG<br>Glu Asp Trp Asn Ala Val Met Tyr His Gly Ile Glu Ser<br>               260                     265 | 1056 |
| CAA GGC GGC GTC AGC AAA GGC ATG TTC TCG TCC TTN TAC<br>Gln Gly Gly Val Ser Lys Gly Met Phe Ser Ser Phe Tyr<br>270                 275                     280 | 1095 |
| TTC ATT GTC CTG ACA CTG TTC GGA AAC TAC ACT CTG CTG<br>Phe Ile Val Leu Thr Leu Phe Gly Asn Tyr Thr Leu Leu<br>               285                     290 | 1134 |
| AAN GTC TTT CTG GCC ATC GCT GTG GAC AAC CTG GCC AAC<br>Asn Val Phe Leu Ala Ile Ala Val Asp Asn Leu Ala Asn<br>295                 300                     305 | 1173 |
| GCC CAA GAG CTG ACC AAG GAT GAA GAG GAG ATG GAA GAA<br>Ala Gln Glu Leu Thr Lys Asp Glu Glu Glu Met Glu Glu<br>        310                     315                     320 | 1212 |
| GCA GCC AAT CAG AAG CTT GCT CTG CAA AAG GCC AAA GAA<br>Ala Ala Asn Gln Lys Leu Ala Leu Gln Lys Ala Lys Glu<br>               325                     330 | 1251 |
| GTG GCT GAA GTC AGC CCC ATG TCT GCC GCG AAC ATC TCC<br>Val Ala Glu Val Ser Pro Met Ser Ala Ala Asn Ile Ser<br>335                 340                     345 | 1290 |
| ATC GCC GCG CAG CAG AAC TCG GCC AAG GCG CGC TCG GTG<br>Ile Ala Ala Gln Gln Asn Ser Ala Lys Ala Arg Ser Val<br>        350                     355 | 1329 |
| TGG GAG CAG CGG GCC AGC CAG CTA CGG CTG CAG AAC CTG<br>Trp Glu Gln Arg Ala Ser Gln Leu Arg Leu Gln Asn Leu<br>360                 365                     370 | 1368 |
| CGG GCC AGC TGC GAG GCG CTG TAC AGC GAG ATG GAC CCC<br>Arg Ala Ser Cys Glu Ala Leu Tyr Ser Glu Met Asp Pro<br>               375                     380                     385 | 1407 |
| GAG NAG CGG CTG CGC TTC GCC ACT ACG CGC CAC CTG CGG<br>Glu Glu Arg Leu Arg Phe Ala Thr Thr Arg His Leu Arg<br>               390                     395 | 1446 |
| CCC GAC ATG AAG ACG CAC CTG GAC CGG CCG CTG GTG GTG<br>Pro Asp Met Lys Thr His Leu Asp Arg Pro Leu Val Val<br>400                 405                     410 | 1485 |
| GAG CTG GGC CGC GAC GGN GCG CGG GGG CCC GTG GGA GGC<br>Glu Leu Gly Arg Asp Gly Ala Arg Gly Pro Val Gly Gly<br>        415                     420 | 1524 |

```
AAA GCC CGA CCT GAG GCT GCG GAG GCC CCC GAG GGC GTC           1563
Lys Ala Arg Pro Glu Ala Ala Glu Ala Pro Glu Gly Val
425                 430                 435

GAC CCT CCG CGC AGG CAC CAC CGG CAC CGC GAC AAG GAC           1602
Asp Pro Pro Arg Arg His His Arg His Arg Asp Lys Asp
        440                 445                 450

AAG ACC CCC GCG GCG GGG GAC CAG GAC CGA GCA GAG GCC           1641
Lys Thr Pro Ala Ala Gly Asp Gln Asp Arg Ala Glu Ala
                455                 460

CCG AAG GCG GAG AGC GGG GAG CCC GGT GCC CGG GAG GAG           1680
Pro Lys Ala Glu Ser Gly Glu Pro Gly Ala Arg Glu Glu
465                 470                 475

CGG CCG CGG CCG CAC CGC AGC CAC AGC AAG GAG GCC GCG           1719
Arg Pro Arg Pro Asp Arg Ser His Ser Lys Glu Ala Ala
        480                 485

GGG CCC CCG GAG GCG CGG AGC AGC GCC GGC CGA GGC CCA           1758
Gly Pro Pro Glu Ala Arg Ser Glu Arg Gly Arg Gly Pro
490                 495                 500

GGC CCC GAG GGC GGC CGG CGG CAC CAC CGG CGC GGC TCC           1797
Gly Pro Glu Gly Gly Arg Arg His His Arg Arg Gly Ser
        505                 510                 515

CCG GAG GAG GCG GCC GAG CGG GAG CCC CGA CGC CAC CGC           1836
Pro Glu Glu Ala Ala Glu Arg Glu Pro Arg Arg His Arg
                520                 525

GCG CAC CGG CAC CAG GAT CCG AGC AAG GAG TGC GCC GGC           1875
Ala His Arg His Gln Asp Pro Ser Lys Glu Cys Ala Gly
530                 535                 540

GCC AAG GGC GAG CGG NGN GCG CGG CAC CGC GGC GGC CCC           1914
Ala Lys Gly Glu Arg Arg Ala Arg His Arg Gly Gly Pro
        545                 550

CGA GCG GGG CCC CGG GAG GCG GAG AGC GGG GAG GAG CCG           1953
Arg Ala Gly Pro Arg Glu Ala Glu Ser Gly Glu Glu Pro
555                 560                 565

GCG CGG CGG CAC CGG GCC CGG CAC AAG GCG CAG CCT GCT           1992
Ala Arg Arg His Arg Ala Arg His Lys Ala Gln Pro Ala
        570                 575                 580

CAC GAG GCT GTG GAG AAG GAG ACC ACN GAG AAG GAG GCC           2031
His Glu Ala Val Glu Lys Glu Thr Thr Glu Lys Glu Ala
                585                 590

ACG GAG AAG GAG GCT GAG ATA GTG GAA GCC GAC AAG GAA           2070
Thr Glu Lys Glu Ala Glu Ile Val Glu Ala Asp Lys Glu
595                 600                 605

AAG GAG CTC CGG AAC CAC CAG CCC CGG GAG CCA CAC TGT           2109
Lys Glu Leu Arg Asn His Gln Pro Arg Glu Pro His Cys
        610                 615

GAC CTG GAG ACC AGT GGG ACT GTG ACT GTG GGT CCC ATG           2148
Asp Leu Glu Thr Ser Gly Thr Val Thr Val Gly Pro Met
620                 625                 630

CAC ACA CTG CCC AGC ACC TGT CTC CAG AAG GTG GAG AAA           2187
His Thr Leu Pro Ser Thr Cys Leu Gln Lys Val Glu Glu
        635                 640                 645

CAG CCA GAG GAT GCA GAC AAT CAG CGG AAC GTC ACT CGC           2226
Gln Pro Glu Asp Ala Asp Asn Gln Arg Asn Val Thr Arg
                650                 655

ATG GGC AGT CAG CCC CCA GAC CCG AAC ACT ATT GTA CAT           2265
Met Gly Ser Gln Pro Pro Asp Pro Asn Thr Ile Val His
660                 665                 670

ATC CCA GTG ATG CTG ACG GGC CCT CTT GGG GAA GCC ACG           2304
Ile Pro Val Met Leu Thr Gly Pro Leu Gly Glu Ala Thr
```

-continued

```
                675                 680
GTC GTT CCC AGT GGT AAC GTG GAC CTG GAA AGC CAA GCA           2343
Val Val Pro Ser Gly Asn Val Asp Leu Glu Ser Gln Ala
685                 690                 695

GAG GGG AAG AAG GAG GTG GAA GCG GAT GAC GTG ATG AGG           2382
Glu Gly Lys Lys Glu Val Glu Ala Asp Asp Val Met Arg
        700                 705                 710

AGC GGC CCC CGG CCT ATC GTC CCA TAC AGC TCC ATG TTC           2421
Ser Gly Pro Arg Pro Ile Val Pro Tyr Ser Ser Met Phe
                715                 720

TGT TTA AGC CCC ACC AAC CTG NTC CGC CGC TTC TGC CAC           2460
Cys Leu Ser Pro Thr Asn Leu Leu Arg Arg Phe Cys His
725                 730                 735

TAC ATC GTG ACC ATG AGG TAC TTC GAG GTG GTC ATT CTC           2499
Tyr Ile Val Thr Met Arg Tyr Phe Glu Val Val Ile Leu
        740                 745

GTG GTC ATC GCC TTG AGC AGC ATC GCC CTG GCT GCT GAG           2538
Val Val Ile Ala Leu Ser Ser Ile Ala Leu Ala Ala Glu
750                 755                 760

GAN CCA GTG CGC ACA GAC TCG CCC AGG AAC AAN GCT CTG           2577
Asp Pro Val Arg Thr Asp Ser Pro Arg Asn Asn Ala Leu
        765                 770                 775

ANA TAC CTG GAN TAC ATT TTC ACT GGT GTC TTT ACC TTT           2616
Lys Tyr Leu Asp Tyr Ile Phe Thr Gly Val Phe Thr Phe
                780                 785

GAG ATG GTG ATA AAG ATG ATC GAC TTG GGA CTG CTG CTT           2655
Glu Met Val Ile Lys Met Ile Asp Leu Gly Leu Leu Leu
790                 795                 800

CAC CCT GGA GCC TAT TTC CGG GAC TTG TGG AAC ATT CTG           2694
His Pro Gly Ala Tyr Phe Arg Asp Leu Trp Asn Ile Leu
        805                 810

GAC TTC ATT GTG GTC AGT GGC GNC CTG GTG GCG TTT GCN           2733
Asp Phe Ile Val Val Ser Gly Ala Leu Val Ala Phe Ala
815                 820                 825

TTC TCA GGA TCC AAA GGG NAA GAC ATC AAT ACC ATC AAG           2772
Phe Ser Gly Ser Lys Gly Lys Asp Ile Asn Thr Ile Lys
        830                 835                 840

TCT CTG AGA GTC CTT CGT GTN CTG CGG CCC CTC AAG ACC           2811
Ser Leu Arg Val Leu Arg Val Leu Arg Pro Leu Lys Thr
                845                 850

ATC AAA CGG CTG CCC AAG CTC AAG GCT GTG TTT GAC TGT           2850
Ile Lys Arg Leu Pro Lys Leu Lys Ala Val Phe Asp Cys
855                 860                 865

GTG GTG AAC TCC CTG AAG AAT GTC CTC AAC ATC TTG ATT           2889
Val Val Asn Ser Leu Lys Asn Val Leu Asn Ile Leu Ile
        870                 875

GTC TAC ATG CTC TTC ATG TTC ATA TTT GCC GTC ATT GCG           2928
Val Tyr Met Leu Phe Met Phe Ile Phe Ala Val Ile Ala
880                 885                 890

GTG CAG CTC TTC AAA GGG AAG TTT TTC TAC TGC ACA GAT           2967
Val Gln Leu Phe Lys Gly Lys Phe Phe Tyr Cys Thr Asp
        895                 900                 905

GAA TCC AAG GAG CTG GAG AGG GAC TGC AGG GGT CAG TAT           3006
Glu Ser Lys Glu Leu Glu Arg Asp Cys Arg Gly Gln Tyr
                910                 915

TTG GAT TAT GAG AAG GAG GAA GTG GAA GCT CAG CCC AGG           3045
Leu Asp Tyr Glu Lys Glu Glu Val Glu Ala Gln Pro Arg
        920                 925                 930

CAG TGG AAG AAA TAC GAC TTT CAC TAC GAC AAT GTG CTC           3084
```

```
                              -continued

Gln Trp Lys Lys Tyr Asp Phe His Tyr Asp Asn Val Leu
        935                 940

TGG GCT CTG CTG ACG CTG TTC ACA GTG TCC ACG GGA GAA         3123
Trp Ala Leu Leu Thr Leu Phe Thr Val Ser Thr Gly Glu
945             950                 955

GGC TGG CCC ATG GTG CTG AAA CAC TCC GTG GAT GCC ACC         3162
Gly Trp Pro Met Val Leu Lys His Ser Val Asp Ala Thr
        960                 965                 970

TAT GAG GAG CAG GGT CCA AGC CCT GGG TAC CGC ATG GAG         3201
Tyr Glu Glu Gln Gly Pro Ser Pro Gly Tyr Arg Met Glu
            975                 980

CTG TCC ATC TTC TAC GTG GTC TAC TTT GTG GTC TTT CCC         3240
Leu Ser Ile Phe Tyr Val Val Tyr Phe Val Val Phe Pro
    985                 990                 995

TTC TTC TTC GTC AAC ATC TTT GTG GCT TTG ATC ATC ATC         3279
Phe Phe Phe Val Asn Ile Phe Val Ala Leu Ile Ile Ile
                1000                1005

ACC TTC CAG GAG CAG GGG GAC AAG GTG ATG TCT GAA TGC         3318
Thr Phe Gln Glu Gln Gly Asp Lys Val Met Ser Glu Cys
1010            1015                1020

AGC CTG GAG AAG AAC GAG AGG GCT TGC ATT GAC TTC GCC         3357
Ser Leu Glu Lys Asn Glu Arg Ala Cys Ile Asp Phe Ala
        1025                1030                1035

ATC AGC GCC AAA CCC CTG ACA CGG TAC ATG CCC CAA AAC         3396
Ile Ser Ala Lys Pro Leu Thr Arg Tyr Met Pro Gln Asn
            1040                1045

CGG CAG TCG TTC CAG TAT AAG ACN TGG ACA TTT GTG GTC         3435
Arg Gln Ser Phe Gln Tyr Lys Thr Trp Thr Phe Val Val
    1050                1055                1060

TCC CCG CCC TTT GAA TAC TTC ATC ATG GCC ATG ATN GCC         3474
Ser Pro Pro Phe Glu Tyr Phe Ile Met Ala Met Ile Ala
                1065                1070

CTC AAC ACT GTG GTN CTN ATN ATG AAG TTC TAT GAT GCA         3513
Leu Asn Thr Val Val Leu Met Met Lys Phe Tyr Asp Ala
1075            1080                1085

CCC TAT GAG TAC NAG CTG ATG CTG AAA TGC CTG AAC ATC         3552
Pro Tyr Glu Tyr Glu Leu Met Leu Lys Cys Leu Asn Ile
        1090                1095                1100

GTG TTC ACA TCC ATG TTC TCC ATG GAA TGC GTG CTG AAG         3591
Val Phe Thr Ser Met Phe Ser Met Glu Cys Val Leu Lys
            1105                1110

ATC ATC GCC TTT NGG GTG CTG AAC TAT TTC AGA GAT GCC         3630
Ile Ile Ala Phe Gly Val Leu Asn Tyr Phe Arg Asp Ala
    1115                1120                1125

TGG AAT GTC TTT GAC TTT GTC ACT GTG TTN GGA AGT ATT         3669
Trp Asn Val Phe Asp Phe Val Thr Val Leu Gly Ser Ile
                1130                1135

ACT GAT ATT TTA GTA ACA GAG ATN GCG GAA ACG AAC AAT         3708
Thr Asp Ile Leu Val Thr Glu Ile Ala Glu Thr Asn Asn
1140            1145                1150

TTC ATC AAC CTC AGC TTC CTC CGN CTC TTT CGA GCT GNG         3747
Phe Ile Asn Leu Ser Phe Leu Arg Leu Phe Arg Ala Xaa
        1155                1160                1165

CGG CTG ATC AAG CTG CTC NGG CAG GGC TAC ACN ATC CGC         3786
Arg Leu Ile Lys Leu Leu Arg Gln Gly Tyr Thr Ile Arg
            1170                1175

ATC CTG CTG TGG ACC TTT GTC CAG TCN TTC AAG GCC CTG         3825
Ile Leu Leu Trp Thr Phe Val Gln Ser Phe Lys Ala Leu
    1180                1185                1190
```

-continued

| | |
|---|---|
| CCC TAC GTG TGT CTG CTC ATT GCC ATG CTG TTC TTC ATC<br>Pro Tyr Val Cys Leu Leu Ile Ala Met Leu Phe Phe Ile<br>             1195                       1200 | 3864 |
| TAC GCC ATC ATC GGC ATG CAG GTG TTT GGG AAT ATT GCC<br>Tyr Ala Ile Ile Gly Met Gln Val Phe Gly Asn Ile Ala<br>1205                 1210                    1215 | 3903 |
| CTG GAT GAT GAC ACC AGC ATC AAC CGC CAC AAC AAC TTC<br>Leu Asp Asp Asp Thr Ser Ile Asn Arg His Asn Asn Phe<br>             1220                    1225                1230 | 3942 |
| CGG ACG TTT TTG CAA GCC CTG ATN CTG CTG TTC AGG AGC<br>Arg Thr Phe Leu Gln Ala Leu Met Leu Leu Phe Arg Ser<br>             1235                    1240 | 3981 |
| GCC ACG GGG GAG GCC TGG CAC GAG ATC ATG CTG TCC TGC<br>Ala Thr Gly Glu Ala Trp His Glu Ile Met Leu Ser Cys<br>             1245                    1250                1255 | 4020 |
| CTG AGC AAC CAG GCC TGT GAT GAG CAG GCC AAT GCC ACC<br>Leu Ser Asn Gln Ala Cys Asp Glu Gln Ala Asn Ala Thr<br>             1260                    1265 | 4059 |
| GAG TGT GGA AGT GAC TTT GCC TAC TTC TAC TTC GTC TCC<br>Glu Cys Gly Ser Asp Phe Ala Tyr Phe Tyr Phe Val Ser<br>1270                 1275                    1280 | 4098 |
| TTC ATC TTC CTG TGC TCC TTN CTG ATG TTG AAC CTC TTT<br>Phe Ile Phe Leu Cys Ser Phe Leu Met Leu Asn Leu Phe<br>             1285                    1290                1295 | 4137 |
| GTG GCN GTG ATC ATG GAC AAT TTT GAG TAC CTC ACG CGG<br>Val Ala Val Ile Met Asp Asn Phe Glu Tyr Leu Thr Arg<br>                    1300                    1305 | 4176 |
| GAC TCT TCC ATC CTA GGT NCT CAC CAC TTG GAT GAG TTC<br>Asp Ser Ser Ile Leu Gly Pro His His Leu Asp Glu Phe<br>             1310                    1315                1320 | 4215 |
| ATC CGG GTC TNG GCT GAA TAC GAC CCG GNN GNG TGT GGG<br>Ile Arg Val Trp Ala Glu Tyr Asp Pro Ala Ala Cys Gly<br>             1325                    1330 | 4254 |
| CGC ATC AGT TAC AAT GAC ATG TTT GAG ATG CTG AAA CAC<br>Arg Ile Ser Tyr Asn Asp Met Phe Glu Met Leu Lys His<br>1335                 1340                    1345 | 4293 |
| ATG TCC CCG CCT CTG GGG CTG GGG AAG AAA TGC CCT GCT<br>Met Ser Pro Pro Leu Gly Leu Gly Lys Lys Cys Pro Ala<br>             1350                    1355                1360 | 4332 |
| CGA GTT GCT TAC AAG CGC CTG GTT CGC ATG AAC ATG CCC<br>Arg Val Ala Tyr Lys Arg Leu Val Arg Met Asn Met Pro<br>             1365                    1370 | 4371 |
| ATC TCC AAC GAG GAC ATG ACT GTT CAC TTC ACG TCC ACG<br>Ile Ser Asn Glu Asp Met Thr Val His Phe Thr Ser Thr<br>1375                 1380                    1385 | 4410 |
| CTG ATG GCC CTC ATC CGG ACG GCA CTG GAG ATC AAG CTG<br>Leu Met Ala Leu Ile Arg Thr Ala Leu Glu Ile Lys Leu<br>             1390                    1395 | 4449 |
| GCC CCA GCT GGG ACA AAG CAG CAT CAG TGT GAC GCG GAG<br>Ala Pro Ala Gly Thr Lys Gln His Gln Cys Asp Ala Glu<br>1400                 1405                    1410 | 4488 |
| TTG AGG AAG GAG ATT TCC GTT GTG TGG GCC AAT CTG CCC<br>Leu Arg Lys Glu Ile Ser Val Val Trp Ala Asn Leu Pro<br>             1415                    1420                1425 | 4527 |
| CAG AAG ACT TTG GAC TTG CTG GTA CCA CCC CAT AAG CCT<br>Gln Lys Thr Leu Asp Leu Leu Val Pro Pro His Lys Pro<br>             1430                    1435 | 4566 |
| GAT GAG ATG ACA GTG GGG AAG GTT TAT GCA GCT CTG ATG<br>Asp Glu Met Thr Val Gly Lys Val Tyr Ala Ala Leu Met<br>             1440                    1445                1450 | 4605 |

```
ATA TTT GAC TTC TAC AAG CAG AAC AAA ACC ACC AGA GAC                                 4644
Ile Phe Asp Phe Tyr Lys Gln Asn Lys Thr Thr Arg Asp
            1455                    1460

CAG ATG CAG CAG GCT CCT GGA GGC CTC TCC CAG ATN GGT                                 4683
Gln Met Gln Gln Ala Pro Gly Gly Leu Ser Gln Met Gly
1465                1470                1475

CCT GTG TCC CTG TTC CAC CCT CTG AAG GCC ACC CTG GAG                                 4722
Pro Val Ser Leu Phe His Pro Leu Lys Ala Thr Leu Glu
        1480                1485                1490

CAG ACA CAG CCG GCT GTN CTC CGA GGA GCC CGG GTT TTN                                 4761
Gln Thr Gln Pro Ala Val Leu Arg Gly Ala Arg Val Phe
                1495                1500

CTT CGA CAG AAG AGT TCC ACC TCC CTC AGC AAT GGC GGG                                 4800
Leu Arg Gln Lys Ser Ser Thr Ser Leu Ser Asn Gly Gly
        1505                1510                1515

GCC ATA CAA AAC CAA GAG AGT GGC ATC ANA GAG TCT GTC                                 4839
Ala Ile Gln Asn Gln Glu Ser Gly Ile Lys Glu Ser Val
                1520                1525

TCC TGG GGC ACT CAA AGG ACC CAG GAT GCA CCC CAT GAG                                 4878
Ser Trp Gly Thr Gln Arg Thr Gln Asp Ala Pro His Glu
1530                1535                1540

GCC AGG CCA CCC CTG GAG CGT GGC CAC TCC ACA GAG ATC                                 4917
Ala Arg Pro Pro Leu Glu Arg Gly His Ser Thr Glu Ile
        1545                1550                1555

CCT GTG GGG CGT TCA GGA GCA CTG GCT GTG GAC GTT CAG                                 4956
Pro Val Gly Arg Ser Gly Ala Leu Ala Val Asp Val Gln
                1560                1565

ATG CAG AGC ATA ACC CGG AGG GGC CCT GAT GGG GAG CCC                                 4995
Met Gln Ser Ile Thr Arg Arg Gly Pro Asp Gly Glu Pro
        1570                1575                1580

CAG CCT GGG CTG GAG AGC CAG GGT CGA GCG GCC TCC ATG                                 5034
Gln Pro Gly Leu Glu Ser Gln Gly Arg Ala Ala Ser Met
                1585                1590

CCC CGC CTT GCG GCC GAG ACT CAG CCC GTC ACA GAT GCC                                 5073
Pro Arg Leu Ala Ala Glu Thr Gln Pro Val Thr Asp Ala
1595                1600                1605

AGC CCC ATG AAG CGC TCC ATC TCC ACG CTG GCC CAG CGG                                 5112
Ser Pro Met Lys Arg Ser Ile Ser Thr Leu Ala Gln Arg
        1610                1615                1620

CCC CGT GGG ACT CAT CTT TGC AGC ACC ACC CCG GAC CGC                                 5151
Pro Arg Gly Thr His Leu Cys Ser Thr Thr Pro Asp Arg
                1625                1630

CCA CCC CCT AGC CAG GCG TCG TCG CAC CAC CAC CAC CAC                                 5190
Pro Pro Pro Ser Gln Ala Ser Ser His His His His His
        1635                1640                1645

CGC TGC CAC CGC CGC AGG GAC AGG AAG CAG AGG TCC CTG                                 5229
Arg Cys His Arg Arg Arg Asp Arg Lys Gln Arg Ser Leu
                1650                1655

GAG AAG GGG CCC AGC CTG TCT GCC GAT ATG GAT GGC GCA                                 5268
Glu Lys Gly Pro Ser Leu Ser Ala Asp Met Asp Gly Ala
1660                1665                1670

CCA AGC AGT GCT GTG GGG CCG GGC CTG CCC CCG GGA GAG                                 5307
Pro Ser Ser Ala Val Gly Pro Gly Leu Pro Pro Gly Glu
        1675                1680                1685

GGG CCT ACA GGC TGC CGG CGG GAA CGA GAG CGC CGG CAG                                 5346
Gly Pro Thr Gly Cys Arg Arg Glu Arg Glu Arg Arg Gln
                1690                1695

GAG CGG GGC CGG TCC CAG GAG CGG AGG CAG CCC TCA TCC                                 5385
Glu Arg Gly Arg Ser Gln Glu Arg Arg Gln Pro Ser Ser
```

-continued

|  |  |
|---|---|
| 1700                  1705                  1710 | |
| TCC TCC TCG GAG AAG CAG CGC TTC TAC TCC TGC GAC CGC<br>Ser Ser Ser Glu Lys Gln Arg Phe Tyr Ser Cys Asp Arg<br>              1715                  1720 | 5424 |
| TTT GGG GGC CGT GAG CCC CCG AAG CCC AAG CCC TCC CTC<br>Phe Gly Gly Arg Glu Pro Pro Lys Pro Lys Pro Ser Leu<br>1725                  1730                  1735 | 5463 |
| AGC AGC CAC CCA ACG TCG CCA ACA GCT GGC CAG GAG CCG<br>Ser Ser His Pro Thr Ser Pro Thr Ala Gly Gln Glu Pro<br>              1740                  1745                  1750 | 5502 |
| GGA CCC CAC CCA CAG GGC AGT GGT TCC GTG AAT GGG AGC<br>Gly Pro His Pro Gln Gly Ser Gly Ser Val Asn Gly Ser<br>                            1755                  1760 | 5541 |
| CCC TTG CTG TCA ACA TCT GGT GCT AGC ACC CCC GGC NGC<br>Pro Leu Leu Ser Thr Ser Gly Ala Ser Thr Pro Gly Arg<br>     1765                  1770                  1775 | 5580 |
| GGT GGG CGG AGG CAG CTC CCC CAG ACG CCC CTG ACT CCC<br>Gly Gly Arg Arg Gln Leu Pro Gln Thr Pro Leu Thr Pro<br>              1780                  1785 | 5619 |
| CGC CCC AGC ATC ACC TAC AAG ACG GCC AAC TCC TCA CCC<br>Arg Pro Ser Ile Thr Tyr Lys Thr Ala Asn Ser Ser Pro<br>1790                  1795                  1800 | 5658 |
| ATC CAC TTC GCC GGG GCT CAG ACC AGC CTC CCT GCC TTC<br>Ile His Phe Ala Gly Ala Gln Thr Ser Leu Pro Ala Phe<br>              1805                  1810                  1815 | 5697 |
| TCC CCA GGC CGG CTC AGC CGT GGG CTT TCC GAA CAC AAC<br>Ser Pro Gly Arg Leu Ser Arg Gly Leu Ser Glu His Asn<br>                            1820                  1825 | 5736 |
| GCC CTG CTG CAG AGA GAC CCC CTC AGC CAG CCC CTG GCC<br>Ala Leu Leu Gln Arg Asp Pro Leu Ser Gln Pro Leu Ala<br>              1830                  1835                  1840 | 5775 |
| CCT GGC TCT CGA ATT GGC TCT GAC CCT TAC CTG GGG CAG<br>Pro Gly Ser Arg Ile Gly Ser Asp Pro Tyr Leu Gly Gln<br>                   1845                  1850 | 5814 |
| NGT CTG GAC AGT GAG GCC TCT GTC CAC GCC CTG CCT GAG<br>Arg Leu Asp Ser Glu Ala Ser Val His Ala Leu Pro Glu<br>1855                  1860                  1865 | 5853 |
| GAC ACG CTC ACT TTC GAG GAG GCT GTG GCC ACC AAC TCG<br>Asp Thr Leu Thr Phe Glu Glu Ala Val Ala Thr Asn Ser<br>              1870                  1875                  1880 | 5892 |
| GGC CGC TCC TCC AGG ACT TCC TAC GTG TCC TCC CTG ACC<br>Gly Arg Ser Ser Arg Thr Ser Tyr Val Ser Ser Leu Thr<br>                            1885                  1890 | 5931 |
| TCC CAG TCT CAC CCT CTC CGC CGC GTG CCC AAC GGT TAC<br>Ser Gln Ser His Pro Leu Arg Arg Val Pro Asn Gly Tyr<br>      1895                  1900                  1905 | 5970 |
| CAC TGC ACC CTG GGA CTC AGC TCG GGT GGC CGA GCA CGG<br>His Cys Thr Leu Gly Leu Ser Ser Gly Gly Arg Ala Arg<br>              1910                  1915 | 6009 |
| CAC AGC TAC CAC CAC CCT GAC CAA GAC CAC TGG TGC<br>His Ser Tyr His His Pro Asp Gln Asp His Trp Cys<br>1920                  1925                  1930 | 6045 |
| TAGCTGCACC GTGACCGCTC AGACGCCTGC ATGCAGCAGG | 6085 |
| CGTGTGTTCC AGTGGATGAG TTTTATCATC CACACGGGGC | 6125 |
| AGTCGGCCCT CGGGGAGGC CTTGCCCACC TTGGTGAGGC | 6165 |
| TCCTGTGGCC CCTCCCTCCC CCTCCTCCCC TCTTTTACTC | 6205 |
| TAGACGACGA ATAAAGCCCT GTTAGAG | 6232 |

(2) INFORMATION FOR SEQ ID NO: 12:

(i) SEQUENCE CHARACTERISTICS:
        (A) LENGTH: 2980 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:12:

```
GAA TTC TCA ATC TCT CAT CTT ATG CAA AAA TCA ACT CAA            39
Glu Phe Ser Ile Ser His Leu Met Gln Lys Ser Thr Gln
 1               5                  10

GAT GGA TCA AAA GAC CTA AAT CCA AGA CCT GAA ACC ATA            78
Asp Gly Ser Lys Asp Leu Asn Pro Arg Pro Glu Thr Ile
        15                  20                  25

AAG ATA CTA GAA GGT AAC ATC AGA ATA TCC TTC AAG ACA           117
Lys Ile Leu Glu Gly Asn Ile Arg Ile Ser Phe Lys Thr
                30                  35

TTG GCT TAG GCA AAG ACT TTT TGA CCA AAA ACC CAA AAG           156
Leu Ala     Ala Lys Thr Phe     Pro Lys Thr Gln Lys
 40                 45                  50

AAC AAC AAA CCA GAA GTC AAC CAG ATA GCC AAC AGT GAC           195
Asn Asn Lys Pro Glu Val Asn Gln Ile Ala Asn Ser Asp
        55                  60                  65

AAC AAG GTT ACA ATT GAT GAC TAT AGA GAA GAG GAT GAA           234
Asn Lys Val Thr Ile Asp Asp Tyr Arg Glu Glu Asp Glu
                70                  75

GAC AAG GAC CCC TAT CCG CCT TGC GAT GTG CCA GTA GGG           273
Asp Lys Asp Pro Tyr Pro Pro Cys Asp Val Pro Val Gly
 80                 85                  90

GAA GAG GAA GAG GAA GAG GAG GAT GAA CCT GAG GTT               312
Glu Glu Glu Glu Glu Glu Glu Asp Glu Pro Glu Val
        95                  100

CCT GCC GGA CCC CGT CCT CGA AGG ATC TCG GAG TTG AAC           351
Pro Ala Gly Pro Arg Pro Arg Arg Ile Ser Glu Leu Asn
105                 110                 115

ATG AAG GAA AAA ATT GCC CCC ATC CCT GAA GGG AGC GCT           390
Met Lys Glu Lys Ile Ala Pro Ile Pro Glu Gly Ser Ala
        120                 125                 130

TTC TTC ATT CTT AGC AAG ACC AAC CCG ATC CGC GTA GGC           429
Phe Phe Ile Leu Ser Lys Thr Asn Pro Ile Arg Val Gly
                135                 140

TGC CAC AAG CTC ATC AAC CAC CAC ATC TTC ACC AAC CTC           468
Cys His Lys Leu Ile Asn His His Ile Phe Thr Asn Leu
145                 150                 155

ATC CTT GTC TTC ATC ATG CTG AGC AGC GCT GCC CTG GCC           507
Ile Leu Val Phe Ile Met Leu Ser Ser Ala Ala Leu Ala
        160                 165

GCA GAG GAC CCC ATC CGC AGC CAC TCC TTC CGG AAC ACG           546
Ala Glu Asp Pro Ile Arg Ser His Ser Phe Arg Asn Thr
170                 175                 180

ATA CTG GGT TAC TTT GAC TAT GCC TTC ACA GCC ATC TTT           585
Ile Leu Gly Tyr Phe Asp Tyr Ala Phe Thr Ala Ile Phe
        185                 190                 195

ACT GTT GAG ATC CTG TTG AAG ATG ACA ACT TTT GGA GCT           624
Thr Val Glu Ile Leu Leu Lys Met Thr Thr Phe Gly Ala
                200                 205

TTC CTC CAC AAA GGG GCC TTC TGC AGG AAC TAC TTC AAT           663
```

```
                        Phe Leu His Lys Gly Ala Phe Cys Arg Asn Tyr Phe Asn
                            210                 215                 220

TTG CTG GAT ATG CTG GTG GTT GGG GTG TCT CTG GTG TCA                                 702
Leu Leu Asp Met Leu Val Val Gly Val Ser Leu Val Ser
            225                 230

TTT GGG ATT CAA TCC AGT GCC ATC TCC GTT GTG AAG ATT                                 741
Phe Gly Ile Gln Ser Ser Ala Ile Ser Val Val Lys Ile
235                 240                 245

CTG AGG GTC TTA AGG GTC CTG CGT CCC CTC AGG GCC ATC                                 780
Leu Arg Val Leu Arg Val Leu Arg Pro Leu Arg Ala Ile
                250                 255                 260

AAC AGA GCA AAA GGA CTT AAG CAC GTG GTC CAG TGC GTC                                 819
Asn Arg Ala Lys Gly Leu Lys His Val Val Gln Cys Val
                    265                 270

TTC GTG GCC ATC CGG ACC ATC GGC AAC ATC ATG ATC GTC                                 858
Phe Val Ala Ile Arg Thr Ile Gly Asn Ile Met Ile Val
275                 280                 285

ACC ACC CTC CTG CAG TTC ATG TTT GCC TGT ATC GGG GTC                                 897
Thr Thr Leu Leu Gln Phe Met Phe Ala Cys Ile Gly Val
                290                 295

CAG TTG TTC AAG GGG AAG TTC TAT CGC TGT ACG GAT GAA                                 936
Gln Leu Phe Lys Gly Lys Phe Tyr Arg Cys Thr Asp Glu
300                 305                 310

GCC AAA AGT AAC CCT GTT GAA TGC AGG GGA CTT TTC ATC                                 975
Ala Lys Ser Asn Pro Val Glu Cys Arg Gly Leu Phe Ile
                315                 320                 325

CTC TAC AAG GAT GGG GAT GTT GAC AGT GGT GTG GTC CGT                                1014
Leu Tyr Lys Asp Gly Asp Val Asp Ser Gly Val Val Arg
                    330                 335

GAA CGG ACT CGG CAA AAC AGT GAT TTC AAC TTC GAC AAC                                1053
Glu Arg Thr Arg Gln Asn Ser Asp Phe Asn Phe Asp Asn
340                 345                 350

GTC CTC TCT GCT ATG ATG GCG CTC TTC ACA GTC TCC ACG                                1092
Val Leu Ser Ala Met Met Ala Leu Phe Thr Val Ser Thr
                355                 360

TTT GAG GGC TGG CCT GCG TTG CTG TAT AAA GCC ATC GAC                                1131
Phe Glu Gly Trp Pro Ala Leu Leu Tyr Lys Ala Ile Asp
365                 370                 375

TCG AAT GGA GAG AAC ATC GGC CCA ATC TAC AAC CAC CGC                                1170
Ser Asn Gly Glu Asn Ile Gly Pro Ile Tyr Asn His Arg
                380                 385                 390

GTG GAG ATC TCC ATC TTC TTC ATC ATC TAC ATC ATC ATT                                1209
Val Glu Ile Ser Ile Phe Phe Ile Ile Tyr Ile Ile Ile
                    395                 400

GTA GCT TTC TTC ATG ATG AAC ATC TTT GTG GGC TTT GTC                                1248
Val Ala Phe Phe Met Met Asn Ile Phe Val Gly Phe Val
            405                 410                 415

ATC GTT ACA TTT CAG GAA CAA GGA GAA AAA GAG TAT AAG                                1287
Ile Val Thr Phe Gln Glu Gln Gly Glu Lys Glu Tyr Lys
                420                 425

AAC TGT GAG CTG GAC AAA AAT CAG CGT CAG TGT GTT GAA                                1326
Asn Cys Glu Leu Asp Lys Asn Gln Arg Gln Cys Val Glu
430                 435                 440

TAC GCC TTG AAA GCA CGT CCC TTG CGG AGA TAC ATC CCC                                1365
Tyr Ala Leu Lys Ala Arg Pro Leu Arg Arg Tyr Ile Pro
                445                 450                 455

AAA AAC CCC TAC CAG TAC AAG TTC TGG TAC GTG GTG AAC                                1404
Lys Asn Pro Tyr Gln Tyr Lys Phe Trp Tyr Val Val Asn
                    460                 465
```

```
TCT TCG CCT TTC GAA TAC ATG ATG TTT GTC CTC ATC ATG                    1443
Ser Ser Pro Phe Glu Tyr Met Met Phe Val Leu Ile Met
    470                 475                 480

CTC AAC ACA CTC TGC TTG GCC ATG CAG CAC TAC GAG CAG                    1482
Leu Asn Thr Leu Cys Leu Ala Met Gln His Tyr Glu Gln
                485                 490

TCC AAG ATG TTC AAT GAT GCC ATG GAC ATT CTG AAC ATG                    1521
Ser Lys Met Phe Asn Asp Ala Met Asp Ile Leu Asn Met
495                 500                 505

GTC TTC ACC GGG GTG TTC ACC GTC GAG ATG GTT TTG AAA                    1560
Val Phe Thr Gly Val Phe Thr Val Glu Met Val Leu Lys
        510                 515                 520

GTC ATC GCA TTT AAG CCT AAG GGG TAT TTT AGT GAC GCC                    1599
Val Ile Ala Phe Lys Pro Lys Gly Tyr Phe Ser Asp Ala
                525                 530

TGG AAC ACG TTT GAC TCC CTC ATC GTA ATC GGC AGC ATT                    1638
Trp Asn Thr Phe Asp Ser Leu Ile Val Ile Gly Ser Ile
535                 540                 545

ATA GAC GTG GCC CTC AGC GAA GCA GAC CAC TAT TTC ACT                    1677
Ile Asp Val Ala Leu Ser Glu Ala Asp His Tyr Phe Thr
        550                 555

GAT GCA TGG AAC ACT TTT GAT GCC TTA ATT GTT GTT GGT                    1716
Asp Ala Trp Asn Thr Phe Asp Ala Leu Ile Val Val Gly
560                 565                 570

AGC GTC GTT GAT ATT GCT ATA ACT GAA GTG AAT CCA ACT                    1755
Ser Val Val Asp Ile Ala Ile Thr Glu Val Asn Pro Thr
            575                 580                 585

GAA AGT GAA AAT GTC CCT GTC CCA ACT GCT ACA CCT GGG                    1794
Glu Ser Glu Asn Val Pro Val Pro Thr Ala Thr Pro Gly
                590                 595

AAC TCT GAA GAG AGC AAT AGA ATC TCC ATC ACC TTT TTC                    1833
Asn Ser Glu Glu Ser Asn Arg Ile Ser Ile Thr Phe Phe
600                 605                 610

CGT CTT TTC CGA GTG ATG CGA TTG GTG AAG CTT CTC AGC                    1872
Arg Leu Phe Arg Val Met Arg Leu Val Lys Leu Leu Ser
        615                 620

AGG GGG GAA GGC ATC CGG ACA TTG CTG TGG ACT TTT ATT                    1911
Arg Gly Glu Gly Ile Arg Thr Leu Leu Trp Thr Phe Ile
625                 630                 635

AAG TCC TTT CAG GCG CTC CCG TAT GTG GCC CTC CTC ATA                    1950
Lys Ser Phe Gln Ala Leu Pro Tyr Val Ala Leu Leu Ile
            640                 645                 650

GCC ATG CTG TTC TTC ATC TAT GCG GTC ATT GGC ATG CAG                    1989
Ala Met Leu Phe Phe Ile Tyr Ala Val Ile Gly Met Gln
                655                 660

ATG TTT GGG AAA GTT GCC ATG AGA GAT AAC AAC CAG ATC                    2028
Met Phe Gly Lys Val Ala Met Arg Asp Asn Asn Gln Ile
665                 670                 675

AAT AGG AAC AAT AAC TTC CAG ACG TTT CCC CAG GCG GTG                    2067
Asn Arg Asn Asn Asn Phe Gln Thr Phe Pro Gln Ala Val
        680                 685

CTG CTG CTC TTC AGG TGT GCA ACA GGT GAG GCC TGG CAG                    2106
Leu Leu Leu Phe Arg Cys Ala Thr Gly Glu Ala Trp Gln
690                 695                 700

GAG ATC ATG CTG GCC TGT CTC CCA GGG AAG CTC TGT GAC                    2145
Glu Ile Met Leu Ala Cys Leu Pro Gly Lys Leu Cys Asp
            705                 710                 715

CCT GAG TCA GAT TAC AAC CCC GGG GAG GAG TAT ACA TGT                    2184
Pro Glu Ser Asp Tyr Asn Pro Gly Glu Glu Tyr Thr Cys
                720                 725
```

-continued

```
GGG AGC AAC TTT GCC ATT GTC TAT TTC ATC AGT TTT TAC           2223
Gly Ser Asn Phe Ala Ile Val Tyr Phe Ile Ser Phe Tyr
730                 735                 740

ATG CTC TGT GCA TTT CTG ATC ATC AAT CTG TTT GTG GCT           2262
Met Leu Cys Ala Phe Leu Ile Ile Asn Leu Phe Val Ala
        745                 750

GTC ATC ATG GAT AAT TTC GAC TAT CTG ACC CGG GAC TGG           2301
Val Ile Met Asp Asn Phe Asp Tyr Leu Thr Arg Asp Trp
755                 760                 765

TCT ATT TTG GGG CCT CAC CAT TTA GAT GAA TTC AAA AGA           2340
Ser Ile Leu Gly Pro His His Leu Asp Glu Phe Lys Arg
            770                 775                 780

ATA TGG TCA GAA TAT GAC CCT GAG GCA AAG GGA AGG ATA           2379
Ile Trp Ser Glu Tyr Asp Pro Glu Ala Lys Gly Arg Ile
                785                 790

AAA CAC CTT GAT GTG GTC ACT CTG CTT CGA CGC ATC CAG           2418
Lys His Leu Asp Val Val Thr Leu Leu Arg Arg Ile Gln
795                 800                 805

CCT CCC CTG GGG TTT GGG AAG TTA TGT CCA CAC AGG GTA           2457
Pro Pro Leu Gly Phe Gly Lys Leu Cys Pro His Arg Val
            810                 815

GCG TGC AAG AGA TTA GTT GCC ATG AAC ATG CCT CTC AAC           2496
Ala Cys Lys Arg Leu Val Ala Met Asn Met Pro Leu Asn
820                 825                 830

AGT GAC GGG ACA GTC ATG TTT AAT GCA ACC CTG TTT GCT           2535
Ser Asp Gly Thr Val Met Phe Asn Ala Thr Leu Phe Ala
            835                 840                 845

TTG GTT CGA ACG GCT CTT AAG ATC AAG ACC GAA GGG AAC           2574
Leu Val Arg Thr Ala Leu Lys Ile Lys Thr Glu Gly Asn
                850                 855

CTG GAG CAA GCT AAT GAA GAA CTT CGG GCT GTG ATA AAG           2613
Leu Glu Gln Ala Asn Glu Glu Leu Arg Ala Val Ile Lys
        860                 865                 870

AAA ATT TGG AAG AAA ACC AGC ATG AAA TTA CTT GAC CAA           2652
Lys Ile Trp Lys Lys Thr Ser Met Lys Leu Leu Asp Gln
            875                 880

GTT GTC CCT CCA GCT GGT GAT GAT GAG GTA ACC GTG GGG           2691
Val Val Pro Pro Ala Gly Asp Asp Glu Val Thr Val Gly
 885                 890                 895

AAG TTC TAT GCC ACT TTC CTG ATA CAG GAC TAC TTT AGG           2730
Lys Phe Tyr Ala Thr Phe Leu Ile Gln Asp Tyr Phe Arg
            900                 905                 910

AAA TTC AAG AAA CGG AAA GAA CAA GGA CTG GTG GGA AAG           2769
Lys Phe Lys Lys Arg Lys Glu Gln Gly Leu Val Gly Lys
                915                 920

ATC CCT GCG AAG AAC ACC ACA ATT GCC CTA CAG GCG GGA           2808
Ile Pro Ala Lys Asn Thr Thr Ile Ala Leu Gln Ala Gly
        925                 930                 935

TTA AGG ACA CTG CAT GAC ATT GGG CCA GAA ATC CGG CGT           2847
Leu Arg Thr Leu His Asp Ile Gly Pro Glu Ile Arg Arg
            940                 945

GCT ATA TCG TGT GAT TTG CAA GAT GAC GAG CCT GAG GAA           2886
Ala Ile Ser Cys Asp Leu Gln Asp Asp Glu Pro Glu Glu
950                 955                 960

ACA AAA CGA GAA GAA GAA GAT GAT GTG TTC AAA GTA ATT           2925
Thr Lys Arg Glu Glu Glu Asp Asp Val Phe Lys Val Ile
        965                 970                 975

ATT CCA CGC CTA GCT ACA CAC TGG CCA TCT GGA AAT AGC           2964
Ile Pro Arg Leu Ala Thr His Trp Pro Ser Gly Asn Ser
```

```
                    980             985
AGG GCA GGC CGA ATT C                                              2980
Arg Ala Gly Arg Ile
    990

(2) INFORMATION FOR SEQ ID NO: 13:

(i) SEQUENCE CHARACTERISTICS:
        (A) LENGTH: 1857 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:13:

TCA AAG GAA AGA GAG AAG GCA AAA GCA CGG GGA GAT TTC                 39
Ser Lys Glu Arg Glu Lys Ala Lys Ala Arg Gly Asp Phe
 1               5                  10

CAG AAG CTC CGG GAG AAG CAG CAG CTG GAG GAG GAT CTA                 78
Gln Lys Leu Arg Glu Lys Gln Gln Leu Glu Glu Asp Leu
     15                  20                  25

AAG GGC TAC TTG GAT TGG ATC ACC CAA GCT GAG GAC ATC                117
Lys Gly Tyr Leu Asp Trp Ile Thr Gln Ala Glu Asp Ile
             30                  35

GAT CCG GAG AAT GAG GAA GAA GGA GGA GAG GAA GGC AAA                156
Asp Pro Glu Asn Glu Glu Glu Gly Gly Glu Glu Gly Lys
 40                  45                  50

CGA AAT ACT AGC ATG CCC ACC AGC GAG ACT GAG TCT GTG                195
Arg Asn Thr Ser Met Pro Thr Ser Glu Thr Glu Ser Val
         55                  60                  65

AAC ACA GAG AAC GTC AGC GGT GAA GGC GAG AAC CGA GGC                234
Asn Thr Glu Asn Val Ser Gly Glu Gly Glu Asn Arg Gly
                 70                  75

TGC TGT GGA AGT CTC TGG TGC TGG TGG AGA CGG AGA GGC                273
Cys Cys Gly Ser Leu Trp Cys Trp Trp Arg Arg Arg Gly
     80                  85                  90

GCG GCA AGG CGG GGC CTC TGG TGT CGG CGG TGG GGT CAA                312
Ala Ala Arg Arg Gly Leu Trp Cys Arg Arg Trp Gly Gln
             95                 100

GCC ATC TCA AAA TCC AAA CTC AGC CGA CGC TGG CGC TGG                351
Ala Ile Ser Lys Ser Lys Leu Ser Arg Arg Trp Arg Trp
105                 110                 115

AAC CGA TTC AAT CGC AGA AGA TGT AGG GCC GCC GTG AAG                390
Asn Arg Phe Asn Arg Arg Arg Cys Arg Ala Ala Val Lys
        120                 125                 130

TCT GTC ACG TTT TAC TGG CTG GTT ATC GTC CTG GTG TTT                429
Ser Val Thr Phe Tyr Trp Leu Val Ile Val Leu Val Phe
            135                 140

CTG AAC ACC TTA ACC ATT TCC TCT GAG CAC TAC AAT CAG                468
Leu Asn Thr Leu Thr Ile Ser Ser Glu His Tyr Asn Gln
145                 150                 155

CCG AGT TGG TTG ACA CAG ATT CAA GAT ATT GCC AAC AAA                507
Pro Ser Trp Leu Thr Gln Ile Gln Asp Ile Ala Asn Lys
        160                 165

GTC CTC TTG GCT CTG TTC ACC TGC GAG ATG CTG GTA AAA                546
Val Leu Leu Ala Leu Phe Thr Cys Glu Met Leu Val Lys
170                 175                 180

ATG TAC AGC TTG GGC CTC CAA GCA TAT TTC ATC TCT CTT                585
Met Tyr Ser Leu Gly Leu Gln Ala Tyr Phe Ile Ser Leu
            185                 190                 195
```

```
TTC AAC CGG TTT GAT TGC TTC GTG GTG TGT GGT GGA ATC          624
Phe Asn Arg Phe Asp Cys Phe Val Val Cys Gly Gly Ile
            200                 205

ACT GAG ACG ATC TTG GTG GAA CTG GAA ATC ATG TCT CCC          663
Thr Glu Thr Ile Leu Val Glu Leu Glu Ile Met Ser Pro
    210                 215                 220

CTG GGG ATC TCT GTG TTT CGG TGT GTG CGC CTC TTA AGA          702
Leu Gly Ile Ser Val Phe Arg Cys Val Arg Leu Leu Arg
                225                 230

ATC TTC AAA GTG ACC AGG CAC TGG ACT TCC CTG AGC AAC          741
Ile Phe Lys Val Thr Arg His Trp Thr Ser Leu Ser Asn
235                 240                 245

TTA GTG GCA TCC TTA TTA AAC TCC ATG AAG TCC ATC GTC          780
Leu Val Ala Ser Leu Leu Asn Ser Met Lys Ser Ile Ala
            250                 255                 260

TCG CTG TTG CTT CTG CTT TTT CTC TTC ATT ATC ATC TTT          819
Ser Leu Leu Leu Leu Leu Phe Leu Phe Ile Ile Ile Phe
                265                 270

TCC TTG CTT GGG ATG CAG CTG TTT GGC GGC AAG TTT AAT          858
Ser Leu Leu Gly Met Gln Leu Phe Gly Gly Lys Phe Asn
    275                 280                 285

TTT GAT GAA ACG CAA ACC AAG CAA GCA GCC TTT GAC AAT          897
Phe Asp Glu Thr Gln Thr Lys Gln Ala Ala Phe Asp Asn
                290                 295

TTC CCT CAA GCA CTT CTC ACA GTG TTC CAG ATC CTG ACA          936
Phe Pro Gln Ala Leu Leu Thr Val Phe Gln Ile Leu Thr
300                 305                 310

GGC GAA GAC TGG AAT GCT GTG ATG TAC GAT GGC ATC ATG          975
Gly Glu Asp Trp Asn Ala Val Met Tyr Asp Gly Ile Met
            315                 320                 325

GCT TAC GGG GGC CCA TCC TCT TCA GGA ATG ATC GTC TGC         1014
Ala Tyr Gly Gly Pro Ser Ser Ser Gly Met Ile Val Cys
                330                 335

ATC TAC TTC ATC ATC CTC TTC ATT TGT GGT AAC TAT ATT         1053
Ile Tyr Phe Ile Ile Leu Phe Ile Cys Gly Asn Tyr Ile
    340                 345                 350

CTA CTG AAT GTC TTC TTG GCC ATC GCT GTA GAC AAT TTG         1092
Leu Leu Asn Val Phe Leu Ala Ile Ala Val Asp Asn Leu
                355                 360

GCT GAT GCT GAA AGT CTG AAC ACT GCT CAG AAA GAA GAA         1131
Ala Asp Ala Glu Ser Leu Asn Thr Ala Gln Lys Glu Glu
365                 370                 375

GCG GAA GAA AAG GAG AGG AAA AAG ATT GCC AGA AAA GAG         1170
Ala Glu Glu Lys Glu Arg Lys Lys Ile Ala Arg Lys Glu
            380                 385                 390

AGC CTA GAA AAT AAA AAG AAC AAC AAA CCA GAA GTC AAC         1209
Ser Leu Glu Asn Lys Lys Asn Asn Lys Pro Glu Val Asn
                395                 400

CAG ATA GCC AAC AGT GAC AAC AAG GTT ACA ATT GAT GAC         1248
Gln Ile Ala Asn Ser Asp Asn Lys Val Thr Ile Asp Asp
    405                 410                 415

TAT AGA GAA GAG GAT GAA GAC AAG GAC CCC TAT CCG CCT         1287
Tyr Arg Glu Glu Asp Glu Asp Lys Asp Pro Tyr Pro Pro
                420                 425

TGC GAT GTG CCA GTA GGG GAA GAG GAA GAG GAA GAG GAG         1326
Cys Asp Val Pro Val Gly Glu Glu Glu Glu Glu Glu Glu
430                 435                 440

GAG GAT GAA CCT GAG GTT CCT GCC GGA CCC CGT CCT CGA         1365
Glu Asp Glu Pro Glu Val Pro Ala Gly Pro Arg Pro Arg
            445                 450                 455
```

-continued

```
AGG ATC TCG GAG TTG AAC ATG AAG GAA AAA ATT GCC CCC          1404
Arg Ile Ser Glu Leu Asn Met Lys Glu Lys Ile Ala Pro
            460                 465

ATC CCT GAA GGG AGC GCT TTC TTC ATT CTT AGC AAG ACC          1443
Ile Pro Glu Gly Ser Ala Phe Phe Ile Leu Ser Lys Thr
    470                 475                 480

AAC CCG ATC CGC GTA GGC TGC CAC AAG CTC ATC AAC CAC          1482
Asn Pro Ile Arg Val Gly Cys His Lys Leu Ile Asn His
                485                 490

CAC ATC TTC ACC AAC CTC ATC CTT GTC TTC ATC ATG CTG          1521
His Ile Phe Thr Asn Leu Ile Leu Val Phe Ile Met Leu
495                 500                 505

AGC AGC GCT GCC CTG GCC GCA GAG GAC CCC ATC CGC AGC          1560
Ser Ser Ala Ala Leu Ala Ala Glu Asp Pro Ile Arg Ser
        510                 515                 520

CAC TCC TTC CGG AAC ACG ATA CTG GGT TAC TTT GAC TAT          1599
His Ser Phe Arg Asn Thr Ile Leu Gly Tyr Phe Asp Tyr
                525                 530

GCC TTC ACA GCC ATC TTT ACT GTT GAG ATC CTG TTG AAG          1638
Ala Phe Thr Ala Ile Phe Thr Val Glu Ile Leu Leu Lys
            535                 540                 545

ATG ACA ACT TTT GGA GCT TTC CTC CAC AAA GGG GCC TTC          1677
Met Thr Thr Phe Gly Ala Phe Leu His Lys Gly Ala Phe
                550                 555

TGC AGG AAC TAC TTC AAT TTG CTG GAT ATG CTG GTG GTT          1716
Cys Arg Asn Tyr Phe Asn Leu Leu Asp Met Leu Val Val
560                 565                 570

GGG GTG TCT CTG GTG TCA TTT GGG ATT CAA TCC AGT GCC          1755
Gly Val Ser Leu Val Ser Phe Gly Ile Gln Ser Ser Ala
        575                 580                 585

ATC TCC GTT GTG AAG ATT CTG AGG GTC TTA AGG GTC CTG          1794
Ile Ser Val Val Lys Ile Leu Arg Val Leu Arg Val Leu
                590                 595

CGT CCC CTC AGG GCC ATC AAC AGA GCA AAA GGA CTT AAG          1833
Arg Pro Leu Arg Ala Ile Asn Arg Ala Lys Gly Leu Lys
600                 605                 610

CAC GTG GTC CAG TGC GTC TTC GTG                              1857
His Val Val Gln Cys Val Phe Val
            615
```

(2) INFORMATION FOR SEQ ID NO: 14:

(i) SEQUENCE CHARACTERISTICS:
        (A) LENGTH: 920 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:14:

```
AT TTC CGC NAT GCC TGG AAC ATC TTC GAC TTT GTG ACT           38
   Phe Arg Xaa Ala Trp Asn Ile Phe Asp Phe Val Thr
   1                5                   10

GTT CTG GGC AGC ATC ACC GAT ATC CTC GTG ACT GAG TTT          77
Val Leu Gly Ser Ile Thr Asp Ile Leu Val Thr Glu Phe
        15                  20                  25

GGG AAT CCG AAT AAC TTC ATC AAC CTG AGC TTT CTC CGN          116
Gly Asn Pro Asn Asn Phe Ile Asn Leu Ser Phe Leu Arg
                30                  35

NNN TTC CGA GCT GCC CGG NNN ATC AAA CTT CTC CGT CAG          155
```

```
Xaa Phe Arg Ala Ala Arg Leu Ile Lys Leu Leu Arg Gln
 40                  45                  50
GT TAC ACC ATC CGN ATT CTT CTC TGG ACC TTT GTG CAG                    194
Gly Tyr Thr Ile Arg Ile Leu Leu Trp Thr Phe Val Gln
            55                  60

TCC TTC AAG GCC CTG CCT TAT GTC TGT CTG CTG ATC GCC                   233
Ser Phe Lys Ala Leu Pro Tyr Val Cys Leu Leu Ile Ala
 65                  70                  75

ATG CTC TTC TTC ATC TAT GCC ATC ATT GGG ATG CAG GTG                   272
Met Leu Phe Phe Ile Tyr Ala Ile Ile Gly Met Gln Val
            80                  85                  90

TTT GGT AAC ATT GGC ATC GAC GTG GAG GAC GAG GAC AGT                   311
Phe Gly Asn Ile Gly Ile Asp Val Glu Asp Glu Asp Ser
                95                  100

GAT GAA GAT GAG TTC CAA ATC ACT GAG CAC AAT AAC TTC                   350
Asp Glu Asp Glu Phe Gln Ile Thr Glu His Asn Asn Phe
 105                 110                 115

CGG ACC TTC TTC CAG GCC CTC ATG CTT CTC TTC CGG AGT                   389
Arg Thr Phe Phe Gln Ala Leu Met Leu Leu Phe Arg Ser
            120                 125

GCC ACC GGG GAA GCT TGG CAC AAC ATC ATG CTT TCC TGC                   428
Ala Thr Gly Glu Ala Trp His Asn Ile Met Leu Ser Cys
130                 135                 140

CTC AGC GGG AAA CCG TGT GAT AAG AAC TCT NNC ATC CTG                   467
Leu Ser Gly Lys Pro Cys Asp Lys Asn Ser Xaa Ile Leu
            145                 150                 155

ACT CGA GAG TGT GGC AAT GAA TTT GCT TAT TTT TNN TTT                   506
Thr Arg Glu Cys Gly Asn Glu Phe Ala Tyr Phe Tyr Phe
                160                 165

GTT TCC TTC ATC TTC CTC TGC TCG TTT CTG ATG CTG AAT                   545
Val Ser Phe Ile Phe Leu Cys Ser Phe Leu Met Leu Asn
 170                 175                 180

CTC TTT GTC GCC GTC ATC ATG GAC AAC TTT GAG TAC CTC                   584
Leu Phe Val Ala Val Ile Met Asp Asn Phe Glu Tyr Leu
            185                 190

ACC CGA GAC TCC TCC ATC CTG GGC CCC CAC CAC CTG GAT                   623
Thr Arg Asp Ser Ser Ile Leu Gly Pro His His Leu Asp
195                 200                 205

GAG TAC GTG CGT GTC TGG GCC GAG TAT GAC CCC GCA GCT                   662
Glu Tyr Val Arg Val Trp Ala Glu Tyr Asp Pro Ala Ala
            210                 215                 220

TGG GGC CGC ATG CCT TAC CTG GAC ATG TAT CAG ATG NTG                   701
Trp Gly Arg Met Pro Tyr Leu Asp Met Tyr Gln Met Leu
                225                 230

AGA CAC ATG TCT CCG NNC CTG GGT CTG GGG AAG AAG TGT                   740
Arg His Met Ser Pro Xaa Leu Gly Leu Gly Lys Lys Cys
 235                 240                 245

CCG GCC AGA GTG GCT TAC AAG CGG CTT CTG CGG ATG GAC                   779
Pro Ala Arg Val Ala Tyr Lys Arg Leu Leu Arg Met Asp
            250                 255

CTG CCC GTC GCA GAT GAC AAC ACC GTC CAC TTC AAT TCC                   818
Leu Pro Val Ala Asp Asp Asn Thr Val His Phe Asn Ser
260                 265                 270

ACC CTC ATG GCT CTG ATC CGC ACA GCC CTG GAC ATC AAG                   857
Thr Leu Met Ala Leu Ile Arg Thr Ala Leu Asp Ile Lys
            275                 280                 285

ATT GCC AAG GGA GGA GCC GAC AAA CAG CAG ATG GAC GCT                   896
Ile Ala Lys Gly Gly Ala Asp Lys Gln Gln Met Asp Ala
                290                 295

GAG CTG CGG AAG GAG ATG ATG GCG                                       920
```

```
Glu Leu Arg Lys Glu Met Met Ala
    300             305
```

(2) INFORMATION FOR SEQ ID NO: 15:

(i) SEQUENCE CHARACTERISTICS:
        (A) LENGTH: 1424 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:15:

```
GGGCGAAGCT ACCATCTGTG GGATTATGA CTG AAC GCC TCT                41
                                 Leu Asn Ala Ser
                                   1

AAG TCA GAA TCC CGC CCA GGC GGA ACG ATA CGG CAG CGC             80
Lys Ser Glu Ser Arg Pro Gly Gly Thr Ile Arg Gln Arg
  5              10                  15

CGC GGA GCC TCG GTT GGC CTC ACG GTT AAC CGG TCT CTC            119
Arg Gly Ala Ser Val Gly Leu Thr Val Asn Arg Ser Leu
         20              25                  30

TTC CTC TTC AGC GAA GAC AAC GTG GTG AGA AAA TAC GCC            158
Phe Leu Phe Ser Glu Asp Asn Val Val Arg Lys Tyr Ala
                 35                  40

AAA AAG ATC ACC GAA TGG CCT CCC TTT GAA TAT ATG ATT            197
Lys Lys Ile Thr Glu Trp Pro Pro Phe Glu Tyr Met Ile
     45                  50                  55

TTA GCC ACC ATC ATA GCG AAT TGC ATC GTC CTN GCA CTG            236
Leu Ala Thr Ile Ile Ala Asn Cys Ile Val Leu Ala Leu
             60                  65

GAG CAG CAT CTG CCT GAT GAT GAC AAG ACC CCG ATG TCT            275
Glu Gln His Leu Pro Asp Asp Asp Lys Thr Pro Met Ser
 70                  75                  80

GAA CGG CTG GAT GAC ACA GAA CCA TAC TTC ATT GGA ATT            314
Glu Arg Leu Asp Asp Thr Glu Pro Tyr Phe Ile Gly Ile
         85                  90                  95

TTT TGT TTC GAG GCT GGA ATT AAA ATC ATT GCC CTT GGG            353
Phe Cys Phe Glu Ala Gly Ile Lys Ile Ile Ala Leu Gly
                100                 105

TTT GCC TTC CAC AAA GGC TCC TAC TTG AGG AAT GGC TGG            392
Phe Ala Phe His Lys Gly Ser Tyr Leu Arg Asn Gly Trp
    110                 115                 120

AAT GTC ATG GAC TTT GTG GTG GTG CTA ACG GGC ATC TTG            431
Asn Val Met Asp Phe Val Val Val Leu Thr Gly Ile Leu
            125                 130

GCG ACA GTT GGG ACG GAG TTT GAC CTA CGG ACG CTG AGG            470
Ala Thr Val Gly Thr Glu Phe Asp Leu Arg Thr Leu Arg
135             140                 145

GCA GTT CGA GTG CTG CNN CCG CTC AAG CTG GTG TCT GGA            509
Ala Val Arg Val Leu Xaa Pro Leu Lys Leu Val Ser Gly
        150                 155                 160

ATC CCA ANT TTA CAA GTC GTC CTG AAG TCG ATC ATG AAG            548
Ile Pro Ser Leu Gln Val Val Leu Lys Ser Ile Met Lys
                165                 170

GCG ATG ATC CCT TTN CTG CAG ATC GNC CTC CTC CTA TTT            587
Ala Met Ile Pro Xaa Leu Gln Ile Gly Leu Leu Leu Phe
175                 180                 185

TTT NCA ATC CTT ATT TTT NCA ATC ATA GGG TTA GAA TTT            626
Phe Xaa Ile Leu Ile Phe Ala Ile Ile Gly Leu Glu Phe
            190                 195
```

```
TAT ATG GNA AAA TTT CAT ACC ACC TGC TTT GAA GAG GGG                    665
Tyr Met Gly Lys Phe His Thr Thr Cys Phe Glu Glu Gly
200             205                 210

ACA GAT GAC ATT CAG GGT GAG TCT CCG GCT CCA TGT GGG                    704
Thr Asp Asp Ile Gln Gly Glu Ser Pro Ala Pro Cys Gly
            215                 220             225

ACA GAA GAG CCC GCC CGC ACC TGC CCC AAT GGG ACC AAA                    743
Thr Glu Glu Pro Ala Arg Thr Cys Pro Asn Gly Thr Lys
                230                 235

TGT CAG CCC TAC TGG GAA GGG CCC AAC AAC GGG ATC ACT                    782
Cys Gln Pro Tyr Trp Glu Gly Pro Asn Asn Gly Ile Thr
240                 245                 250

CAG TTC GAC AAC ATC CTG TTT GCA GTG CTG ACT GTT TTC                    821
Gln Phe Asp Asn Ile Leu Phe Ala Val Leu Thr Val Phe
                255                 260

CAG TGC ATA ACC ATG GAA GGG TGG ACT GAT CTC CTC TAC                    860
Gln Cys Ile Thr Met Glu Gly Trp Thr Asp Leu Leu Tyr
265                 270                 275

AAT AGC AAC GAT NCC TCA GGG AAC ACT TGG AAC TGG TTG                    899
Asn Ser Asn Asp Ala Ser Gly Asn Thr Trp Asn Trp Leu
            280                 285                 290

TAC TTC ATC CCC CTC ATC ATC ATC GGC TCC TTT TTT ATG                    938
Tyr Phe Ile Pro Leu Ile Ile Ile Gly Ser Phe Phe Met
                295                 300

CTG AAC CTT GTG CTG GGT GTG CTG TCA GGG GNG TTT GCC                    977
Leu Asn Leu Val Leu Gly Val Leu Ser Gly Glu Phe Ala
            305                 310                 315

AAA GAA AGG GNA CGG GTG GAG NAC CGG NGG GNT TTT CTG                   1016
Lys Glu Arg Xaa Arg Val Glu Xaa Arg Arg Ala Phe Leu
                320                 325

AAG CTG AGG CGG NNA NAA CAG ATT GAA CGT GAG CTC AAT                   1055
Lys Leu Arg Arg Xaa Xaa Gln Ile Glu Arg Glu Leu Asn
330                 335                 340

GGG TAC ATG GAA TGG ATC TCA AAA GCA GAA GAG GTG ATC                   1094
Gly Tyr Met Glu Trp Ile Ser Lys Ala Glu Glu Val Ile
            345                 350                 355

CTC GCC NAG GAT GAA ACT GAC GGG GAG CAG AGG CAT CCC                   1133
Leu Ala Glu Asp Glu Thr Asp Gly Glu Gln Arg His Pro
                360                 365

TTT GAT GGA GCT CTG CGG AGA ACC ACC ATA AAG AAA AGC                   1172
Phe Asp Gly Ala Leu Arg Arg Thr Thr Ile Lys Lys Ser
370                 375                 380

AAG ACA GAT TTG CTC AAC CCC GAA GAG GNT GAG GAT CAG                   1211
Lys Thr Asp Leu Leu Asn Pro Glu Glu Xaa Glu Asp Gln
            385                 390

CTG GCT GAT ATA GCC TCT GTG GGT TCT CCC TTC GCC CGA                   1250
Leu Ala Asp Ile Ala Ser Val Gly Ser Pro Phe Ala Arg
395                 400                 405

GCC AGC ATT AAA AGT GCC AAG CTG GAG AAC TCG ACC TTT                   1289
Ala Ser Ile Lys Ser Ala Lys Leu Glu Asn Ser Thr Phe
            410                 415                 420

TTT CAC AAA AAG GAG AGG AGG ATG CGT TTC TAC ATC CGC                   1328
Phe His Lys Lys Glu Arg Arg Met Arg Phe Tyr Ile Arg
                425                 430

CGC ATG GTC AAA ACT CAG GCC TTC TAC TGG ACT GTA CTC                   1367
Arg Met Val Lys Thr Gln Ala Phe Tyr Trp Thr Val Leu
435                 440                 445

AGT TTG GTA GCT CTC AAC ACG CTG TGT GTT GCT ATT GTT                   1406
Ser Leu Val Ala Leu Asn Thr Leu Cys Val Ala Ile Val
```

```
                        450                 455
CAC TAC AAC CAG CCC GAG                                                 1424
His Tyr Asn Gln Pro Glu
460                 465

(2) INFORMATION FOR SEQ ID NO: 16:

(i) SEQUENCE CHARACTERISTICS:
        (A) LENGTH:  910 nucleotides
        (B) TYPE:  Nucleotide
        (C) STRANDEDNESS:  Single
        (D) TOPOLOGY:  Linear (ii) MOLECULE TYPE:  cDNA (xi) SEQUENCE DESCRIPTION: SEQ ID NO:16:

G GAG AAC TCG ACC TTT TTT CAC AAA AAG GAG AGG AGG                        37
  Glu Asn Ser Thr Phe Phe His Lys Lys Glu Arg Arg
   1               5                  10

ATG CGT TTC TAC ATC CGC CGC ATG GTC AAA ACT CAG GCC                      76
Met Arg Phe Tyr Ile Arg Arg Met Val Lys Thr Gln Ala
            15                  20                  25

TTC TAC TGG ACT GTA CTC AGT TTG GTA GCT CTC AAC ACG                      115
Phe Tyr Trp Thr Val Leu Ser Leu Val Ala Leu Asn Thr
                    30                  35

CTG TGT GTT GCT ATT GTT CAC TAC AAC CAG CCC GAG TGG                      154
Leu Cys Val Ala Ile Val His Tyr Asn Gln Pro Glu Trp
        40                  45                  50

CTC TCC GAC TTC CTT TAC TAT NCA GAA TTC ATT TTC TTA                      193
Leu Ser Asp Phe Leu Tyr Tyr Ala Glu Phe Ile Phe Leu
                55                  60

GGA CTC TTT ATG TCC GAA ATG TTT ATA AAA ATG TAC GGG                      232
Gly Leu Phe Met Ser Glu Met Phe Ile Lys Met Tyr Gly
 65              70                  75

CTT GGG ACG CGG CCT TAC TTC CAC TCT TCC TTC AAC NGC                      271
Leu Gly Thr Arg Pro Tyr Phe His Ser Ser Phe Asn Cys
            80                  85                  90

TTT GAC TGT GGG GTT ATC ATT GGG AGC ATC TNC GAG GTC                      310
Phe Asp Cys Gly Val Ile Ile Gly Ser Ile Phe Glu Val
                95                  100

ATC TGG GCT GTC ATA ANA CCT GGC ACA TCC TTN GGA ATC                      349
Ile Trp Ala Val Ile Lys Pro Gly Thr Ser Phe Gly Ile
        105                 110                 115

AGC GTG TTA CGA GCC CTC AGG TTA TTG CGT ATT TTC AAA                      388
Ser Val Leu Arg Ala Leu Arg Leu Leu Arg Ile Phe Lys
                120                 125

GTC ACA AAG TAC NGG GCA TCT CTC AGA AAC CTG GTC GTC                      427
Val Thr Lys Tyr Trp Ala Ser Leu Arg Asn Leu Val Val
130                 135                 140

TCT CTC CTC AAC TCC ATG AAG TCC ATC ATC AGC CTG TTG                      466
Ser Leu Leu Asn Ser Met Lys Ser Ile Ile Ser Leu Leu
            145                 150                 155

TTT CTC CTT TTC CTG TTC ATT GTC GTC TTC GCC CTT TTG                      505
Phe Leu Leu Phe Leu Phe Ile Val Val Phe Ala Leu Leu
                    160                 165

GGA ATG CAA CTC TTC GGC GGC CAG TTT AAT TTC GAT NAA                      544
Gly Met Gln Leu Phe Gly Gly Gln Phe Asn Phe Asp Glu
        170                 175                 180

GGG ACT CCT CCC ACC AAC TTC GAT ACT TTT CCA GCA GCA                      583
Gly Thr Pro Pro Thr Asn Phe Asp Thr Phe Pro Ala Ala
                185                 190
```

```
ATA ATG ACG GTG TTT CAG ATC CTG ACG GGC GAA GAC TGN         622
Ile Met Thr Val Phe Gln Ile Leu Thr Gly Glu Asp Trp
195                 200                 205

AAC GAG GTC ATG TAC GAC GGG ATC AAG TCT CAG GGG GGC         661
Asn Glu Val Met Tyr Asp Gly Ile Lys Ser Gln Gly Gly
        210                 215                 220

GTG CAG GGC GGC ATG GTG TTC TCC ATC TAT TTC ATT GTA         700
Val Gln Gly Gly Met Val Phe Ser Ile Tyr Phe Ile Val
                225                 230

CTG ACG NTC TTT GGG AAC TAC ACC CTC CTG AAT GTG TTC         739
Leu Thr Xaa Phe Gly Asn Tyr Thr Leu Leu Asn Val Phe
        235                 240                 245

TTG GCC ATN GCT GTG GAC AAT CTG GCC AAC GCC CAG GAG         778
Leu Ala Ile Ala Val Asp Asn Leu Ala Asn Ala Gln Glu
                250                 255

CTC ACN AAG NAC GAG CAA GAG GAA GAA GCA GCG NAC             817
Leu Thr Lys Asp Glu Gln Glu Glu Glu Ala Ala Asn
260                 265                 270

CAG AAA CTT GCC CTA CAG NAA GCC AAG GAG GTG GNA GAA         856
Gln Lys Leu Ala Leu Gln Lys Ala Lys Glu Val Ala Glu
        275                 280                 285

GTG AGT CCT CTG TCC GCG GCC AAC ATG TCT ATA GCT GTG         895
Val Ser Pro Leu Ser Ala Ala Asn Met Ser Ile Ala Val
                290                 295

AAA GAG CAG AAG AAT                                         910
Lys Glu Gln Lys Asn
    300
```

(2) INFORMATION FOR SEQ ID NO: 17:

(i) SEQUENCE CHARACTERISTICS:
        (A) LENGTH: 1100 nucleotides
        (B) TYPE: Nucleotide
        (C) STRANDEDNESS: Single
        (D) TOPOLOGY: Linear (ii) MOLECULE TYPE: cDNA (xi) SEQUENCE DESCRIPTION: SEQ ID NO:17:

```
G GGC GAC ACT GAG TGC CGG GAG TAC TGG CCA GGA CCC           37
  Gly Asp Thr Glu Cys Arg Glu Tyr Trp Pro Gly Pro
  1               5                   10

AAC TTT GGC ATC ACC AAC TTT GAC AAT ATC CTG TTT GCC         76
Asn Phe Gly Ile Thr Asn Phe Asp Asn Ile Leu Phe Ala
            15                  20                  25

ATC TTG ACG GTG TTC CAG TGC ATC ACC ATG GAG GGC TGG         115
Ile Leu Thr Val Phe Gln Cys Ile Thr Met Glu Gly Trp
                30                  35

ACT GAC ATC CTC TAT AAT ACA AAC GAT GCG GCC GGC AAC         154
Thr Asp Ile Leu Tyr Asn Thr Asn Asp Ala Ala Gly Asn
        40                  45                  50

ACC TGG AAC TGG CTC TAC TTC ATC CCT CTC ATC ATC ATC         193
Thr Trp Asn Trp Leu Tyr Phe Ile Pro Leu Ile Ile Ile
                55                  60

GGC TCC TTC TTC ATG CTC AAC CTG GTG CTG GGC GTG CTC         232
Gly Ser Phe Phe Met Leu Asn Leu Val Leu Gly Val Leu
65                  70                  75

TCG GGG GAG TTT GCC AAG GAG CGA GAG AGG GTG GAG AAC         271
Ser Gly Glu Phe Ala Lys Glu Arg Glu Arg Val Glu Asn
        80                  85                  90

CGC CGC GCC TTC CTG AAG CTG CGC CGG CAG CAG CAG ATC         310
Arg Arg Ala Phe Leu Lys Leu Arg Arg Gln Gln Gln Ile
```

-continued

```
                       95                          100
GAG CGA GAG CTC AAC GGG TAC CTG GAG TGG ATC TTC AAG              349
Glu Arg Glu Leu Asn Gly Tyr Leu Glu Trp Ile Phe Lys
    105                 110                 115

GCG GAG GAA GTC ATG CTG GCC GAG GAG GAC AGG AAT GCA              388
Ala Glu Glu Val Met Leu Ala Glu Glu Asp Arg Asn Ala
                120                 125

GAG GAG AAG TCC CCT TTG GAC GTG CTG AAG AGA GCG GCC              427
Glu Glu Lys Ser Pro Leu Asp Val Leu Lys Arg Ala Ala
130                 135                 140

ACC AAG AAG AGC AGA AAT GAC CTG ATC CAC GCA GAG GAG              466
Thr Lys Lys Ser Arg Asn Asp Leu Ile His Ala Glu Glu
        145                 150                 155

GGA GAG GAC CGG TTT GCA GAT CTC TGT GCT GTT GGA TCC              505
Gly Glu Asp Arg Phe Ala Asp Leu Cys Ala Val Gly Ser
                160                 165

CCC TTC GCC CGC GCC AGC CTN AAG AGC GGG AAG ACA GAG              544
Pro Phe Ala Arg Ala Ser Leu Lys Ser Gly Lys Thr Glu
        170                 175                 180

AGC TCG TCA TAC TTC CGG AGG AAG GAG AAG ATG TTC CGG              583
Ser Ser Ser Tyr Phe Arg Arg Lys Glu Lys Met Phe Arg
                185                 190

TTT TTT ATC CGG CGC ATG GTG AAG GCT CAG ANC TTC TAC              622
Phe Phe Ile Arg Arg Met Val Lys Ala Gln Ser Phe Tyr
195                 200                 205

TGG GTG GTG CTG TGC GTG GTG GCC CTG AAC ACA CTG TGT              661
Trp Val Val Leu Cys Val Val Ala Leu Asn Thr Leu Cys
                210                 215                 220

GTG GCC ATG GTG CAT TAC AAC CAG CCG CGG CGG CTT ACC              700
Val Ala Met Val His Tyr Asn Gln Pro Arg Arg Leu Thr
                    225                 230

ACG ACC CTG TAT TTT GCA GAG TTT GTT TTC CTG GGT CTC              739
Thr Thr Leu Tyr Phe Ala Glu Phe Val Phe Leu Gly Leu
        235                 240                 245

TTC CTC ACA GAG ATG TCC CTG AAG ATG TAT NGC CTG GGG              778
Phe Leu Thr Glu Met Ser Leu Lys Met Tyr Gly Leu Gly
                250                 255

CCC AGA AGC TAC TTC CGG TCC TCC TTC AAC TGC TTC GAC              817
Pro Arg Ser Tyr Phe Arg Ser Ser Phe Asn Cys Phe Asp
260                 265                 270

TTT GGG GTC ATC GTG GGG AGC GTC TTT GAA GTG GTC TGG              856
Phe Gly Val Ile Val Gly Ser Val Phe Glu Val Val Trp
            275                 280                 285

GCG GCC ATC AAG CCG GNA AGC TCC TTT GGG ATC AGT GTG              895
Ala Ala Ile Lys Pro Gly Ser Ser Phe Gly Ile Ser Val
                290                 295

CTG CNG GCC CTC CGC CTG CTG AGG ATC TTC AAA GTC ACG              934
Leu Arg Ala Leu Arg Leu Leu Arg Ile Phe Lys Val Thr
        300                 305                 310

AAG TAC TGG AGC TCC CTG CGG AAC CTG GTG GTG TCC CTG              973
Lys Tyr Trp Ser Ser Leu Arg Asn Leu Val Val Ser Leu
                315                 320

CTG AAC TCC ATG AAG TCC ATC ATC AGC CTG CTC TTC TTN              1012
Leu Asn Ser Met Lys Ser Ile Ile Ser Leu Leu Phe Xaa
325                 330                 335

CTC TTC CTG TTC ATT GTG GTC TTC NNN CTG CTG GGG ATN              1051
Leu Phe Leu Phe Ile Val Val Phe Xaa Leu Leu Gly Xaa
            340                 345                 350

CAG CTG TTT NNG GGA CAG TTC AAC TTC CAG GAT GAG ACT              1090
```

-continued

```
Gln Leu Phe Xaa Gly Gln Phe Asn Phe Gln Asp Glu Thr
            355                 360

CCC ACA ACC A                                           1100
Pro Thr Thr
    365
```

TISSUE-SPECIFIC HUMAN NEURONAL CALCIUM CHANNEL SUBTYPES AND THEIR USE

This application is a continuation of application Ser. No. 08/094,712, filed Jul. 19, 1993, now abandoned; which is a CIP of Ser. No. 07/858,278, filed Mar. 26, 1992, now abandoned, and a CIP of Ser. No. 08/064,778, filed May 19, 1993, now abandoned.

Calcium ions have a multitude of functions in every biological system. Cellular calcium homoestasis plays a particularly essential role in the physiology of nerve cells. The intracellular calcium concentration is approximately 0.1 $\mu$M, as oodosed to 1 mM outside the nerve cell. This strong concentration gradient ($\times$10,000) is primarily regulated by voltage-operated calcium channels (VOCC) which can be blocked by certain calcium antagonists. During a cerebral ischaemia (cerebral apoplexy), the calcium homoeostasis in neurons of the affected infarct region is changed considerably. The voltage-dependent calcium channels are maintained in the open state by prolonged membrane depolarisation, which results in a massive influx of calcium ions. During this process, the intracellular calcium concentration rises by a factor of 1000. The high excess of calcium activates various calcium/calmodulin-dependent cellular enzyme systems such as, for example, kinases, proteases and phosoholioases, by binding with calmodulin. These enzyme systems together result in irreversible damage to nerve cells when activated over a prolonged period.

A therapeutic approach to the protection of nerves during cerebral ischaemia is the reversible blocking of the massive calcium influx into the nerve cell. The voltage-dependent neuronal calcium channels are thus a suitable pharmacological target. VOCCs exist in a variety of muscle cells (vascular muscles, heart muscles and skeletal muscles). neurons and secretory cells which have tissue-specific physiological properties.

Electrophysiological investigations (Tsien et al., 1988, Trends in Neurol. Sci. 11: 431–438) suggest at least three different types of VOCC (L-, N- and T-channels). The 1,4-dihydropyridines (DHPs) are potent blockers of the L-type calcium channels, which can be found in muscle cells and also in nerve cells. The rabbit skeletal muscle dihydropyridine receptor has been characterised biochemically and cloned (Tanabe et al., 1987, Nature 328: 313–318). The primary sequence of this $\alpha$1 subunit of the VOCC, derived from the cDNA data, is consistent with a 212 kD transmembrane protein having give N-glycosylation sites and seven possible phosphorylation sites. The protein contains four trans-membrane domains which resemble each other, each of which has six presumably $\alpha$-helical membrane-penetrating segments (S1–S6). In each case the fourth trans-membrane segment (S4) of each domain contains a regular pattern of positive charges (Lys, Arg) which can form the voltage sensor of the calcium channel. The structure of this cloned $\alpha$1 subunit is consistent with an ion-conducting voltage-controlled unit of the DHP-sensitive calcium channel.

The cloned carp skeletal muscle DHP-R cDNA clone (Grabner et al., 1991, Proc. Natl. Aca. Sci. (USA), 88:727–731) was used as hybridisation probe to isolate related human calcium channel genes from neurons and to characterise them. This cloning strategy allowed the isolation and characterisation of a number of various homologous cDNA clones from human neuronal cDNA libraries and we have clear evidence that various calcium channel subtypes exist in human central nervous system. Further neuronal sub-types have novel receptor sites for which no ligands (agonists, antagonists) have been disclosed to date. The cloned calcium channel sub-types are to be expressed in transformed animal cells (for example cos cells, mouse L cells, CHO cells etc.) (Gluzman, 1981, Cell 23:175, and Chen. et al., 1987, Mol. Cell. Biol. 7:2745–2752) and employed in binding assays and/or functional test assays for screening novel, sub-type-specific ligands. This involves the cloning of complete or partial cDNA genes of various calcium channel subtypes (including heart channels, vascular channels and skeletal muscle channels) into suitable eukaryotic expression vectors (Sambrook et al., 1989, in: Molecular Cloning, A laboratory manual, ed. Chris Nolan, Cold Sring Harbor Laboratory Press, New York, N.Y.). Protein expression is controlled either by homologous regulatory elements (promoters and enhancers) or heterologous promoters (viral, for example SV40, BPV, CMV, etc., or inducible, for example metallothionein, cAMP, calcium, temperature, etc.) in combination with known enhancers and RNA processing signals (for example capping, polyA).

It is furthermore intended to develop with these recombinant cell systems functional calcium flux assays, with the aid of which specific ligands can be tested for their agonistic or antagonistic effects. The distructiveness and the main advantage of these recombinant assays compared with conventional assays (cerebral membrane preparations, cell lines) lie in the purity of the receotor/channel preparation since it is exclusively the recombinant expressed neuronal calcium channel sub-type which is present on the surface of tranfected animal cells in any number desired. This is an essential prerequisite for the selection of specific neuronal calcium channel ligands that do not affect calcium channels of non-neuronal tissue types.

The following section will mention some examples of the use of the above-described recombinant screening assays.

1. Receptor Binding Assay

Animal cells which have been transformed with human calcium channel sub-types (example: see above) can be cultured and used for the preparation of membranes. These membrane preparations can be used for binding studies with various radiolabelled substance classes (Examples 1–5) for screening novel ligands in a competition assay. Examples of known calcium channel-binding substances are:
1. phenylalkylamines,
2. benzothiazepines,
3. dihydropyridines,
4. bisphenylbutylpiperidines,
5. omega-conotoxins.

2. 45 Calcium-flux Assay

The cell membranes of cultured cells which have been transformed with human calcium channel sub-types (see above) can be depolarised by potassium ions or alkaloids such as, for example, veratridine. Membrane depolarisation causes calcium channels to open, resulting in an influx of calcium ions into the cells. This voltage-dependent calcium influx can be measured using radio-labelled calcium (45Ca) (example: Messina et al., 1985, J. Pharmacology and Exp. Therapeutics 235:407–411), and used for functional testing/screening of calcium channel antagonists or agonists.

3. Fura-2 Test

Animal cells which exoress human calcium channel (see above) can be used in the presence of calcium-sensitive fluorescent stains (for example fura-2 or fluoro-3) for measuring the intracellular calcium concentration after opening and blocking of the calcium channels (example: Rosario et al., 1989, Neurosci. 29,735–747). The change in intracellular calcium concentration can be measured fluorimetrically (spectrophotometrically). This recombinant cell system can be used as a functional test for finding sub-type-specific calcium channel ligands (agonists and antagonists).

4. Electrophysiology

The calcium fluxes produced by membrane depolarisation can be measured electrophysiologically (example: Carbone et al., 1990, Pflügers Arch., 416: 170–179). With the aid of the recombinant animal cell lines (see above), human calcium channels can be used for direct physical measurement and pharmacological characterisation of the effect of potential calcium channel antagonists or agonists.

5. Indirect Methods of Measurement

Many cellular processes are controlled by the intracellular calcium ion concentration (for example, receptor-mediated signal transfer, various enzyme reactions such as phosphorylation reactions, dephosohorylation reactions, release of neurotransmitters, calcium-dependent gene regulation, etc.). Some of these biochemical reactions can be measured using a specific assay. A recombinant calcium channel-expressing cell system can therefore be used for indirectly (physiologically) assessing the effect of calcium channel modulators on calcium-dependent processes in the cell (example: Zernig et al., 1986, Eur. J. Pharmacol. 128, 221–229).

In addition, changes introduced by targeted mutageneses such as, for example, point mutations, insertions, deletions, exchange of DNA segments of various calcium channel sub-types, allow direct effects on physiological processes to be assessed (example: Yool and Schwarz, 1991, Nature 349: 700–704).

1. cDNA Methods/Banks

The following commercially available cDNA libraries were used for isolating human neuronal calcium channels by means of homologous screening:

a) cDNA library from human neuroblastoma cell line Vector: Lambda gt10

| Obtained from: | Clontech Laboratories, Inc. Palo Alto, CA. USA: (Cat. No. HL 1007a) |
|---|---| b) cDNA library from human hippocampus;
   Vector: Lambda ZAPII

| Obtained from: | Stratagene Inc. La Jolla, CA. USA (Cat. No. 936205) |
|---|---| c) cDNA library from human temporal cortex Vector: Lambda ZAPII

| Obtained from: | Stratagene Inc., La Jolla, CA. USA (Cat. No. 935205) |
|---|---| d) cDNA library from human visual cortex Vector: Lambda gt10

| Obtained from: | Clontech Laboratories, Palo Alto, CA. USA (Cat. No. HL 1081a) |
|---|---| e) cDNA library from human frontal cortex Vector: Lambda ZAPII

| Obtained from: | Stratagene Inc. La Jolla, CA. USA (Cat. No. 935205) |
|---|---|

2. Screening of cDNA Libraries 2.1 Plating of the cDNA libraries and processing of nitrocellulose filters Plating of the cDNA libraries and the processing of nitrocellulose filters was carried out following the instructions of the manufacturers or by the method of Sambrook et al., 1989, (Molecular Cloning, A laboratory manual, ed. Chris Nolan, Cold Spring Harbor Laboratory Press, New York, N.Y.).

2.2 Hybridisation probes

The hybridisation probe used was a cDNA clone (FIG. 1), 6.1 kb in length, which contains the entire encoding reaion of the $\alpha_1$-subunit (SU) the calcium channel the skeletal muscles carp (Cyprinus carpic) including 5'- and 3'-non-translated regions (Grabner et al., 1990, Proc. Natl. Acad. Sci. (USA), 88: 727–731). The following sections of this clone were used for homology screening (FIG. 1):

the entire CDNA clone (6.1 kb)
subfragment 1,336
subfragment 1,509
subfragment 1,247.

The following fragments of human calcium channel cDNA clones were used for the further screening of cDNA banks:

insert of clone p 1247-9.1.1.2 (811 bp)
subfragment of clone p 1247-14.1.1.1 (EcoRI-KpnI; 205 bp)
subfragment of clone p 1247-5.1.2.1.1 (EcoRI-SacI; 710 bp)
insert of clone pCA 33 (684 bp)
subfragments of clone pCA 3 (EcoRI-EcoRI, 640 pb; PstI-PstI, 198 bp; PstI-Pst, 600 bp)

2.3 Labelling of DNA fragments with radioactive DNA precursors

Standard protocols (Sambrook et al., 1989 in: Molecular Cloning, A laboratory manual, ed. Chris Nolan, Cold Spring Harbor Laboratory Press, New York, N.Y.) in conjunction with a commercially available "Random Primed Labeling Kit" (Boehringer Mannheim GmbH, Post Box 310120, D-6800 Mannheim; Cat. No. 1004 760) were used for labelling double-stranded DNA fragments.

2.4 Conditions for hybridisation and washing

Nitrocellulose filters were hybridised overnight with radiolabelled cDNA fragments in 30% formamide, 5×Denhardt's solution, 5×SSC, at 42° C., and subsequently washed as follows:

2×20 minutes in 2×SSC, 0.05% SDS, at room temperature
2×20 minutes in 0.2×SSC, 0.2% SDS, at 45° C., and
1×20 minutes in 0.2×SSC, at room temperature.

A Kodak X-OMAT AR X-ray film was then exposed to the filters for various oeriods of time at −80° C., using intensifying screens.

3. Isolation of Lambda Phages; Subcloning and Sequencing of the cDNA Inserts 3.1 cDNA inserts from lambda gt10

Lambda-phage DNA was isolated and cleaved with EcoRI, the cDNA inserts were subcloned in a pUC derivative (pT7T3 18U; manufactured by Pharmacia), and the nucleotide sequence was subsequently determined by Sanger's dideoxy-termination method (Sanger et al., 1977, Proc. Natl. Acad. Sci. USA, 74: 5463–5467) using Sequenase (manufactured by USB, Cleveland, Ohio, USA).

3.2 cDNA inserts from lambda ZAPII 3.2.1 Excising the complete cDNA inserts from lambda phages, and introducing the inserts into plasmids The cDNA inserts from nositive lambda-ZAPII phages were excised following the protocol of the manufacturer (Stratagene) by means of an fl-derived helper phage and converted into plasmid form.

3.2.2 Size determination and sequence analysis of the isolated cDNA insert

Plasmid DNA was oreoared from XL1-Blue cells which carried a recombinant pBluescript plasmid (Sambrook, J., et al., (1989) in: Molecular cloning, A laboratory manual, ed. Chris Nolan, Cold Sring Harbor Laboratory Press, New York, N.Y.), and 0.5 µg aliquots of this DNA were treated with the restriction enzyme EcoRI. The total length of the inserted cDNA could be calculated from the number and size of the DNA fragments formed. The nucleotide sequence of the cDNA present was determined on double-stranded DNA by Sanger's method, using SEQUENASE (USB, Cleveland, Ohio, USA).

4. Description of Human Neuronal Calcium Channel cDNA Clones Isolated to Date

To date, the following CDNA clones have been isolated and were identified as calcium channels by comparing the DNA and amino acid sequence with other known calcium channel sequences (for example, the calcium channel nucleotide sequence from rabbit skeletal muscles (Tanabe et al., Nature 328, 313–318); the assignment of numbers to the nucleotides or amino acids is analogous to the assignment of numbers in the EMBL data bank):

Combination of Overlapping Calcium Channel cDNA Subclones with Identical Nucleotide Sequence cDNA subclones with identical overlapping sequences are combined via suitable restriction cleavage sites to give a complete or partial cDNA clone which encodes a certain calcium channel sub-type. This cDNA aene is expressed in mammalian cells by means of a eukaryotic expression vector and used in the assay described in the examples Items 1 to 5.

1. pCA33 (SEQ ID NO:1):

Length: 683 nucleotides. position AA 1,000–1,230 (3' additional 3 AA); comprises sequences of the third domain from IIIs6 to fourth domain IVs3.

2. p1247-5.1.2.1.1 (SEQ ID NO:2):

Length approx. 4,919 bp; position from AA 343 to the end of the coding region; accordingly contains the complete gene after domain I.

3. p 1247-9.1.2 (SEQ ID NO:3):

Length 811 bp; position AA 1,115–1,390, and accordingly embraces the entire domain IV (s1 to s6) and flanking sequences on both sides.

4. p1247-10.1.1.1 (SEQ ID NO:4):

Length 1,354 bp; position AA 1,050–1,512, and accordingly include the end of the third domain (IIIs6), the entire domain IV, and approximately 130 C-terminally flanking AA, that are part of the last cytoplasmatic portion of the protein.

5. p1247-14.1.1 (SEQ ID NO:5):

Length: 5,438 bp; position AA 967–1,327. This clone overlaps to a large extent (position 1–3,238) with clone pR14-5.3.3.1. (Position 2,988–4,232). The two clones are almost identical in the overlapping portion. The differences from pR14-5.3.3.1 are the following (nucleotide and position in pR14-5.3.3.1 are in each case in parentheses):

(1) Cytosine in position 520 (T: 3,507): no change in the derived protein sequence.
(2) Cytosine in position 775 (G: 3,768): no chance in the derived protein sequence.
(3) Cytosine in position 1,617 (T: 4,611).
(4) Adenosine in position 2,360 (G: 5,353).
(5) Deletion of six nucleotides at position 708 (CGGAAA: 3,695–3,700).
(6) Deletion of an adenosine residue at position 1,013; compared with pR14-5.3.3.1, this results in a reading-frame shift so that a stop codon terminates the derived protein in position 1,028–1,030.
(7) From position 3,240 on, there exist a further 2,199 nucleotides of the 3'-non-translated reoion which are absent in pR14-5.3.3.1. This is followed by part of a polyadenylate tail.

Due to the strong similarity of clones p1247-14.1.1.1 and pR14-5.3.3.1, it can be assumed that the deletion of a nucleotide at position 1,013 is an artefact at cDNA synthesis.

6. pR9112-4.1.1 (SEQ ID NO:6):

Length approx. 1,722 bp; position AA 1,223–1,870; this clone accordingly contains, from s4 on, the C-terminal portion of the fourth domain and the complete coding sequence to the actual C-terminus of the protein. This clone is almost identical with overlapping sequences of clone 1247-9.1.1.2. The sequences of pR9112-4.1.1.1 and pR9112-2.1.1.1 are essentially identical (1 bp difference in the 1,464 nucleotides of the overlap which have been sequenced to date); the clones are probably overlapping cDNA clones of the same mRNA.

7. pR9112-10.1.1.1 (SEQ ID NO:7):

Length 2,049 bp; position of AA 991-1,650. This clone contains cDNA sequences which encode part of domain III (s6), the entire fourth domain and part of the C-terminal cytoplasmatic portion of the protein. Clone pR9112-10.1.1.1 differs from pR9112-2.1.1.1 and pR9112-4.1.1.1 by a 57 bp insert (1,454–1,510). This insert has splicing consensus sequences on both ends and therefore suggests the alternative splicing to be the cause of the difference.

8. pR9112-12.1.1.1 (SEQ ID NO:8):

Length 997 bp; position up to AA 1,509. The sequence of this cDNA clone is almost identical to that of clone p1247-14.1.1.1. The 5' end of the clone additionally contains as cloning artefact approx. 250 bp of mitochondrial DNA, and a poly(A) portion of 39 bp.

9. pR9112-2.1.1.1 (SEQ ID NO:9):

Length 1,471 bp; like cDNA clone pR9112-4.1.1.1, this clone contains, from IVs3–4 on, the entire encoding region up to the actual C-terminus of the protein, and also approx. 500 bp of the 3'-non-translated region of the mRNA.

10. pRR5-8 (SEQ ID NO:10):

Length 2,655 bp; this clone contains, at the 5'-end, 235 bp of non-translated sequence followed by an ATG start codon (position 236–238). From this start codon there extends an open reading frame up to the 3'-end of the clone. The protein derived therefrom starts with the actual N-terminus of a calcium channel cDNA gene and contains domains I and II, and a portion of the intracellular loop between domain II and III. From position 1,318 up to the 3'-end, the clone overlaps with clone p1247-5.1.2.1.1. The two clones can be combined with each other, for example at shared XhoI cleavage site (position 1,506–1,511 in the case of pRR5-8) to give a cDNA which, besides the cvptoplasmatic N-terminus, encodes domains I–IV and adjacent cytoplasmatic C-terminal regions of the calcium channel.

11. pR14-5.3.3.1 (SEQ ID NO:11):

Length: 6,232 bp; position AA 358 up to the C-terminus of a calcium channel. This clone contains, at the 5'-end, 252 bp which are 85% homologous with human Alu repeat sequences and which mav have been ligated artificially with the remaining 5,980 bp of the calcium channel cDNA during cDNA cloning. The open reading frame of the calcium channel-encodino cDNA strand encodes 1,931 AA, and includes domains II to IV, and the C-terminal cytoplasmatic oortion of the calcium channel. This is followed by 187 bp of 3'-non-translated region, including a polyadenylation signal at position 6,215–6,220, and terminates with a poly-A tail (44 adenosine residues).

12. pCA3 (SEQ ID NO:12)

Length 2,837 bp; has an internal EcoRI cleavage site (2 subfragments: 2,197 bp, 640 bp). The 5'-end of the cDNA clone is located between domains II and III; the 3'-end at AA 1,622; the clone embraces the complete domains III and IV and part of the C-terminus-encoding sequence. The 5'-end of the cDNA clone overlaps with the 3'-end of clone pCA9.3 over a length of 830 bp. Both cDNA clones are identical over 671 bp, with only the first 159 bp of the 5'-end of clone pCA3 showing no homology with the corresponding section of clone pCA9.3 (FIG. 2, shaded region). Clone pCA 3 and clone pCA9.3 can be combined via a common PmlI restriction cleavage site in the over-lapping region.

13. pCA9.3 (SEQ ID NO:13)

Length 1,857 bp; the 5'-end of the cDNA clone starts immediately after domain I (AA 337); the 3'-end is at AA 922; the cDNA clone contains sequences of the second cytoplasmatic section (between domains I and II) up to and including the 4th transmembrane region of domain III (IIIS4).

14. p1247-4.2.1.1 (SEQ ID NO:14):

Length 920 bp; position AA 1,178–1,496 of the rabbit skeletal muscle $\alpha_1$ subunit (domains IVs3–IVs6). The sequence of clone p1247-4.2.1.1 is completely contained within the sequence of clone p1247-10.1.1.1. Both clones are identical with the exception of a 6 base pair insertion in clone 1247-4 (position 88–93), and 2 further base exchanges.

15. pR5-6cort (SEQ ID NO:15)

Length: 1,424 bp; position AA 25–458. This clone contains, at the 5'-end, a putative splice donor site at position 60, which means that the first 60 nucleotides may represent intron sequences. The calcium channel-encoding region (from position 61 on) embraces part of the N-terminal cytoplasmic region, as well as the entire domain I and the first membrane-oenetrating region (S1) of domain II.

16. pR5-4cort (SEQ ID NO:16)

Length: 910 bp; position AA 409–713. This clone has a 151 bp overlap at its 5'-end with the 3'-end of clone pR5-6cort (100% identity over 151 bp). These two clones therefore represent independently cloned cDNA sections of a single mRNA, and can be combined with each other, for example via the shared Stu I restriction cleavage site.

17. pRR14-35 (5'-end of the clone) (SEQ ID NO:17)

Length: approx. 3,400 bp, of which 1,100 bp have been sequenced to date; position: the 5'-end of the clone is at AA 257 and therefore between the membrane passages S5 and S6 of domain I. In the region which has been sequenced, there is a sequence-identical overlap of the clone with pR14-5.3.3.1 (position 253–964). The two clones pRR14-35 and pR14-5.3.3.1 can thus be regarded as two independently cloned cDNA fragments of an mRNA. Clone pRR14-35 adds 129 AA at the 5'-end of the calcium channel cDNA contained in pR14-5.3.3.1 and thus eliminates the Alu-repeat sequences which is artificially present at the 5'-end of the clone. The two clones can be combined with each other via a joint Bgl II restriction cleavage site.

DESCRIPTION OF THE FIGURES

The upper part (A) of FIG. 1 represents the cDNA of the carp skeletal muscle calcium channel, with the cleavage sites for some restriction endonucleases and the subfragments which were used as screening probes. The lower part (B) shows DNA fragments of the human clones p1247-5.1.2.1.1 and p1247-14.1.1, that were prepared using the restriction enzvmes EcoRI/SacI or EcoRI/KpnI, and the entire cDNA insert of clone p1247-9.1.1.2, which were also used as screening probes.

The upper part (A) of FIG. 2 shows a diagram of the $\alpha_1$-subunit of the rabbit skeletal muscle calcium channel. The domains are shown as boxes and numbered with Roman numerals. Within these domains, the trans-membrane regions are emphasised in the form of black blocks. The lower part (B) shows the portions of human neuronal calcium channels which have been isolated to date, arranged according to their size and their homology with the rabbit skeletal muscle calcium channel protein.

Figure 1:
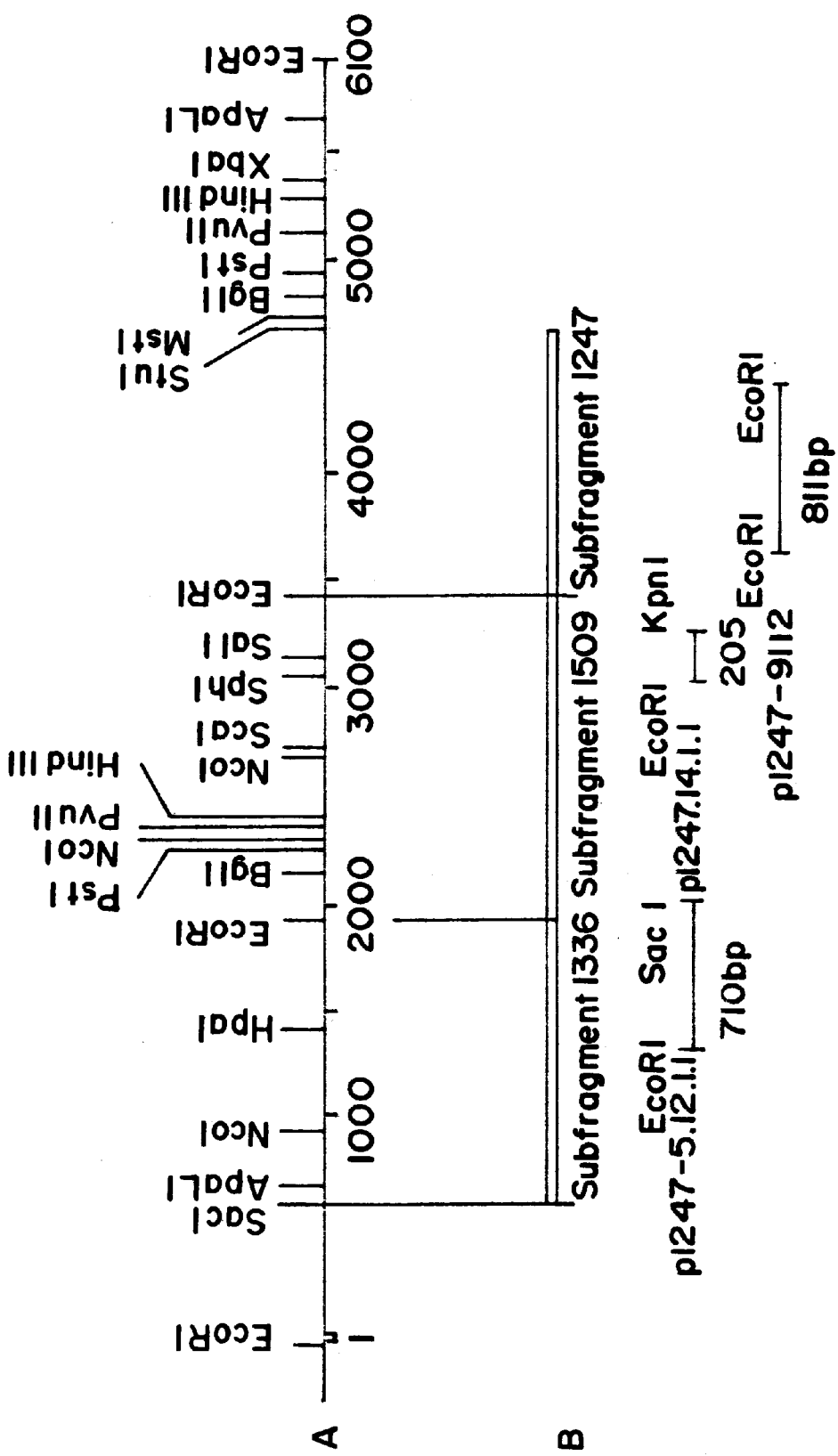
Figure 2:
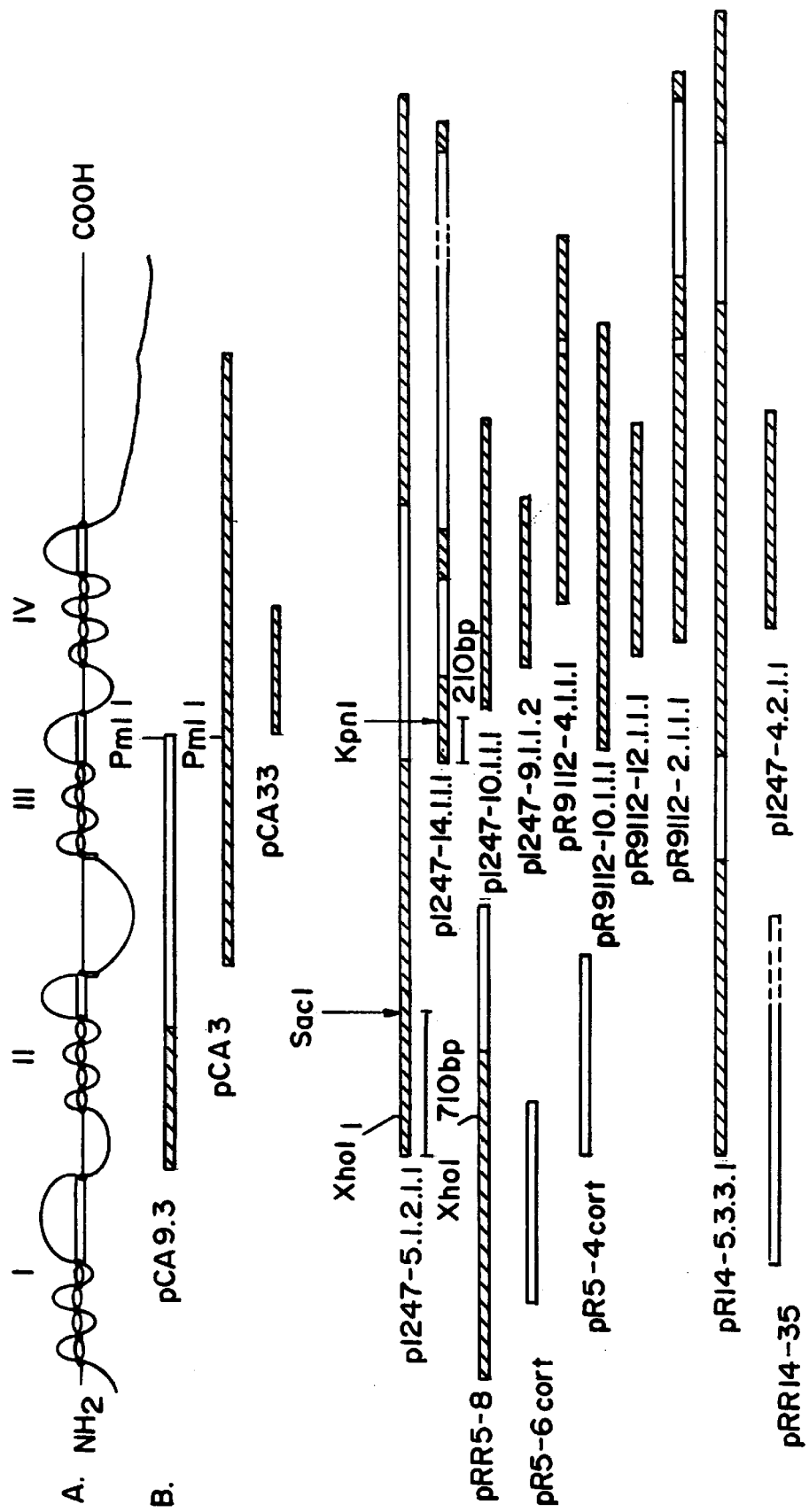
Figure 3:
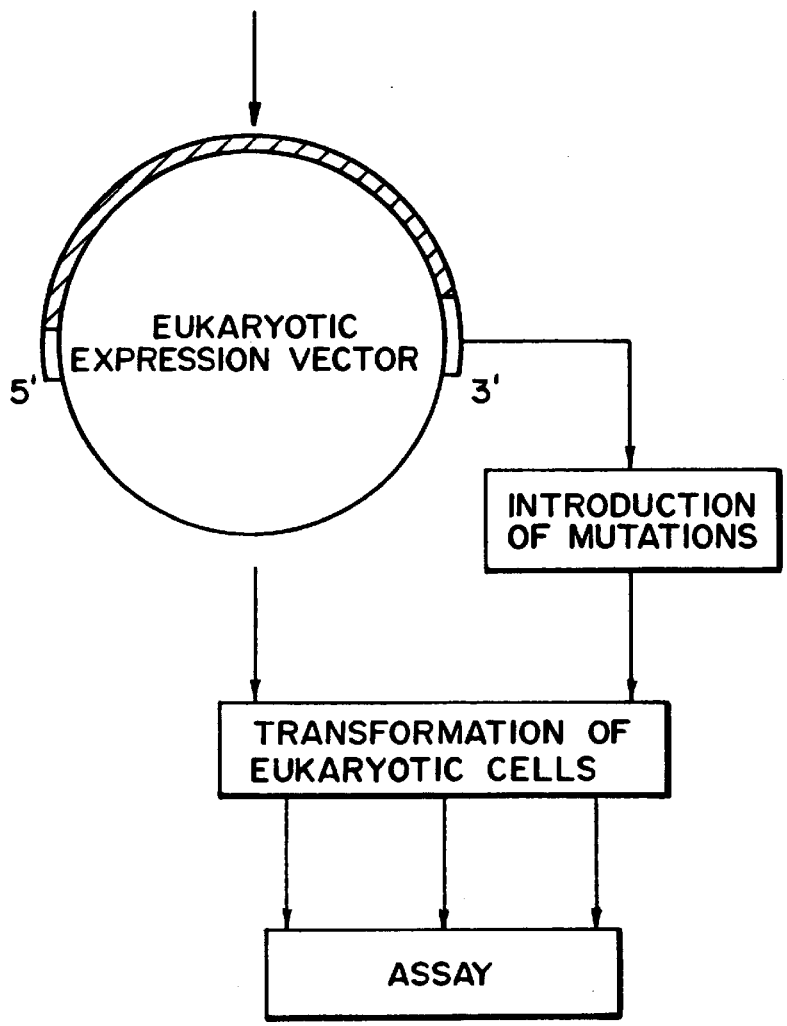
FIG. 3.

Diagram of the cloning and expression of tissue-specific human neuronal calcium channel sub-types and their use in an assay system. The complete cDNA which encodes a calcium channel sub-type is assembled from overlapping lambda phages by means of suitable restriction cleavage sites and cloned into a eukarvotic expression vector.

This vector is used for transforming suitable eukaryotic cells, and stable cell lines are produced which express the protein of a calcium channel subtype. These stable cell lines are then used in the above-described receptor binding assays.

Additional mutations introduced into the calcium channel-encoding cDNA are intended to help identify structural/functional domains.

We claim:

1. An isolated and purified DNA sequence comprising a nucleotide sequence selected from the group consisting of SEQ ID NOS.: 2–5, 9–14 and 16.

2. The isolated and purified DNA sequence according to claim 1, which comprises a nucleotide sequence selected from the group consisting of SEQ ID NOS.: 12 and 13.

3. The isolated and purified DNA sequence according to claim 1, which comprises a nucleotide sequence selected from the group consisting of SEQ ID NOS.: 3, 9 and 14.

4. The isolated and purified DNA sequence according to claim 1, which comprises a nucleotide sequence selected from the group consisting of SEQ ID NOS.: 4 and 16.

5. The isolated and purified DNA sequence according to claim 1, which comprises a nucleotide sequence selected from the group consisting of SEQ ID NOS.: 5 and 11.

6. The isolated and purified DNA sequence according to claim 1, which comprises a nucleotide sequence selected from the group consisting of SEQ ID NOS.: 2 and 10.

7. An isolated and purified DNA sequence selected from the group consisting of SEQ ID NOS.: 2–5, 9–14 and 16.

* * * * *